United States Patent
Demers et al.

(10) Patent No.: US 9,474,891 B2
(45) Date of Patent: Oct. 25, 2016

(54) TRANSDERMAL NEUROSTIMULATOR ADAPTED TO REDUCE CAPACITIVE BUILD-UP

(71) Applicant: Thync Global, Inc., Los Gatos, CA (US)

(72) Inventors: Remi Demers, Saint-Nicolas (CA); Jay Frederick Hamlin, Santa Cruz, CA (US); Wing Law, Cupertino, CA (US); Sumon K. Pal, Boston, MA (US); Jonathan Charlesworth, Boston, MA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

(21) Appl. No.: 14/715,470

(22) Filed: May 18, 2015

(65) Prior Publication Data
US 2015/0335888 A1    Nov. 26, 2015

Related U.S. Application Data

(60) Provisional application No. 62/002,910, filed on May 25, 2014, provisional application No. 62/076,459, filed on Nov. 6, 2014, provisional application No. 62/099,950, filed on Jan. 5, 2015, provisional (Continued)

(51) Int. Cl.
*A61N 1/04* (2006.01)
*A61N 1/36* (2006.01)

(52) U.S. Cl.
CPC ........... *A61N 1/0456* (2013.01); *A61N 1/0492* (2013.01); *A61N 1/36025* (2013.01)

(58) Field of Classification Search
CPC ................... A61N 1/36025; A61N 1/0456
See application file for complete search history.

(56) References Cited

U.S. PATENT DOCUMENTS

| 4,431,000 A | 2/1984 | Butler et al. |
| 4,646,744 A | 3/1987 | Capel |
| 4,664,117 A | 5/1987 | Beck |

(Continued)

FOREIGN PATENT DOCUMENTS

| EP | 502919 B1 | 11/1993 |
| EP | 801957 A1 | 10/1997 |

(Continued)

OTHER PUBLICATIONS

Tyler et al.; U.S. Appl. No. 14/826,776 entitled "Transcranial ultrasound systems," filed Aug. 14, 2015.

(Continued)

*Primary Examiner* — Rex R Holmes
(74) *Attorney, Agent, or Firm* — Shay Glenn LLP

(57) ABSTRACT

Neurostimulators for application of transdermal electrical stimulation (TES) and methods of using them for comfortably inducing a cognitive effect. The apparatuses described herein may include hardware, software and/or firmware components that are configured to safely and effectively apply high current intensity (e.g., using a high voltage source). These apparatuses may also include circuitry configured to deliver complex (e.g., ensemble) TES current waveforms that incorporate capacitive discharge current at selected portions of the delivered waveform to enhance user comfort. Methods of operating these devices to reduce capacitance buildup on the user's skin by delivering integrated capacitive discharging currents are also included.

17 Claims, 37 Drawing Sheets

Related U.S. Application Data application No. 62/075,896, filed on Nov. 6, 2014, provisional application No. 62/099,960, filed on Jan. 5, 2015, provisional application No. 62/100,022, filed on Jan. 5, 2015.

(56) References Cited

U.S. PATENT DOCUMENTS

| | | |
|---|---|---|
| 5,144,952 A | 9/1992 | Frachet et al. |
| 5,183,041 A | 2/1993 | Toriu et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 6,066,163 A | 5/2000 | John |
| 6,324,432 B1 | 11/2001 | Rigaux et al. |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,623,430 B1 | 9/2003 | Slayton et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 * | 2/2010 | Castel et al. .............. 607/148 |
| 7,891,615 B2 | 2/2011 | Bevirt |
| 7,949,403 B2 | 5/2011 | Palermo et al. |
| 8,086,318 B2 * | 12/2011 | Strother et al. ............. 607/48 |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,627 B2 | 7/2013 | Bikson et al. |
| 8,506,469 B2 | 8/2013 | Dietrich et al. |
| 8,560,075 B2 | 10/2013 | Covalin |
| 8,639,343 B2 | 1/2014 | De Vos |
| 8,688,239 B2 | 4/2014 | Hartlep et al. |
| 8,843,210 B2 | 9/2014 | Simon et al. |
| 8,903,494 B2 | 12/2014 | Goldwasser et al. |
| 9,002,458 B2 | 4/2015 | Pal et al. |
| 9,014,811 B2 | 4/2015 | Pal et al. |
| 2002/0116036 A1 | 8/2002 | Daignault et al. |
| 2003/0225323 A1 | 12/2003 | Kiani et al. |
| 2004/0098065 A1 | 5/2004 | Hagglof et al. |
| 2004/0267333 A1 | 12/2004 | Kronberg |
| 2005/0165460 A1 | 7/2005 | Erfan |
| 2005/0267388 A1 | 12/2005 | Hanna |
| 2006/0064139 A1 | 3/2006 | Chung et al. |
| 2007/0088419 A1 | 4/2007 | Fiorina et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0045882 A1 | 2/2008 | Finsterwald |
| 2008/0132974 A1 | 6/2008 | Strother et al. |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0101366 A1 | 4/2012 | Ruohonen et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245653 A1 | 9/2012 | Bikson et al. |
| 2012/0302912 A1 | 11/2012 | Moffitt et al. |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0267761 A1 | 10/2013 | Bentwich |
| 2013/0282095 A1 | 10/2013 | Mignolet et al. |
| 2013/0318168 A1 | 11/2013 | Demain et al. |
| 2013/0325096 A1 | 12/2013 | Dupelle et al. |
| 2014/0031895 A1 | 1/2014 | Rahimi et al. |
| 2014/0277324 A1 | 9/2014 | DiUbaldi et al. |
| 2014/0336728 A1 * | 11/2014 | Franke et al. .............. 607/62 |
| 2015/0088224 A1 | 3/2015 | Goldwasser et al. |
| 2015/0174403 A1 | 6/2015 | Pal et al. |
| 2016/0008632 A1 | 1/2016 | Wetmore et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 10-108913 A | 4/1998 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2009-85901 A | 4/2009 |
| JP | 2011-118293 A | 6/2011 |
| WO | WO92/06737 A1 | 4/1992 |
| WO | WO93/17628 A1 | 9/1993 |

(56) References Cited

FOREIGN PATENT DOCUMENTS

| | | |
|---|---|---|
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156052 A2 | 11/2012 |
| WO | WO2013/071307 A1 | 5/2013 |
| WO | WO2013/192582 A1 | 12/2013 |

OTHER PUBLICATIONS

Pal et al.; U.S. Appl. No. 14/634,551 entitled "Methods for user control of neurostimulation to modify a cognitive state," filed Feb. 27, 2015.

Jeffery et al.; U.S. Appl. No. 14/634,664 entitled; "Cantilever electrodes for transdermal and transcranial stimulation," filed Feb. 27, 2015.

Jeffery et al.; U.S. Appl. No. 14/634,661 entitled "Methods for attaching and wearing a neurostimulator," filed Feb. 27, 2015.

Goldwasser et al.; U.S. Appl. No. 14/715,461 entitled "Wearable transdermal neurostimulator having cantilevered attachment," filed May 18, 2015.

Charlesworth et al.; U.S. Appl. No. 14/715,476 entitled "Methods and apparatuses for amplitude-modulated ensemble waveforms for neurostimulation," filed May 18, 2015.

Demers et al.; U.S. Appl. No. 14/715,483 entitled "Methods and apparatuses for control of a wearable transdermal neurostimulator to apply ensemble waveforms," filed May 18, 2015.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Chaieb et al.; Transcranial alternating current stimulation in the low kHz range increases motor cortex excitability; Restor Neurol Neurosci; 29(3); pp. 167-175; Mar. 2011.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

GoFLOW; tDCS Kit; product information; 9 pgs..; printed Feb. 10, 2014 (http://flowstateengaged.com/).

Gracenote; Timeline-metadata-api; 3 pages.; retrieved from the internet Jul. 7, 2015; (https://github.com/gracenote/timeline-metadata-api/blob/master/README.md).

Grindhouse Wetware; Thinking Cap; product information; 1 pg.; printed Feb. 10, 2014 (http://www.grindhousewetware.com/thinkingcap.html).

Kanai et al.; Frequency-dependent electrical stimulatioin of the visual cortex; Curr. Biol.; 18(23); pp. 1839-1843; Dec. 9, 2008.

Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.

Rossini et al.; Non-invasive electrical and magnetic stimulation of the brain, spinal cord and roots: basic principles and procedures for routine clinical application; Electroenceph. Clin. Neurophysiol.; 91(2); pp. 79-92; Aug. 1994.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

STD Pharmaceutical Products; Idrostar intophoresis machine (product and use information); 9 pgs.; Dec. 2011 (printed Feb. 11, 2014 from http://www.iontophoresis.info/instructions/).

Terney et al.; Increasing human brain excitability by transcranial high-frequency random noise stimulation; The Journal of Neuroscience; 28(52); pp. 14127-14155; Dec. 2008.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filed and any foreign priority date).

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 61/550,334 entitled "Improvement of Direct Communication," filed Oct. 21, 2011.

Jeffery et al.; U.S. Appl. 15/169,445 entitled "Methods and apparatuses for transdermal electrical stimulation," filed May 31, 2016.

Pal et al.; U.S. Appl. No. 15/170,878 entitled "Apparatuses and methods for neuromodulation," filed Jun. 1, 2016.

* cited by examiner

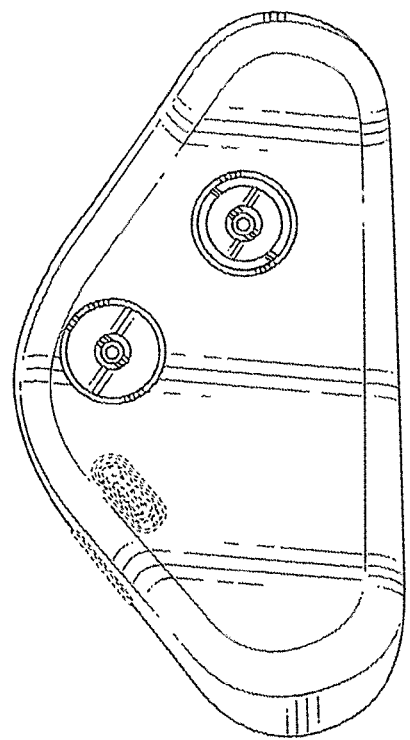
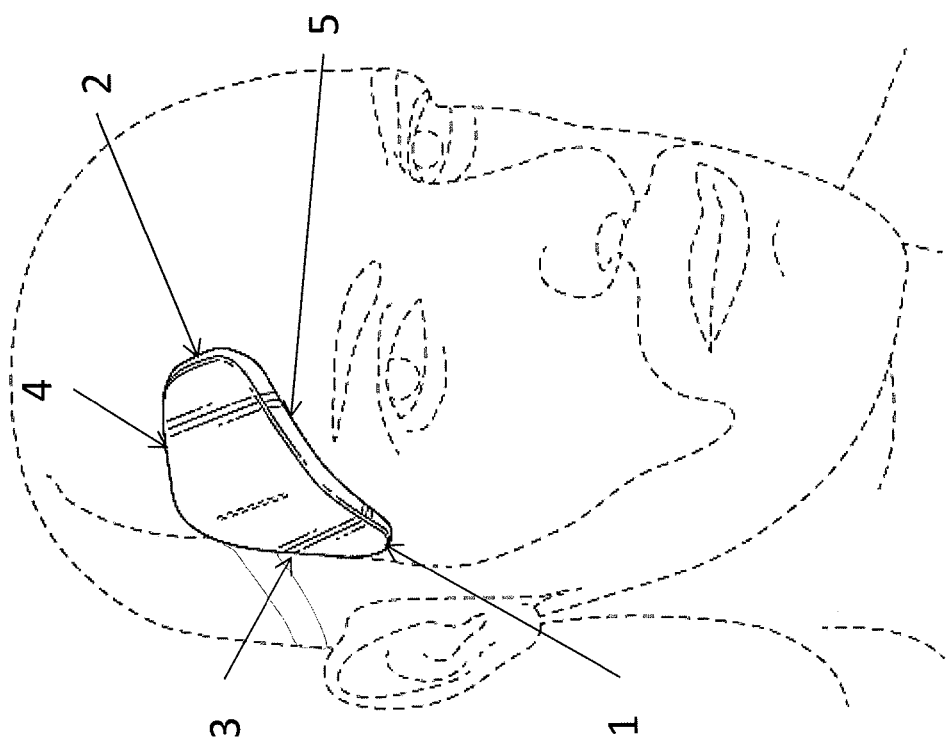
FIG. 1B
FIG. 1A

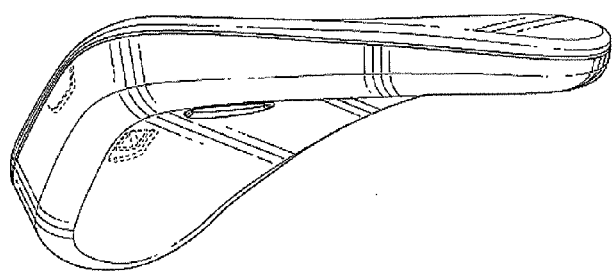
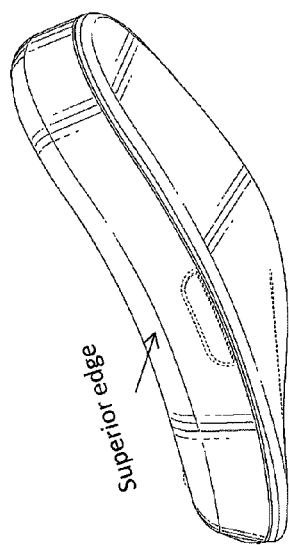
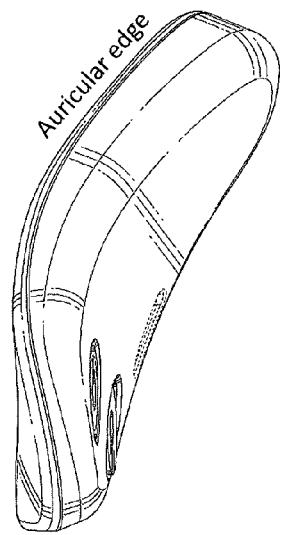
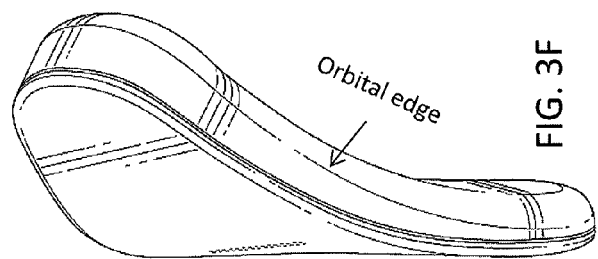
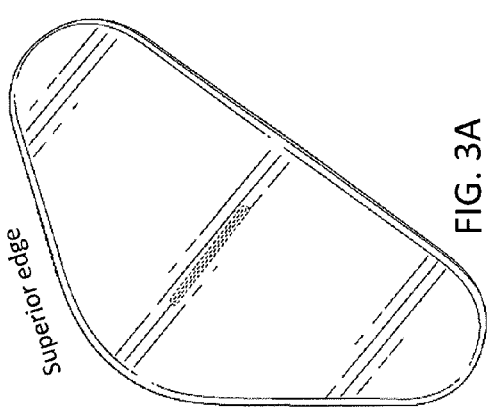
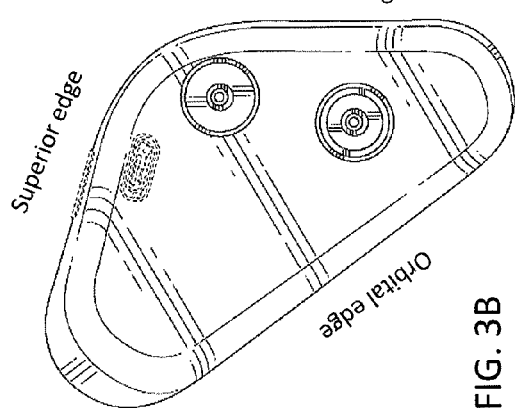

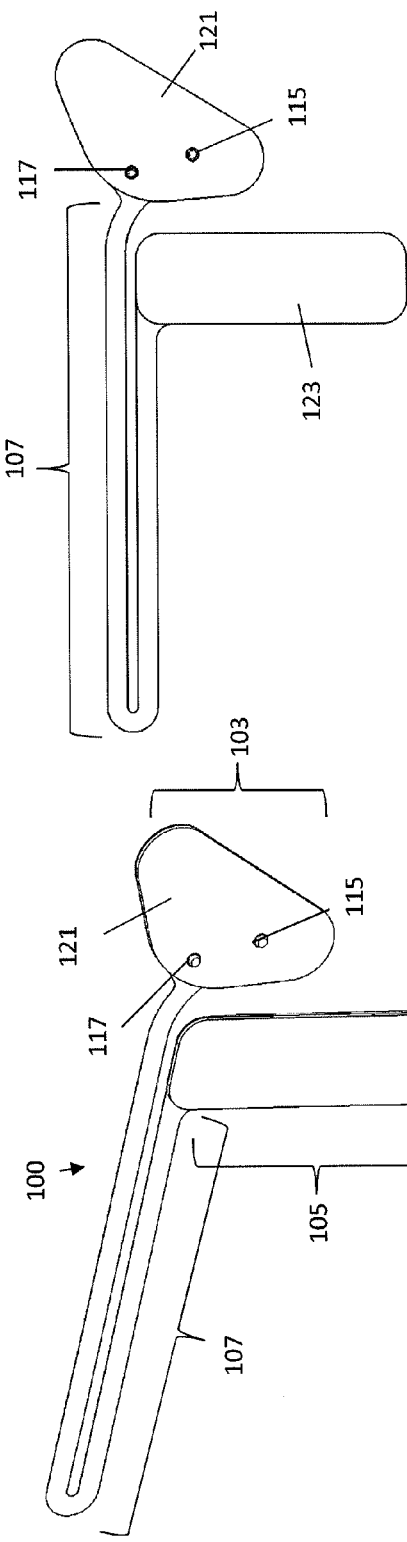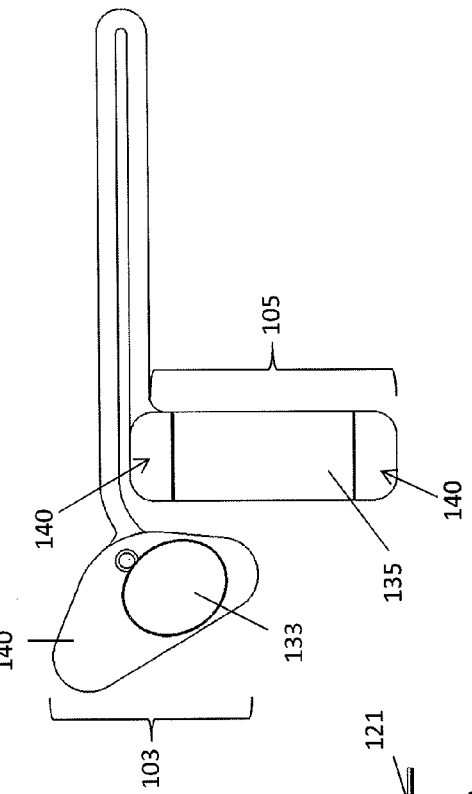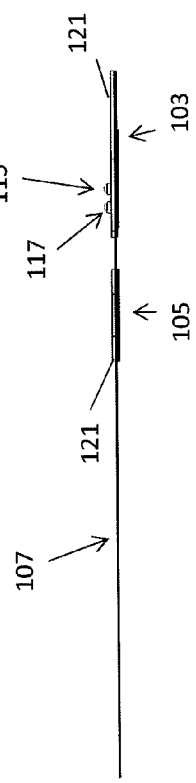

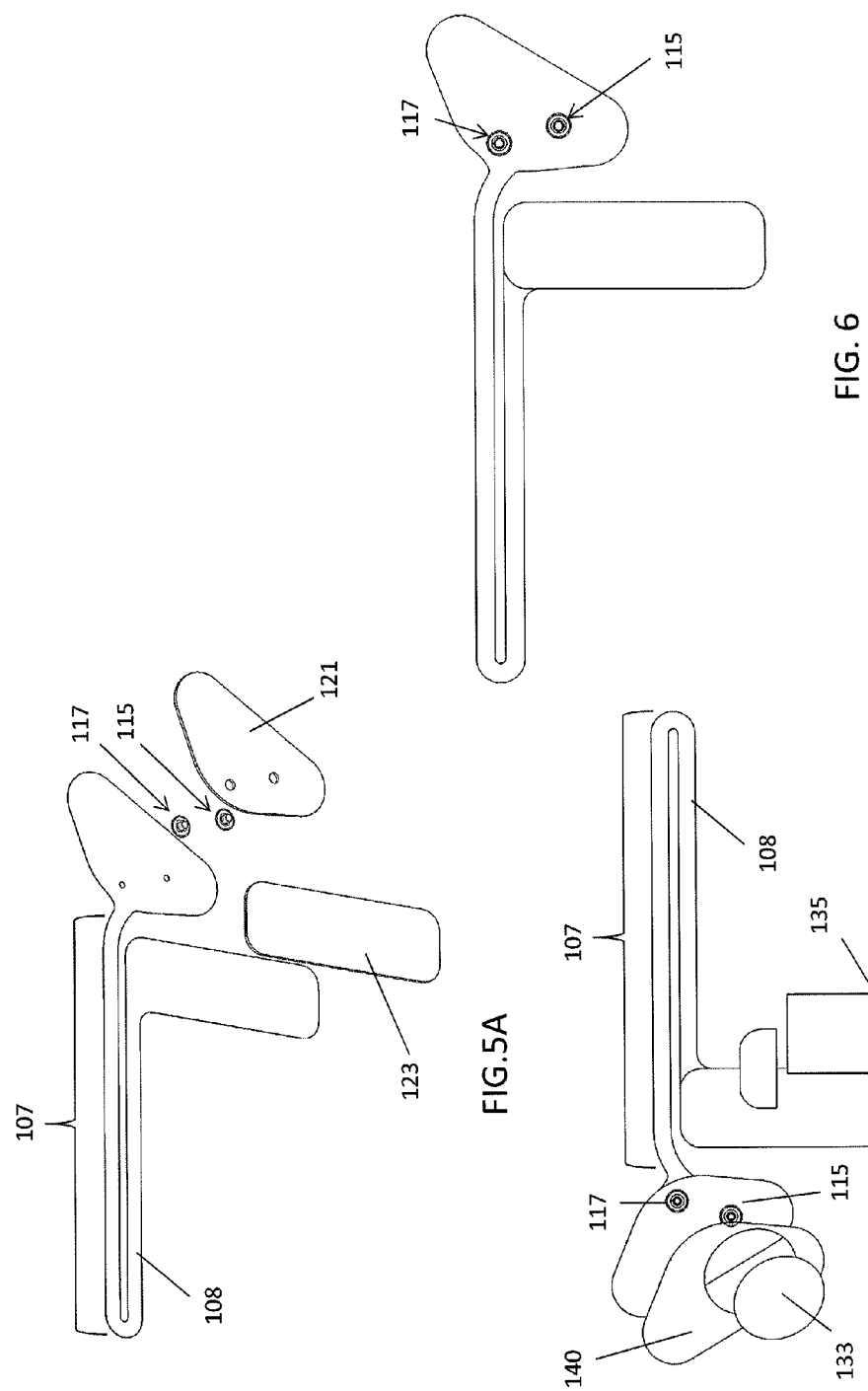

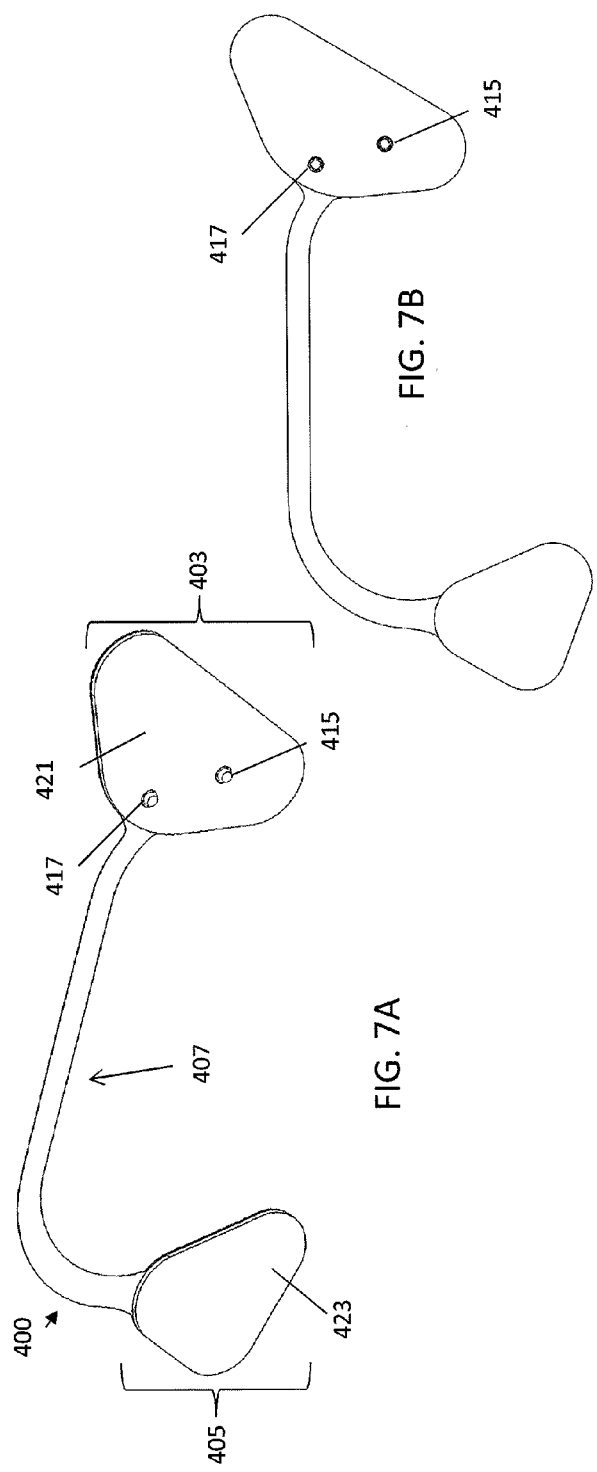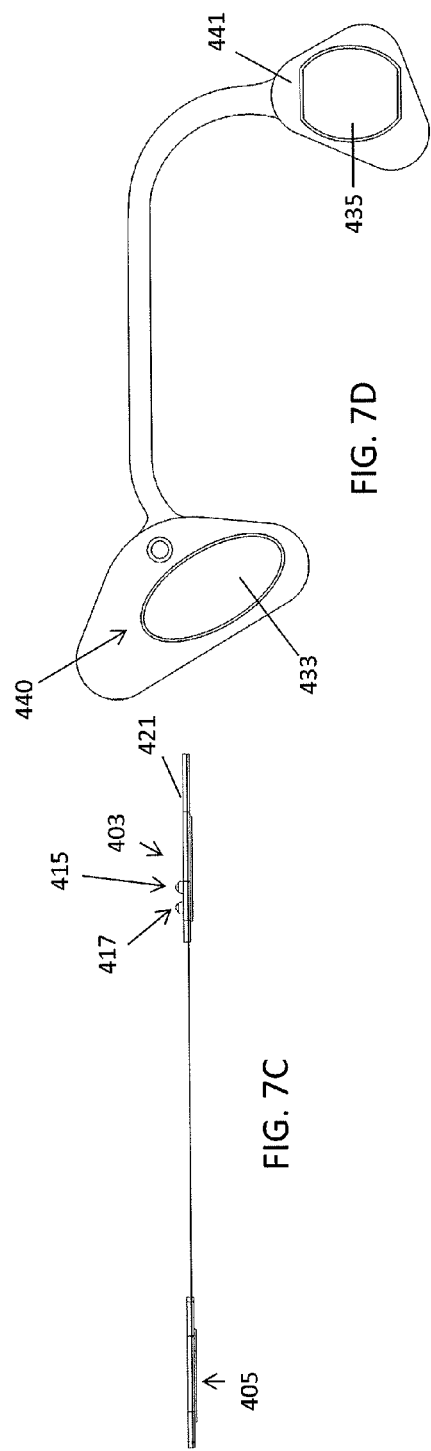

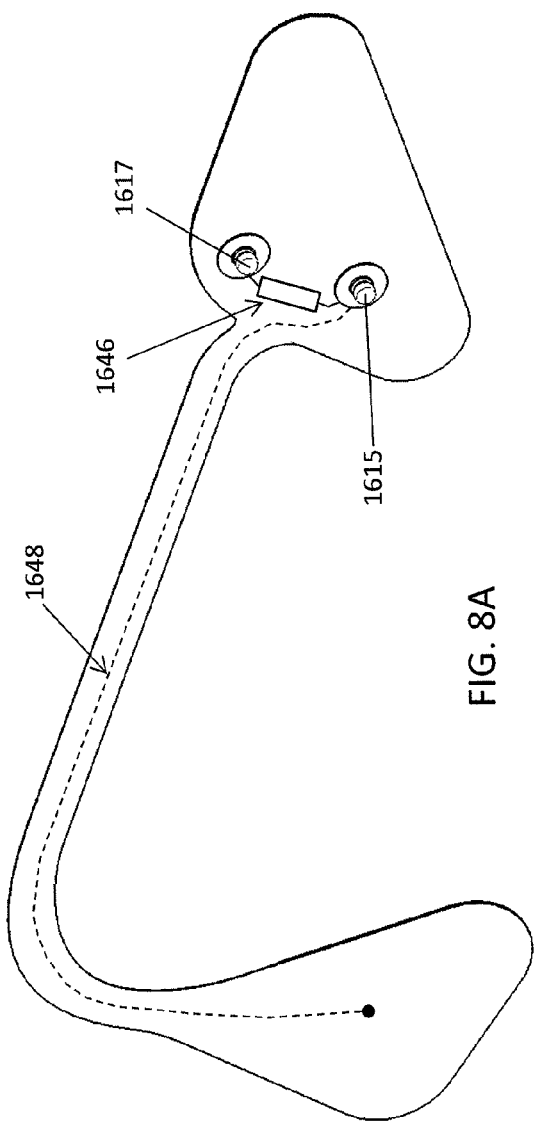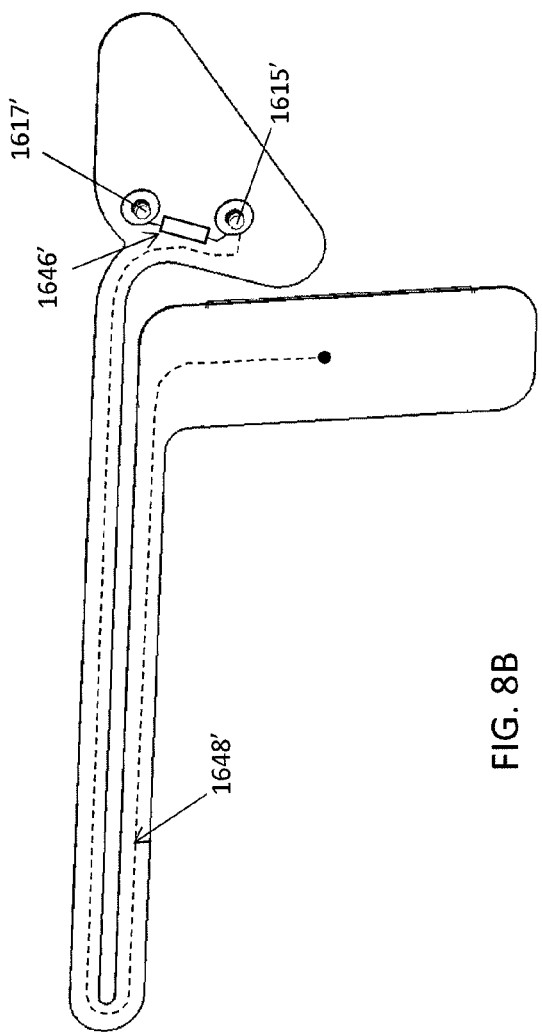

$t_n$, time spent at negative peak current
$t_p$, time spent at positive peak current
$t_c$, time for one period of cycle duty cycle = $(t_p + t_n)/t_c$

% direct current = $(t_p - t_n)/(t_p + t_n)$

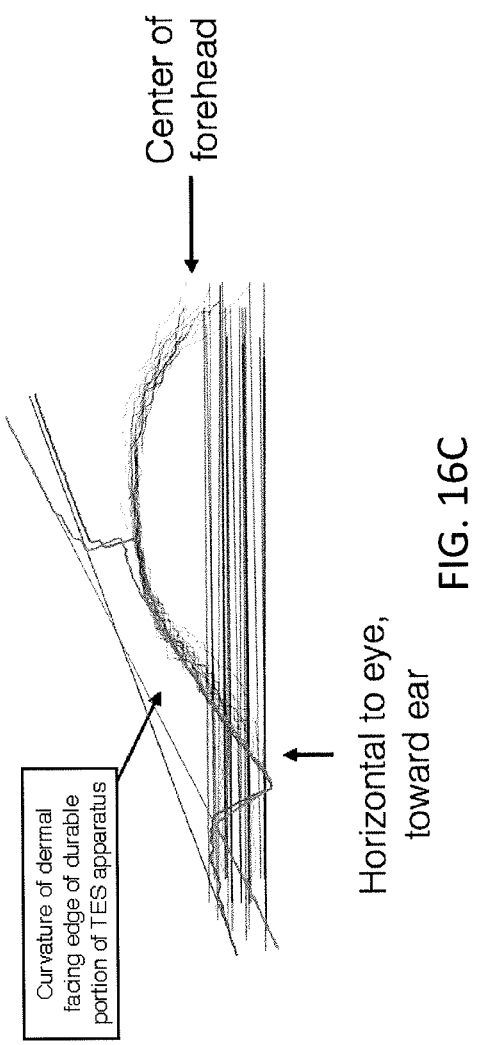

| Test # | No sticker | Sticker, No Cap. | Sticker w/ 180 pF | Sticker w/ 680 pF |
|---|---|---|---|---|
| 1 | 12000 | 22 | 264 | 408 |
| 2 | 12000 | 13 | 281 | 431 |
| 3 | 12000 | 5 | 281 | 431 |
| 4 | 12000 | 0 | 257 | 413 |
| 5 | 12000 | 6 | 260 | 424 |
| 6 | 12000 | 0 | 253 | 420 |
| 7 | 12000 | 13 | 262 | 415 |
| 8 | 12000 | 0 | 262 | 424 |
| 9 | 12000 | 18 | 261 | 416 |
| 10 | 12000 | 5 | 261 | 415 |
FIG. 20
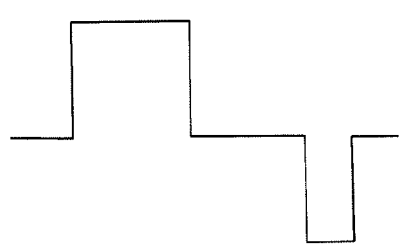
FIG. 21A
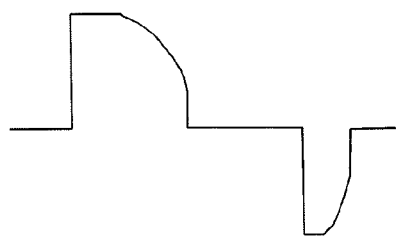
FIG. 21B
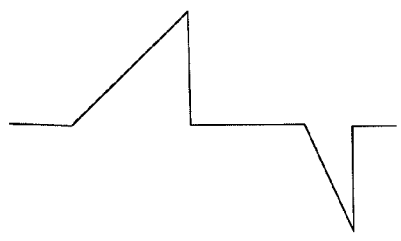
FIG. 21C
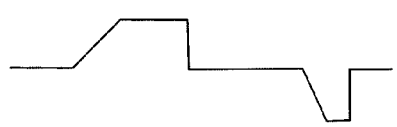
FIG. 21D

| CURRENT | | Vs saturation | |
|---|---|---|---|
| | Modulate current per waveform | Reduce current | No change |
| Overheat limit | Reduce current | Reduce current | |
| | | Max Vs reached | |

| VOLTAGE | | Vs saturation | |
|---|---|---|---|
| | Adjust Vs | No change | Adjust Vs |
| Overheat limit | Adjust Vs | No change | |
| | | Max Vs reached | |

US 9,474,891 B2

TRANSDERMAL NEUROSTIMULATOR ADAPTED TO REDUCE CAPACITIVE BUILD-UP

CROSS REFERENCE TO RELATED APPLICATIONS

This patent application claims priority to U.S. Provisional Patent Application No. 62/002,910, titled "TRANSDERMAL ELECTRICAL STIMULATION ELECTRODE DEGRADATION DETECTION SYSTEMS AND METHODS OF USING THEM," and filed May 25, 2014; U.S. Provisional Patent Application No. 62/076,459, titled "CANTILEVER ELECTRODES FOR TRANSDERMAL AND TRANSCRANIAL STIMULATION," and filed Nov. 6, 2014; U.S. Provisional Patent Application No. 62/099,950, titled "CANTILEVER ELECTRODES FOR TRANSDERMAL AND TRANSCRANIAL STIMULATION," and filed Jan. 5, 2015; U.S. Provisional Patent Application No. 62/075,896, titled "SYSTEMS AND METHODS FOR NEUROMODULATION," and filed Nov. 6, 2014; U.S. Provisional Patent Application No. 62/099,960, titled "METHODS AND APPARATUSES FOR USER CONTROL OF NEUROSTIMULATION," and filed Jan. 5, 2015; U.S. Provisional Patent Application No. 62/100,022, titled "WEARABLE TRANSDERMAL NEUROSTIMULATOR," and filed Jan. 5, 2015. Each of these applications is herein incorporated by reference in its entirety.

This patent application may also be related to the following U.S. patent applications, which are herein incorporated by reference in their entirety: U.S. patent application Ser. No. 14/558,604, titled "WEARABLE TRANSDERMAL ELECTRICAL STIMULATION DEVICES AND METHODS OF USING THEM" filed Dec. 2, 2014, Publication No. US-2015-0088224-A1; and U.S. patent application Ser. No. 14/091,121, titled "WEARABLE TRANSDERMAL ELECTRICAL STIMULATION DEVICES AND METHODS OF USING THEM", filed Nov. 26, 2013, now U.S. Pat. No. 8,903,494.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates to apparatuses (e.g., systems and devices) and methods for noninvasive neuromodulation to elicit a cognitive effect using transdermal electrical stimulation. In particular, described herein are wearable transdermal neurostimulators that may be used (and connected to) a separate electrode assembly.

BACKGROUND

Noninvasive neuromodulation technologies that affect neuronal activity can modulate neural activity and potentially alter behavior, cognitive states, perception, and motor output without requiring an invasive procedure. To date, the majority of transdermal non-invasive neuromodulatory devices apply electrical energy to a subject's skin using one or more electrodes that typically attach to the neurostimulator via a cord or cable, which can be long and awkward to wear, particularly in a non-clinical or non-research setting.

For example, transcranial/transdermal electric stimulation (hereinafter "TES") using scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Application Publication No. 2011/0144716; and Lebedev et al. U.S. Patent Application Publication No. 2009/0177243). tDCS systems with numerous electrodes and a high level of configurability have been disclosed (see for example Bikson et al. U.S. Patent Application Publication Nos. 2012/0209346, 2012/0265261, and 2012/0245653).

TES has been used therapeutically in various clinical applications, including treatment of pain, depression, epilepsy, and tinnitus. Despite the research to date on TES neuromodulation, existing systems and methods for delivering TES are lacking. In particular, neurostimulators that are effective, comfortable and easy-to-use, e.g., easy to apply and remove, particularly in a non-clinical (e.g., home) setting, have been lacking.

Although a handful of small, lightweight and presumably wearable neuromodulation devices have been described, none of these systems are adapted for use with electrodes (e.g., disposable electrode assemblies) for applying energy to a user's head. In particular, none of these systems may be secured to a separate electrode assembly so that the neurostimulator may be well-secured to the user's head (or other body region) for a variety of sizes of users. For example, previously described neurostimulators either attach directly to the user (e.g., adhesively, and must therefore rest directly against the user's body) or they are secured to an electrode which is secured to the body but requires additional support (e.g., from a strap or additional adhesive on the neurostimulator) to be worn by the subject.

Thus, there is a need for lightweight, wearable neuromodulation devices (e.g., neurostimulators) that may be securely worn by the user by attachment through a separate electrode assembly. Furthermore, there is a need for lightweight neurostimulators that mechanically and electrically secure to an electrode assembly in a manner that fits a variety of body shapes and sizes. In particular, there is a need for wearable neurostimulators that are configured to be comfortably wearable and will not fall off when a user is moving around, or even when a user is wearing additional clothing or glasses.

Moreover, during a TES session, capacitance might be built up between the electrodes, which might cause pain and discomfort. The user might be distracted, thus the cognitive effects of the TES might be reduced. Alternatively, the user might be sufficiently uncomfortable from the skin sensations of electrical stimulation that the subjective experience of pain overwhelms another cognitive, subjective, or physiological effect. Therefore, there is a need for a neurostimulator to include stimulation circuits that may reduce discomfort. For example, described herein are neurostimulators that include a "short-circuiting" feature that is configured to reduce discomfort and accordingly increase the cognitive effects induced by TES (due to one or both of: reducing the distraction of discomfort so that other cognitive effects can be experienced by a subject and permitting higher peak current intensities to be delivered that induce more significant cognitive effects).

In addition, there is a need for neurostimulator devices (and indeed, generally for electrical stimulation devices) that are both energy efficient and effective. In particular, there is a need for electrical stimulation devices (such as neurostimulators) that include a relatively high-voltage power source, yet that are capable of dynamically adjusting the power supplied to the electronics of the device so that power is conserved (and heat dissipation is minimized), while maintaining the functionality of the device.

Described herein are methods and apparatuses (e.g., devices and systems, and methods of operating such apparatuses) that may address at least the needs identified above.

SUMMARY OF THE DISCLOSURE

Described herein are neurostimulator apparatuses and methods of using them to modulate a subject's cognitive state.

In general, described herein are lightweight, wearable neurostimulator apparatuses that may be operated with an electrode assembly so that the neurostimulator apparatus may be comfortably and securely held to the user's body (e.g., head, neck, etc.) by attachment to the electrode assembly. These apparatuses may typically include one or more (e.g., two) connectors, such as mechanical and electrical connectors for releasably but securely connecting to an electrode assembly that is adapted to be worn on the user's body. The mechanical and electrical connectors may be arranged so that the device may cantilever from the electrical connector (which may therefore be referred to as a cantilevered electrode assembly) and therefore the subject's body, allowing the device to be worn by a variety of body shapes and/or sizes while still ensuring conformability of an electrode apparatus. The electrical contacts are configured to connect with electrodes. Any of these apparatuses may also include control circuitry, which may include wireless communication circuitry, current generator circuitry, one or more timers, memory, a power supply (which may be adjustable and/or rechargeable), and safety circuits. The circuitry may be programmable, dedicated, or some combination of programmable (re-programmable) and dedicated. In some variations the circuitry includes capacitive discharge circuitry that is configured to controllably apply current to one or more electrical contacts (and therefore the electrodes they are connected to) to prevent or eliminate capacitive charge. Additional circuitry may also include circuitry for regulating the power supply to prevent heat/overheating, and to prevent saturation of the power supply while meeting the power demands of an applied target neurostimulation waveform (or ensemble waveform).

The disclosure that follows describes a variety of features and embodiments, which may be described separately, including in separate sections, or jointly. One of skill in the art should understand any of the features or elements described herein may be combined with any of the other features or elements described herein. Further, although the majority of the examples described herein are specific to wearable neurostimulators, it should be understood that these features and elements may be used with any other type of stimulator, including, e.g., TENS stimulators generally, electrical stimulators generally, muscle stimulators, nerve stimulators, implantable stimulators, magnetic stimulators, ultrasound stimulators, and the like.

Also described herein are stimulators (e.g., neurostimulators) that may be worn by a user in conjunction with an electrode assembly. For example, described herein are stimulators configured to securely fit a variety of different subjects' temple regions. In some variations, these apparatuses may be configured as neurostimulators that are specifically adapted to be worn in a particular location on a subject's temple. Thus any of the variations described herein may include a user-facing surface that has a flat, twisted shape specifically configured to advantageously conform to a subject's temple.

For example, a wearable transdermal neurostimulator for inducing a cognitive effect that is configured to be comfortably worn on a subject's temple may include: a housing enclosing control circuitry, a current source comprising a power supply; a first, user-facing, surface on the housing, wherein the first surface is twisted along a twist axis wherein the first surface twists between 2 degrees and 45 degrees per 3 cm along a length of the axis of twist; and an electrode on the first surface or a connector on the first surface that is configured to connect to an electrode; wherein the neurostimulator weighs less than 5 ounces.

The electrode on the first surface or connector on the first surface may comprise one or more connectors at an edge region of the first surface, wherein the one or more connectors are configured to make an electrical and mechanical connection with a mating surface of an electrode apparatus comprising one or more electrodes.

In general, the apparatuses described herein may be lightweight. For example, the neurostimulator may weigh less than 7 ounces (e.g., less than 7 ounces, 6 ounces, 5 ounces, 4 ounces, 3 ounces, 2 ounces).

The neurostimulator housing may be less than 30 mm thick, and may have a non-uniform thickness. For example, the neurostimulator housing may comprise an outward-facing surface opposite from the first surface, and wherein the thickness of the housing between the outward-facing surface and first surface is more than 15% greater (more than 20%, more than 25%, more than 30%, more than 35%, etc.) at one end of the neurostimulator than at an opposite end of the neurostimulator.

These apparatuses may generally connect to one or more electrode apparatuses (e.g., an adhesive electrode) through one or more connectors on the apparatus that may connect (mechanically and/or electrically) with one or more complimentary connectors on the electrode assembly. The connectors on the apparatus may be on the body of the apparatus and may comprise a pair of mechanical and electrical connectors. The one or more connectors may comprise a pair of sockets configured to receive posts, snaps, projections, etc., from the electrode assembly, or the electrode assembly may have sockets configured to couple to connectors on/projecting proud of the apparatus which may be snaps, posts, projections, etc.

As will be described in greater detail below, apparatuses having two connectors (e.g., sockets, etc.) for connecting to an electrode apparatus may be particularly useful. In particular, described herein are apparatuses having a pair of connectors positioned at a predetermined location relative to each other (and off-center on a user-facing surface of the apparatus). The positioning and/or spacing may be optimized for securing the apparatus to the electrode assembly, maintaining a secure attachment, while allowing the apparatus to fit to a variety of body shapes and sizes, and in some cases, allowing the apparatus to cantilever relative to the electrode assembly worn against the user's body (and therefore to cantilever relative to the user's body). For example, an apparatus may include a pair of connectors separated from each other by between about 0.5 inches and 1.0 inches (more optimally, between 0.6 and 0.9, between 0.7 and 0.8, etc.). This separation may be center-to-center or nearest-edge to nearest-edge.

In general, any of the housings described herein may be approximately triangular in shape. Approximately triangular shapes include trianguloid shapes, which may have three edges (which may be curved or straight) and may generally have three corner regions, which may be sharp or curved (e.g., rounded edges).

The housing may include a lower user-facing surface (which may typically but not necessarily include the one or more connectors). The housing may also include an upper surface, approximately opposite (or generally opposite) from the lower surface. The distance between the upper and lower surfaces may be the thickness of the apparatus. In general, the thickness may be constant or may vary across the apparatus.

As mentioned, the lower (user-facing) surface may be concave and/or twisted along a twist axis wherein the first surface twists between 2 degrees and 45 degrees per 3 cm along a length of the axis of twist (e.g., between 1 degree and 45 degrees, between 2 degrees and 40 degrees, between any of a lower boundary selected from: 2°, 3°, 4°, 5°, 6°, 7°, 8°, 9°, 10° and any of an upper boundary selected from: 10°, 15°, 20°, 25°, 30°, 35°, 40°, 45°, where the lower boundary is always less than the upper boundary). This may also be expressed as between about 0.07 degrees/mm and about 1.5 degrees/mm).

Functionally, any of the neurostimulator apparatuses described herein may be configured to deliver a transdermal electrical stimulus. In particular, the apparatuses may include control circuitry including a current source that may include a power supply and a waveform generator, configured to deliver a biphasic current of up to 35 mA between about 750 Hz and 30 kHz that is asymmetric. The neurostimulator current source may generally comprise a high-voltage power supply configured to supply a voltage between about 10 and 100 V. This power supply may be adjustable so that the available voltage (voltage source) provided by the power supply may be adjusted by voltage control circuitry which may receive feedback from the electrical connectors connected to the electrodes and/or directly from the electrodes.

Also described herein are methods of modulating a subject's cognitive state with a wearable transdermal neurostimulator (including any of the neurostimulators described herein). For example, a neurostimulator having a housing comprising a first concave user-facing surface, a second outward-facing surface opposite the user-facing surface and thickness there between, wherein the housing is bounded between the first and second surfaces by a superior edge, an auricular edge and an orbital edge, and wherein the thickness of a region of the housing near an intersection of the auricular edge and the orbital edge is less than 2 cm thick, may be used to modulate a subject's cognitive state. A method of modulating a cognitive state using such an apparatus may include: attaching the neurostimulator to the subject's temple region with the orbital edge extending facing the subject's eye orbit region and the auricular edge facing the subject's ear and the superior edge facing a top of the subject's head (and/or temple region).

For example, a method of modulating a subject's cognitive state with a wearable transdermal neurostimulator, wherein the neurostimulator has a housing comprising a first concave user-facing surface that is approximately triangular, a second outward-facing surface opposite the user-facing surface and thickness there between, wherein the housing is bounded between the first and second surfaces by a superior edge, an auricular edge and an orbital edge, and wherein the thickness of a region of the housing near an intersection of the auricular edge and the orbital edge is at least 15% thinner than the thickness of a region of the housing near an intersection of the superior edge and the orbital edge, may include: attaching the neurostimulator to the subject's temple region with the orbital edge extending facing the subject's eye orbit region and the auricular edge facing the subject's ear and the superior edge facing a top of the subject's head.

In any of these variations, the method may include attaching an electrode assembly to the subject's temple and coupling the user-facing surface of the neurostimulator to an outward-facing surface of the electrode assembly. The method may include adhesively attaching an electrode assembly to the subject's temple and coupling the user-facing surface of the neurostimulator to an outward-facing surface of the electrode assembly by at least one electrical and mechanical attachment.

Any of these methods may include attaching a first electrode portion of an electrode assembly to the subject's temple and a second electrode portion of an electrode assembly to a second region on the subject's head or neck and coupling the user-facing surface of the neurostimulator to an outward-facing surface opposite from the first electrode portion of the electrode assembly so that the neurostimulator is in electrical contact with both the first and second electrode portions of the electrode assembly.

Any of these methods may include wearing glasses or other jewelry or garments over at least a portion of the neurostimulator.

Also described herein are neurostimulators that include capacitive discharge during some or all of the delivered pulses forming the waveforms (e.g., ensemble waveforms). For example, a wearable transdermal neurostimulator for inducing a cognitive in a subject, the neurostimulator may include: a housing enclosing a controller, a wireless communication sub-system connected to the controller, and a high-voltage power supply; a first, user-facing, surface on the housing; a first connector configured to connect with a first electrode an a second connector configured to connect with a second electrode; and wherein the controller comprises a waveform generator configured to deliver a biphasic electrical signal between the first electrode and the second electrode, and a capacitive discharge circuit, wherein the controller is configured to trigger the capacitive discharge circuit to discharge a capacitance on the first electrode and the second electrode during the delivery of the biphasic electrical stimulation signal. In any of the apparatuses and methods described herein, the discharge circuit may be configured so that a capacitive discharge current may be applied in a single direction (e.g., to one or the other electrodes), separately or individually, including without applying a capacitive discharge current in both directions (e.g., to both electrodes, anode and cathode).

Examples of capacitive discharge circuits are provided herein, but in some variations may include a double H-Bridge circuit. The neurostimulator controller may include a switch configured to turn off the current source when the capacitive discharge circuit is triggered. The neurostimulator capacitive discharge circuit may be configured to discharge a capacitance for a duration between 0 and 100 microseconds. The neurostimulator controller may include an amplifier configured to measure a voltage delivered to the first electrode and the second electrode during an electrical stimulation pulse.

The neurostimulator controller may be configured to adjust the voltage provided by the high-voltage power supply to the waveform generator based on a historical demand of the applied voltage estimated from a plurality of earlier cycles.

Also described are neurostimulators that are configured to detect (using detection circuitry or capacitive detection circuitry) the connection to an electrode assembly having a capacitive element between the electrodes (e.g., between the connectors to the electrodes); the capacitive element may act as a high-frequency (high pass) filter, which is only detectable at frequencies above a threshold (e.g., above 50 kHz) but otherwise acts as an open circuit. These neurostimulators may also detect a resonance of the capacitive element which may be used to both confirm connection and to identify the type or class of electrode assembly attached. For example, a wearable transdermal neurostimulator for inducing a cognitive effect in a subject, wherein the neurostimulator is configured to couple with an electrode assembly worn by the subject, may include: a housing enclosing a controller, a wireless communication sub-system connected to the controller, and a high-voltage power supply; a first, user-facing, surface on the housing; a first connector configured to connect with a first electrode and a second connector configured to connect with a second electrode; and wherein the controller comprises a waveform generator configured to deliver a biphasic electrical signal between the first electrode and the second electrode, and a capacitive sensing circuit, wherein the controller is configured to detect a capacitance signal between the first and second electrodes indicating that the electrodes have been connected, and further configured to detect a characteristic resonance.

Any of the neurostimulator apparatuses described herein may be configured to cantilever, e.g., to be securely connected at one region of the user-facing surface, but free to float relative to the user and/or electrode apparatus attached/attachable to the subject at an opposite end. This may generally be achieved by positioning two (or potentially more) mechanical and/or electrical connector(s) between the adhesive electrode apparatus and the neurostimulator apparatus off-center, with a predetermined spacing between the two. For example, a transdermal neurostimulator that is connectable to a subject via attachment with an electrode apparatus may include: a housing enclosing a controller and a current source, wherein the housing comprises a concave user-facing surface and a top surface opposite the user-facing surface; a first edge region and a second edge region between the user-facing concave surface and the top surface, wherein the first edge region is thinner than the second edge region; a first and second connector on the user-facing concave surface and off-center relative to the user-facing concave surface, wherein the first and second connectors are each configured to make an electrical and mechanical connection with a connector mate on an electrode apparatus, further wherein the first and second connectors are separated by between 0.7 and 0.8 inches.

A wearable transdermal neurostimulator that is connectable to a subject via a cantilevered attachment with an electrode apparatus may include: a housing enclosing control circuitry and a current source; a user-facing first surface on the housing, wherein the first surface is concave and twisted; and one or more connectors on the first surface and off-center relative to the first surface, wherein the one or more connectors is configured to make an electrical and mechanical connection with a connector mate on a mating surface of the electrode apparatus; wherein the neurostimulator weighs less than 5 ounces.

Any of the stimulation devices described herein (e.g., neurostimulators) may include two connectors (e.g., the one or more connectors comprise a first and a second connector). As used herein, a connector may be an electrical and mechanical connector that may both make electrical contact and may mechanically secure the stimulation device to the electrode apparatus (e.g., an electrode assembly). A connector may be a male (protruding) connector that inserts into a female (receiver) connector, a female connector (receiver) that receives a male (protruding) connector, a grasping (clamping) connector that mates with a graspable connector (knob, etc.), or any other type of connector. For example, connectors may be snaps, clasps, plugs, magnets, or the like. A stimulation device may include a pair of (or more) connectors that are both the same type (e.g., snaps or snap receivers) or different types (e.g., snaps and snap receivers). For example, in a variation having a first and second connectors on the neurostimulator apparatus (e.g., on a user-facing surface of the neurostimulator apparatus), the connectors may comprise snap receivers (e.g., configured to receive a male snap post).

Any of the neurostimulator apparatuses described herein may be configured as cantilevered attachments, so that the connectors on the apparatus (e.g., first and second connectors) secure an edge region of the user-facing concave surface to the electrode apparatus (electrode assembly) while permitting an end of the user-facing concave surface opposite from the edge region to move relative to the electrode apparatus. The separation between the connectors on the neurostimulator apparatuses (e.g., with between about 0.7 and 0.8 inches between the two) is particularly well suited to this configuration, and especially when the apparatus is less than 5 inches in diameter and/or less than 0.5 inches thick, on average), although this arrangement may work with neurostimulator apparatuses having different dimensions as well.

For example, in some variations, the first and second connectors are separated by between about 0.7 and 0.75 inches, or between about 0.72 and about 0.74 inches, etc.

In some variations, an adaptor unit may couple to the first and second connectors and provide a second set of electrode connectors with a larger separation between them than the inter-connector distance on the neurostimulator unit (e.g. greater than 0.8 inches, greater than 1 inch, etc.).

As mentioned, in general these devices are lightweight, and in particular, the apparatus may weigh less than 5 ounces. The weight may be non-uniformly distributed within the apparatus; in particular in neurostimulator apparatuses configured to cantilever off of an electrode apparatus, the weight (and/or thickness) of the neurostimulator apparatus may be greater at or near the end of the neurostimulator apparatus above the connectors, so that the lighter end (which may also be thinner) is opposite this end/edge region. Counterintuitively, in some variations this may be reversed, so that the thicker and/or heavier end/edge region of the neurostimulator apparatus is positioned opposite from the region of electrical and mechanical attachment by the connectors; this configuration may be unexpectedly advantageous in allowing the device to conform to the subject's head while remaining securely attached to the electrode apparatus. This configuration may also allow separation between the connectors (e.g., snap receivers) and internal electrical circuitry and/or power storage (e.g., battery) components.

Any of the devices described herein may be generally fairly thin. For example, the housing of any of the neurostimulator apparatuses described herein may be less than 30 mm thick (e.g., less than 20 mm thick, less than 15 mm thick, less than 14 mm thick, less than 13 mm thick, less than 12 mm thick, less than 11 mm thick, less than 10 mm thick, less than 9 mm thick, less than 8 mm thick, less than 7 mm thick, less than 6 mm thick, less than 5 mm thick, etc.). This may refer to average or absolute (maximum) thickness of the housing. In general, these devices may have a uniform or non-uniform thickness, as mentioned above. As mentioned above, in any of these variations, the housing of any of these wearable electrical stimulators may have a top surface opposite from the first (e.g., user-facing or electrode assembly-facing) surface that is more than 10% (or 15%, or 20%, or 25% or 30%, or 35%, or 40% or 45% or 50%, or 60%, or 70%, or 80%, or 90%, or 100%, or 110%, etc.) greater at one end region of the neurostimulator than at an opposite end of the neurostimulator.

In some variations, the housing of the neurostimulator apparatuses is trianguloid. As mentioned above, this may refer to the roughly three-sided shape (looking down on the neurostimulator apparatuses housing) of the housing when the device is attached to an electrode assembly. The sides may be curved or straight, as may the corners of the trianguloid outer perimeter.

The user-facing surface may be flat, or in some variations it may be twisted and/or concave. As described above, the user-facing surface may be concave and twisted along a twist axis wherein the first surface twists between 2 degrees and 45 degrees per 3 cm along a length of the twist axis.

Any of the neurostimulator apparatuses described herein may be adapted for use to deliver TES through the attached (or in some variations, integrated) electrode apparatuses to modify a subject's cognitive state. For example, any of these devices may be specifically configured to provide stimulation through the connectors to a pair of electrodes to apply electrical stimulation as described in U.S. patent application Ser. No. 14/639,015, titled "TRANSDERMAL ELECTRICAL STIMULATION DEVICES FOR MODIFYING OR INDUCING COGNITIVE STATE," filed Mar. 4, 2015 (which claims priority to U.S. Pat. No. 9,002,458). In some variations, the neurostimulator includes a controller within the housing that is configured to deliver pulsed, asymmetric, biphasic current greater than 3 mA between about 750 Hz and 30 kHz between the connectors so that this energy may be applied through connected (or integrated) electrodes.

In particular, the neurostimulator apparatuses described herein may include hardware and/or software and/or firmware (e.g., circuitry, programmable processors, memory, etc.) that enable the relatively high-current, high-frequency stimulation that is particularly effective for modifying a cognitive state when applied in the proper location on a user's head and/or neck. Thus, the housing may enclose (partially or completely) one or more processors, circuit boards, circuitry (including any of the circuits or sub-systems described herein), comparators, amplifiers (e.g., op-amps, etc.), capacitors, resistors, transformers, inductive coils, LEDs, batteries, or the like. In particular, any of the neurostimulator apparatuses described herein may include a current source (e.g., current supply circuitry) and/or may include a high-voltage power supply configured to supply a voltage between about 10 and 100 V, which may be particularly helpful for achieving the target stimulation parameters for modulating a cognitive state by TES.

Any of the neurostimulator apparatuses described herein may also be generally configured for wireless communication, e.g., with a remote or local device providing instructions (including waveforms to be delivered from the neurostimulator apparatuses), and thus any of these apparatuses may include a wireless sub-system (e.g., Bluetooth chipset and antenna, etc.) within the housing and connected to the controller.

Also described herein are methods of modulating a subject's cognitive state with a wearable transdermal neurostimulator. For example in some variations the method may include using any of the neurostimulator apparatuses described herein. For example, a method may include: making an electrical and mechanical connection between a first and second connector on a first surface of a housing of the wearable transdermal neurostimulator and a first and second connector mate on an electrode apparatus, wherein the first and second connectors are separated by between 0.7 and 0.8 inches and wherein the housing comprises the first surface and a second surface opposite the first surface, and a first edge region and a second edge region between the first surface and the second surface, wherein the first edge region is thinner than the second edge region; securing the electrode apparatus to the subject's temple or forehead; and applying electrical stimulation from the electrode apparatus by delivering pulsed, asymmetric, biphasic current. Applying electrical stimulation may include delivering pulsed, asymmetric, biphasic current of greater than 3 mA that is between about 750 Hz and 30 kHz.

Another example of a method of modulating a subject's cognitive state with a wearable transdermal neurostimulator includes: making an electrical and mechanical connection between one or more connectors on a first surface of the wearable transdermal neurostimulator and one or more connector mates on an electrode apparatus, wherein the first surface is concave and twisted along a twist axis so that the first surface twists between 2 degrees and 45 degrees per 3 cm along a length of the twist axis and wherein the one or more connectors are located off-center relative to a first surface; attaching the electrode apparatus to the subject's temple or forehead; and applying electrical stimulation from the electrode apparatus by delivering pulsed, asymmetric, biphasic current.

In general, making electrical and mechanical connection comprises snapping the first connector mate into the first connector and the second connector mate into the second connector. Making the electrical and mechanical connection may include connecting the first and second connector on the first surface of the housing to the first and second connector mates on the electrode apparatus; the first surface may be concave.

Securing the electrode apparatus to the subject's temple or forehead may include adhesively securing the electrode apparatus to the subject's temple or forehead.

Any of these methods may also include making the electrical and mechanical connection between the electrode apparatus and the neurostimulator before attaching the neurostimulator to the subject's temple or forehead. For example, the method may include connecting a portion of the electrode apparatus to the subject's neck or mastoid region, and another portion (to which the neuromodulation apparatus may connect) to the subject's temple and/or forehead region.

As mentioned above, the apparatuses described herein may be worn with garments, jewelry and/or prosthetics, including, e.g., glasses, hearing aids, hats, etc., typically without interfering with the comfort, position, and function of these garments, jewelry and/or prosthetics. For example, a method of applying, using or wearing the apparatuses described herein may include wearing glasses over at least a portion of the neurostimulator.

Application of the apparatuses described herein may include initially determining where to apply the apparatus (e.g., the combined neuromodulation apparatus and the electrode assembly, which may be first connected together using the connectors as described herein). For example, any of these methods may include 'testing' the position of the apparatus and electrode assembly on the head before adhesively securing the device onto the head and/or neck. For example, a method of modulating a subject's cognitive state with a wearable transdermal neurostimulator device may include: positioning a concave surface of the neurostimulator device over a subject's forehead or temple region in a first position; removing a backing layer from an adhesive on the concave surface of the neurostimulator device; and repositioning the concave surface of the neurostimulator device in approximately the first position to adhesively secure the neurostimulator device to the subject's forehead or temple region.

Any of the methods described herein may include applying electrical stimulation from the electrode apparatus by delivering pulsed, asymmetric, biphasic current of between about 3 mA to 25 mA that is between about 750 Hz and 30 kHz.

In general, any of these methods may include removing the neurostimulator device from the user's head in a 'testing' position before removing the backing layer, e.g. to expose the adhesive so that it can be applied in the desired location. A mirror or an application (e.g., smartphone, tablet, etc. application/software) that can display a real-time image of the user via a front-facing camera may be used when applying the apparatus to confirm the location of the apparatus. For example, the method may include displaying a mirror image of the subject's head and/or comprising capturing an image of the subject's head after positioning the concave surface of the neurostimulator device and displaying the image while repositioning the neurostimulator device. In some variations an actual mirror may be used to display the user's image; in some variations a front-facing camera may be used, as described above.

A neurostimulator apparatus may be connected to (and may include a step of connecting) an electrode assembly having an adhesive covered by the backing layer. In some variations the electrode assembly and neurostimulator apparatus are coupled together before adhesively applying the device to the user. In some variations, the electrode assembly may be attached to the user's body first partially or completely, before coupling the neurostimulator apparatus to the electrode assembly.

In methods in which the neurostimulator apparatus and electrode apparatus are applied on the users head and/or neck, positioning the concave surface may include shifting the neurostimulator device to identify a conformable position of the shape to the subject's forehead or temple region (e.g., before adhesively securing the two to the user's head). Positioning the concave surface may include shifting the neurostimulator device relative to one or more of the subject's: eyebrow, eye, hairline, or midline of forehead.

As mentioned above, any of the apparatuses described herein may include a high-voltage power supply; these power supplies may be adjustable by the apparatus during operation, so that the available voltage supplied by the power supply (supply voltage, $V_s$) is controlled and variable. As mentioned above, this adjustment may allow the apparatus to prevent overheating and conserve power, as well as prevent the circuitry (e.g., the current source) from saturating during an electrical stimulation pulse. This adjustment may be dynamic. For example, also described herein are transdermal neurostimulator apparatuses (e.g., devices) that include: a housing enclosing a high-voltage power supply having a maximum voltage of greater than 10V and further configured to provide a supply voltage of less than the maximum voltage, wherein the supply voltage is adjustable; a first connector configured to electrically connect with a first electrode and a second connector configured to electrically connect with a second electrode; and a controller within the housing, the controller comprising: a waveform generator configured to deliver a pulsed, asymmetric, biphasic electrical signal between the first and the second connectors, wherein the waveform generator receives the supply voltage from the high-voltage power supply, and wherein the controller is configured to compare a difference between the supply voltage and an applied voltage between the first and second connectors to a target voltage offset, and further wherein the controller is configured to adjust the supply voltage based on the comparison.

In any of these variations of transdermal neurostimulator apparatuses described herein, the apparatus may include: a housing enclosing a high-voltage power supply having maximum voltage of greater than 10V and further configured to provide a supply voltage of less than the maximum voltage, wherein the supply voltage is adjustable; a first connector configured to electrically connect with a first electrode and a second connector configured to electrically connect with a second electrode; and a controller within the housing, the controller comprising: a waveform generator configured to deliver a pulsed, asymmetric, biphasic electrical signal between the first and the second connectors, wherein the waveform generator receives the supply voltage from the high-voltage power supply, and a sensing circuit configured to detect an applied voltage between the first and second connectors, wherein the controller is configured to compare a difference between the supply voltage and the applied voltage with a target voltage offset, and to adjust the supply voltage by decreasing the supply voltage if the difference between the supply voltage and the applied voltage is greater than the target voltage offset and to adjust the supply voltage by increasing the supply voltage if the difference between the supply voltage and the applied voltage is less than the target voltage offset.

In any of these examples, the high-voltage power supply may be configured to provide supply voltages between a generally high-voltage range (e.g., greater than 20 V, between 10V and 120V, between 20V and 100V, etc.).

The target voltage offset may generally be a threshold value (e.g., 2V, 3V, 4V, 5V, 6V, 7V, etc.) or a voltage range (e.g., between about 2V-10V, between about 3V-9V, between about 4V-8V, between about 5V-7V, between about 4V-10V, between any one of about 1V, 2V, 3V, 4V, 5V, 6V, etc., and about 8V, 9V, 10V, 11V, 12V, etc.).

The adjustment of the voltage may be regulated by a regulator and/or controller (e.g., control/regulator circuitry or sub-system) that may be generally configured to decrease the supply voltage if the difference between the supply voltage and the applied voltage is above the target voltage offset and to increase the supply voltage if the difference between the supply voltage and the applied voltage is below the target voltage offset. The controller may be configured to adjust the supply voltage as a function of the difference between the supply voltage and the applied voltage.

In general, the apparatus may include a sensing circuit. The sensing circuit may include an amplifier connected to one or both of the first and second connectors (e.g., to measure the voltage difference between the two, $V_{applied}$, which may be applied to the user).

The controller may be configured to determine if the device is in an overheating state based on an applied current and the difference between the supply voltage and the applied voltage. In some variations, the controller is configured to determine if the apparatus is in a saturation state (e.g., if the currently supply sub-system/circuitry is saturated). In general, the regulator circuitry or sub-system may also include a temperature sensor (e.g. thermistor) for determining the overheating condition.

Also described herein are methods of operating a neurostimulation device to dynamically adjust the available voltage supplied by a power supply. For example, a method of regulating the power of a wearable transdermal neurostimulator device may include: delivering a biphasic electrical signal between a first electrode and a second electrode of the transdermal neurostimulator device, wherein the transdermal neurostimulator device comprises a high-voltage power supply providing an adjustable supply voltage and a waveform generator receiving the supply voltage; detecting an applied voltage between the first electrode and the second electrode; and comparing a difference between the supply voltage and the applied voltage to a target voltage offset, and adjusting the supply voltage by: increasing the supply voltage if the difference between the supply voltage and the applied voltage is below the target voltage offset, or decreasing the supply voltage if the difference between the supply voltage and the applied voltage is above the target voltage offset.

Detecting the applied voltage may include detecting the applied voltage at a first connector connected to the first electrode and a second connector connected to the second electrode. In general, detecting the applied voltage may occur during one or more pulses of a TES waveform and may avoid measurements of applied voltage between pulses (open circuit condition) or during periods of a TES waveform when a capacitive discharge occurs. Measuring during a pulsing period of a TES waveform may include detecting a gating or other digital or analog signal generated by a controller of the neurostimulation device that identifies active pulse periods distinct from open circuit and capacitive discharge periods.

The target voltage offset may be a range of voltages (e.g., between about 2 V and 10 V, between about 3 V and 9 V, between about 4 V and about 8 V, between 6 V and 7 V, etc.).

Any of the neurostimulator apparatuses described herein may be configured as cantilevered devices for use with an electrode assembly, as described above. For example, a neurostimulator apparatus may be a wearable transdermal neurostimulator that is connectable to a subject with an electrode apparatus and may include: a housing enclosing a controller and a current source; a concave user-facing surface on the housing; and a first and second connector on the user-facing concave surface and off-center relative to the user-facing concave surface, wherein the first and second connectors are each configured to make an electrical and mechanical connection with a connector mate on an electrode apparatus, further wherein the first and second connectors are separated by between 0.7 and 0.8 inches.

The first and second connectors may secure a first edge region of the user-facing surface to the electrode apparatus while permitting a second edge region of the user-facing surface that is opposite from the first edge region to float relative to the electrode apparatus. As discussed above, the first and second connectors may comprise snap receivers. The first and second connectors may be separated by any appropriate length, typically between 0.5 and 1 inch, but particularly 0.6 and 0.9 inches and more particularly 0.7 and 0.8 inches (e.g., between about 0.7 and 0.75 inches). As described above, such cantilevered apparatuses may be lightweight (e.g., may weigh less than 5 ounces), and may be relatively thin (e.g., the housing may be less than 30 mm thick, less than 20 mm thick, less than 15 mm thick, less than 11 mm thick, etc.).

The housing may include a top surface opposite from the user-facing surface, and the thickness of the housing between the outward-facing surface and first surface may be more than 15% greater at one end of the neurostimulator than at an opposite end of the neurostimulator. The user-facing surface may be concave and/or twisted. For example, the user-facing surface may be concave and twisted along a twist axis wherein the user-facing surface twists between 2 degrees and 45 degrees per 3 cm along a length of the twist axis.

The controller may be configured to deliver pulsed, asymmetric, biphasic current greater than 3 mA between about 750 Hz and 30 kHz.

A wearable transdermal neurostimulator that is connectable to a subject with an electrode apparatus may include: a housing enclosing a controller and a current source; a user-facing first surface on the housing, wherein the first surface is concave; and a first and second connector on the first surface and off-center relative to the first surface, wherein the first and second connectors are configured to make an electrical and mechanical connection with a connector mate on a mating surface of the electrode apparatus when the electrode apparatus is attached to a subject's head with the mating surface facing away from the subject's head so that the first and second connectors secure one side of the first surface to the mating surface of the electrode apparatus while permitting an opposite side of the first surface to float relative to the mating surface. The first and second connectors are separated from each other by between about 0.7 inches and 0.8 inches.

In any of the apparatuses described herein, the first and second connectors may comprise a pair of sockets configured to receive snaps from the electrode assembly. The neurostimulator may weigh less than 5 ounces. The housing may include an outward-facing surface opposite from the first surface, wherein the thickness of the housing between the outward-facing surface and first surface may be more than 15% greater at one end of the neurostimulator than at an opposite end of the neurostimulator. The first surface may be concave and twisted along a twist axis wherein the first surface twists between 2 degrees and 45 degrees per 3 cm along a length of the twist axis.

The controller may be configured to deliver pulsed, asymmetric, biphasic current greater than 3 mA between about 750 Hz and 30 kHz.

Also described herein are methods of attaching a neurostimulation apparatus to a user so that one end is cantilevered relative to an electrode assembly (and thus the user's body), such as methods of modulating a subject's cognitive state with a wearable transdermal neurostimulator. Any of these methods may include: making an electrical and mechanical connection between a first and second connector located off-center on a first surface of a housing of the wearable transdermal neurostimulator with a first and second connector mate on an electrode apparatus, wherein the first and second connectors are separated from each other on the first surface by between 0.7 and 0.8 inches; securing the electrode apparatus to the subject's temple or forehead; and applying electrical stimulation from the electrode apparatus by delivering an asymmetric, pulsed, biphasic current.

For example, applying electrical stimulation may include delivering pulsed, asymmetric, biphasic current of greater than 3 mA that is between about 750 Hz and 30 kHz. Making the electrical and mechanical connection may comprise snapping the first connector of the electrode apparatus into the first connector mate of the neurostimulator and the second connector of the electrode apparatus into the second connector mate of the neurostimulator.

Securing the electrode apparatus to the subject's temple or forehead may comprise adhesively securing the electrode apparatus to the subject's temple and/or forehead so that an end of the neurostimulator is cantilevered relative to the electrode apparatus, and/or adhesively securing a first region of the electrode apparatus to the subject's temple or forehead, and adhesively securing a second portion of the electrode apparatus to another portion of the subject's head or neck. In some variations, securing the electrode apparatus to the subject's temple or forehead comprises adhesively securing a first portion of the electrode apparatus adjacent to the first surface of the neurostimulator to the subject's temple or forehead and a second portion of the neurostimulator to another portion of the subject's neck or mastoid region.

A method of modulating a subject's cognitive state with a wearable transdermal neurostimulator may include: making an electrical and mechanical connection between a first surface of the wearable transdermal neurostimulator and an electrode apparatus by coupling a first and second connector located off-center on the first surface with a first and second connector mate on the electrode apparatus, so that the electrical and mechanical connection holds a first side region of the first surface to the electrode apparatus while permitting an opposite side region of the first surface to float relative to the electrode apparatus; attaching the electrode apparatus to the subject's temple or forehead; and applying electrical stimulation from the electrode apparatus by delivering pulsed, asymmetric, biphasic current of between about 3 mA to 25 mA that is between about 750 Hz and 30 kHz.

Making the electrical and mechanical connection may include snapping the first connector of the electrode apparatus into the first connector mate of the neurostimulator and the second connector of the electrode apparatus into the second connector mate of the neurostimulator. Making the electrical and mechanical connection may comprise making the electrical and mechanical connection between the first and second connectors on the first surface, wherein the first and second connectors are separated from each other on the first surface by between 0.7 and 0.8 inches, and the first and second connector mates on the electrode apparatus are separated from each other by between 0.7 and 0.8 inches, to provide a connection between a first side region of the neurostimulator and a first region of the electrode apparatus while allowing a second side region of the neurostimulator to float relative to a second region of the electrode apparatus.

Attaching the electrode apparatus to the subject's temple or forehead may include adhesively securing a first region of the electrode apparatus to the subject's temple or forehead, and adhesively securing a second portion of the electrode apparatus to another portion of the subject's head or neck. In some variations, attaching the electrode apparatus to the subject's temple or forehead comprises adhesively securing a first region of the electrode apparatus to the subject's temple or forehead and adhesively securing a second portion of the electrode apparatus to another portion of the subject's neck or mastoid region Any of the electrical stimulation (e.g., neurostimulator apparatuses, including systems and devices) described herein may be configured to controllably and reliably apply a current that is directed to oppose the capacitive charge build-up that may otherwise form on the electrodes, particularly when stimulating in the manner as described herein. This capacitive discharge signal may be included as part of the waveform(s) used by the apparatuses described herein to modulate a user's cognitive state. In general, the capacitive discharge signal is controlled, and opposes the charge build-up on the electrodes. The apparatus may include circuitry (capacitive discharge circuitry) included in the housing.

For example, a transdermal neurostimulator apparatus may include: a housing having a first surface; a first connector and a second connector, wherein the first connector is configured to electrically connect with a first electrode and the second connector is configured to electrically connect with a second electrode; and a controller within the housing, the controller comprising: a waveform generator configured to deliver a pulsed, asymmetric, biphasic current between the first and second connectors, and a capacitive discharge circuit triggered by the controller and connected to one or both of the first and second connectors and configured to deliver a gradual capacitive discharging current pulse during a portion of a cycle of the biphasic electrical stimulation signal to either or both the first electrode and the second electrode. The capacitive discharge circuit may include a double H-Bridge circuit configured to generate the gradual capacitive discharging pulse.

Gradual (in the context of the gradual discharging pulse) may generally include any period of time that is greater than 1 microsecond (µs) (e.g., greater than 1 µs, greater than 2 µs, greater than 5 µs, greater than 10 µs, greater than 15 µs, greater than 20 µs, greater than 30 µs, greater than 40 µs, greater than 50 µs, greater than 100 µs, greater than 150 µs, greater than 200 µs, greater than 300 µs, greater than 400 µs, greater than 500 µs, etc.). More specifically, the capacitive discharge pulse is not instantaneous, and is not the result of shorting ("short circuiting") one or both electrodes, but is instead the application of a current so that capacitive charge on the electrodes connected to the apparatus is opposed and reduced or removed. For example, in some variations, the maximum current of capacitive discharge (e.g., 10 s of mA, generally in the 50 mA or greater range) is either on or off during a portion of a waveform used to modulate the user's cognitive state.

In general, the controller may be configured to trigger the capacitive discharge circuit multiple times within each cycle of the pulsed, asymmetric, biphasic electrical stimulation signal. The capacitive discharge circuit may be configured to generate the gradual capacitive discharging pulse so that it lasts between about 1 microsecond and 1 ms. The controller may be further configured to discharge capacitance built up on the first electrode and the second electrode at different timepoints of an electrical stimulation waveform, wherein the direction of capacitive discharge (i.e. capacitance on which electrode is discharged) may be determined by history of stimulation pulses (i.e. their cumulative history of charge imbalance since a previous capacitive discharge) or may be determined by the neurostimulator controller enabling capacitive discharge in one direction (i.e. from first electrode) but not in the other direction (i.e. from the second electrode).

The controller may be configured to turn off the current source when the capacitive discharge circuit is triggered.

As mentioned above, any of the apparatuses described herein may include wireless communication sub-systems within the housing and connected to the controller.

In any of the electrical stimulator (e.g., neurostimulator) apparatuses described herein, the controller may be configured to trigger the capacitive discharge circuit to deliver the gradual capacitive discharging pulse at a start or an end of a positive-going portion of the biphasic electrical signal. The controller may be configured to activate the capacitive discharge circuit to deliver the gradual capacitive discharging pulse at a start or an end of a negative-going portion of the biphasic electrical signal. The controller may be configured to activate the capacitive discharge circuit at a phase offset from a positive-going or negative-going portion of the biphasic electrical signal (i.e. not at the start or end of a positive-going or negative-going pulse).

For example, a transdermal neurostimulator apparatus may include: a housing enclosing a current source; a first surface on the housing; a first connector and a second connector, wherein the first connector is configured to electrically connect with a first electrode of an electrode apparatus and the second connector is configured to electrically connect with a second electrode; and a controller within the housing, the controller comprising: a waveform generator configured to deliver a pulsed, asymmetric, biphasic current between the first and second connectors, and a capacitive discharge circuit triggered by the controller and connected to one or both of the first and second connectors and configured to deliver a gradual capacitive discharging current pulse during a portion of a cycle of the biphasic electrical stimulation signal, the capacitive discharging current pulse delivering either or both: a first charge to counter a first capacitive charge on the first electrode, and a second charge to counter a second capacitive charge on the second electrode. The countering of capacitive charge on the electrode(s) by the capacitive discharge (and the capacitive discharge circuit) may be partial or complete. For example, the applied capacitive discharge current may not completely eliminate the capacitive charge on the electrode or electrodes. Thus, as used herein "countering" the capacitive charge on the electrode(s) does not require completely eliminating the charge.

As mentioned, the capacitive discharge circuit may include any appropriate circuitry for applying a current to reduce or eliminate any capacitive charge on the electrode(s). For example, a capacitive discharge circuit may include a double H-Bridge circuit configured to generate the gradual capacitive discharging pulse.

The capacitive discharge (e.g., the application of the capacitive discharge current) may be triggered at any point during the application of a waveform. The triggering of the capacitive discharge may be controlled by the controller. For example, the apparatus may include a controller that is configured to trigger the capacitive discharge circuit multiple times within each cycle of the pulsed, asymmetric, biphasic electrical stimulation signal. The controller may be configured to trigger the capacitive discharge circuit to deliver the gradual capacitive discharging pulse at a start or an end of a positive-going portion of the biphasic electrical signal. The controller may be configured to activate the capacitive discharge circuit to deliver the gradual capacitive discharging pulse at a start or an end of a negative-going portion of the biphasic electrical signal.

The capacitive discharge signal (pulse) may be of any duration, but is typically between a few microseconds and a few hundred microseconds (though it could be longer if desired). For example, the capacitive discharge circuit may be configured to generate the gradual capacitive discharging pulse so that it lasts between about 1 microsecond and 1 ms. In general, the duration of a capacitive discharge signal (pulse) may be controlled by limiting or defining the maximum discharge current.

Any of the apparatuses (e.g., devices or methods) described herein, including those with a capacitive discharge circuit, may include electrodes coupled or coupleable to the connectors. For example, the apparatus may include a first electrode connected to the first connector and a second electrode connected to the second connector.

Also described herein are methods of modulating a subject's cognitive state with a transdermal neurostimulator that may include applying a capacitive discharging current pulse during the electrical stimulation, which may allow the use of relatively stronger stimulation (e.g., higher intensity current) than would otherwise be possible. For example, a method of modulating a subject's cognitive state with a transdermal neurostimulator may include: delivering a pulsed, asymmetric, biphasic current between a pair of electrodes of a transdermal neurostimulator attached to subject, wherein the neurostimulator comprises a first connector configured to electrically connect with a first electrode of the pair of electrodes and a second connector configured to electrically connect with a second electrode of the pair of electrodes, and a housing enclosing a controller having a waveform generator and a capacitive discharge circuit; and applying a capacitive discharging current pulse during a portion of a cycle of the biphasic electrical stimulation signal, the capacitive discharging current pulse delivering either or both: a first charge that counters a first capacitive charge on the first electrode, and a second charge that counters a second capacitive charge on the second electrode.

In any of the methods described herein, the method may include delivering a pulsed, asymmetric, biphasic current comprising delivering a pulsed, asymmetric, biphasic current between the pair of electrodes wherein the first electrode is attached to the subject's temple or forehead. For example, delivering a pulsed, asymmetric, biphasic current may include delivering a pulsed, asymmetric, biphasic current between the pair of electrodes wherein the first electrode is attached to the subject's temple or forehead and the second electrode is attached to the subject's neck or mastoid region. Delivering the pulsed, asymmetric biphasic current may comprise delivering a pulsed, asymmetric, biphasic current of between about 3 mA to 25 mA that is between about 750 Hz and 30 kHz.

In general, in any of the apparatuses and methods described herein, the electrodes (and particularly the second electrode) may be configured for placement in any appropriate region of the body, and are not limited to the mastoid and neck regions described in these examples. Other locations include other face regions (e.g., central forehead, etc.), scalp regions, the body below the neck, etc.

As mentioned above, applying a capacitive discharging current pulse may include a controller triggering the capacitive discharging current pulse during a cycle of the pulsed, asymmetric, biphasic current. Applying the capacitive discharging current pulse may include activating the capacitive discharge circuit to deliver the capacitive discharging current pulse before or after a positive-going pulse within the cycle of the pulsed, asymmetric, biphasic current. Applying the capacitive discharging current pulse may comprise activating the capacitive discharge circuit to deliver the capacitive discharging current pulse before or after a negative-going pulse within the cycle of the pulsed, asymmetric, biphasic current. In some variations, applying the capacitive discharging current pulse comprises activating the capacitive discharge circuit to deliver the capacitive discharging current pulse multiple times during one or more cycles of the pulsed, asymmetric, biphasic current.

For example, a method of modulating a subject's cognitive state with a transdermal neurostimulator may include: delivering a pulsed, asymmetric, biphasic current of between about 3 mA to 25 mA that is between about 750 Hz and 30 kHz between a pair of electrodes of a transdermal neurostimulator attached to subject's head, neck, or head and neck, wherein the neurostimulator comprises a first connector configured to electrically connect with a first electrode of the pair of electrodes and a second connector configured to electrically connect with a second electrode of the pair of electrodes, and a housing enclosing a controller having a waveform generator and a capacitive discharge circuit; and applying a capacitive discharging current pulse during a portion of a cycle of the biphasic electrical stimulation signal, the capacitive discharging current pulse delivering either or both: a first charge that counters a first capacitive charge on the first electrode, and a second charge that counters a second capacitive charge on the second electrode.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates a lightweight and wearable electrical stimulation apparatus worn on a subject in accordance with some embodiments of the disclosure.

FIG. 1B illustrates a back perspective view of a wearable electrical stimulation apparatus in accordance with some embodiments of the disclosure.

In FIG. 2B the neurostimulator has a rigid housing that is coupled at only one end by a pair of connectors 227, 227' (e.g., snaps) to the electrode assembly (flexible pad 239 that is configured to adhesively stick to the subject's temple). The opposite end of the neurostimulator 236 is free to float, as shown by the different separations between FIGS. 2B 230 and 2C 232.

FIGS. 3A-3F illustrate front, back, left side, right side, top and bottom perspective views, respectively, of a variation of a neurostimulation device (electrical stimulator) in accordance with some embodiments of the disclosure.

FIG. 4A is a perspective view of a first variation of an electrode apparatus as described herein.

FIGS. 4B, 4C and 4D show front, top and back views, respectively, of the cantilever electrode apparatus of FIG. 4A.

FIG. 5A is an exploded view of the front of the cantilever electrode apparatus similar to that shown in FIG. 4B.

FIG. 5B is an exploded view of the back of the cantilever electrode apparatus similar to that shown in FIG. 4D.

FIG. 6 is an alternative front view of a cantilever electrode apparatus similar to the apparatus shown in FIG. 4B, in which a foam pad is not included over the front of the first electrode region.

FIG. 7A is a perspective view of a variation of an electrode apparatus as described herein.

FIGS. 7B, 7C and 7D show front, top and back views, respectively of the cantilever electrode apparatus of FIG. 7A.

FIG. 8A is an example of a perspective view of a variation of a cantilever electrode apparatus having a capacitive element between the first and second electrodes that can be sensed by a neurostimulator.

FIG. 8B is another example of a perspective view of a cantilever electrode apparatus having a capacitive element between the first and second electrodes that can be sensed by a neurostimulator.

FIG. 16C shows exemplary curvature measurements taken from a sample of users (N=20), showing a generic curvature in one axis.

FIGS. 17A and 17B show front perspective views of a sheet before (FIG. 17A) and after (FIG. 17B) twisting along an axis of twist. FIGS. 17C and 17D show top views, looking down, on the bodies shown in FIGS. 17A and 17B, respectively. FIGS. 17E and 17F illustrate the angle of twist (alpha, $\alpha$).

In FIG. 19B, the electrode assembly is shown on support backing ('liner') that it may be peeled off of (and replaced onto).

FIG. 20 is a table illustrating the detection of three types of electrode assemblies using the capacitance detection circuit of FIG. 19A.

FIGS. 21A and 21B illustrate an example of an undistorted (FIG. 21A) and a distorted (FIG. 21B) current delivered across a pair of dermal electrodes.

FIGS. 21C and 21D illustrate the corresponding electrode voltage for the undistorted and distorted currents of FIGS. 21C and 21D, respectively.

DETAILED DESCRIPTION

Figure 2C:
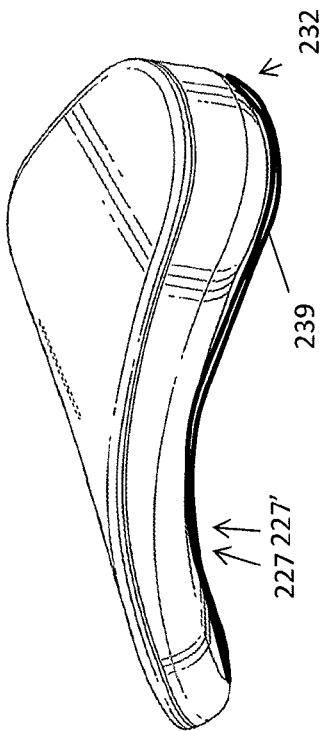
FIGS. 2B and 2C illustrate the cantilever effect of the attachment mechanism on the skin-facing surface of the neurostimulator housing.

The following description of the various embodiments of the invention is not intended to limit the invention to these embodiments, but rather to enable any person skilled in the art to make and use this invention. Disclosed herein are methods and apparatuses, and systems for user control of neurostimulation waveforms.

Lightweight and wearable apparatuses for applying transdermal electrical stimulation and methods of using them for inducing a cognitive effect are described. These apparatuses are typically self-contained, lightweight, and wearable devices and/or systems. The lightweight and wearable transdermal electrical stimulation apparatus for inducing a cognitive effect in a subject may generally include hardware, software and/or firmware components that are configured to generate appropriate control sequences for the device, transmit signals to a current or voltage source and/or conditioner, and connect to electrodes that are configured to be placed on a user for generating electrical currents. For example, the apparatus may comprise a controller configured to transmit sequences to a current generator. Thus, the apparatus may be configured for mobile use.

The apparatus may generally be configured to receive control information for controlling the stimulation. This control may include control of the start, duration, and timing of stimulation (e.g., on/off, duration, etc.) and/or may also include controls for the waveforms to be applied to induce a cognitive effect in a subject. In general, the induced cognitive effect is a function of the position of the electrodes (e.g., where on the head/neck the electrodes are positioned) and the stimulation parameters of the applied waveforms. An apparatus may include one or more manual controls (e.g., inputs) on the apparatus, and/or it may include wireless communication to a remote processor ("base station") that wirelessly transmits control information to the apparatus. For example, the apparatus may include a wireless module (e.g., sub-system, wireless circuit/circuitry, etc.) for wireless communication to the base station or via cellular networks to the Internet. A remote processor may be configured to transmit control signals to a current generator located in the device (e.g., within the primary unit). The remote processor may include non-transitory computer-readable storage mediums storing a set of instructions capable of being executed by a remote processor (such as a smartphone or the like), that when executed by the remote processor causes the processor to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately.

In general, inducing a cognitive effect can include inducing a response that a reasonable user is cognitively aware of. The effect can include a physiological change. For example, the effect can include a change in the amplitude or phase of brain rhythms. The effect can include a modulation of one or a plurality of the following biophysical or biochemical processes: (i) ion channel activity, (ii) ion transporter activity, (iii) secretion of signaling molecules, (iv) proliferation of the cells, (v) differentiation of the cells, (vi) protein transcription of cells, (vii) protein translation of cells, (viii) protein phosphorylation of the cells, or (ix) protein structures in the cells. The apparatus (device or system) may be configured so that the induced cognitive effect is perceived subjectively by the recipient as a sensory perception, movement, concept, instruction, other symbolic communication, or modifies the recipient's cognitive, emotional, physiological, attentional, or other cognitive state. Neurons and other cells in the brain and head area are electrically active, so stimulation using electric fields can be an effective strategy for modulating brain function. In various embodiments of the invention, the effect of electrical stimulation is one or more of inhibition, excitation, or modulation of neuronal activity.

The cognitive effects of TES may be transduced in part and in at least some instances via neuromodulation of a cranial nerve. Thus, improved TES systems and methods improve targeting and activation of appropriate cranial nerves by mapping the particular location (and/or physiology) of a cranial nerve in a subject. Personalization of electrode position(s) and/or TES waveforms so that a cranial nerve can be targeted effectively by TES (and off target effects minimized in cranial nerves that do not induce a desired cognitive effect) would be advantageous for improved intensity and reliability of an induced cognitive effect while also minimizing side effects (e.g. discomfort due to higher than necessary stimulation intensity being necessary to activate a cranial nerve via less than ideal electrode positioning). Mapping of cranial nerves may be achieved by one or more of the group including, but not limited to: imaging, electrical stimulation, muscle recording, nerve recording, or other physiological measurement known to correlate with activation of a particular cranial nerve.

The neurostimulator apparatus can be small and lightweight to be wearable. For example, in some variations the maximum dimension of the housing is less than about 10 cm (e.g., less than about 9 cm, 8 cm, 7 cm, 6 cm, 5 cm, 4 cm, 3 cm, etc., between about 10 cm and about 2 cm, etc.) The wearable neuromodulation devices can be configured to be worn on a subject's head or on the subject's head and neck. The electrode apparatuses can be used with the wearable neuromodulation devices. These electrode portions may also be referred to as cantilevered electrodes. Any of the neurostimulator apparatuses described herein may be used with or may include an electrode apparatus (e.g., a cantilevered electrode, electrode assembly, or cantilevered electrode apparatus); in some variations the electrode assembly (or sub-assembly) may be included as part of the neurostimulator apparatus or may be integrated into/onto the neurostimulator apparatus. Although the single-piece electrode assemblies (that are flat, adhesive members having a first portion onto which the housing of the neurostimulator attaches), as shown in FIGS. 4A-8B are described herein, any electrode apparatus/assembly may be used, including two or more pieces that are separate (and connected by wires, etc.).

FIG. 1A illustrates one variation of a lightweight and wearable electrical stimulation apparatus (e.g., neurostimulator apparatus) that may be worn on a subject via attachment to an electrode assembly; the electrode assembly is a flat, adhesive member that is worn on the user's head, directly against the skin, while the neurostimulator apparatus is connected to the back (non-user facing side) of the electrode assembly. The neurostimulator devices may be small, lightweight and specifically adapted to be conforming to the subject so that they can be worn while the subject goes about their daily activities. Described herein are features or elements that allow or enhance this functionality. These apparatuses (which generally may include systems and devices) may be adapted to be worn on the subject's head (e.g., at the temple and/or forehead region) comfortably even while wearing headgear such as hats, glasses, hoods, scarves, or the like. These neurostimulator devices typically can have a first surface (subject-facing surface) that has a curved and/or twisted shape so that an electrode on the surface conforms to a subject's temple and/or forehead region. The apparatus may also be configured to cantilever off of the electrode assembly, as described below.

In some embodiments, the subject-facing surface can be specifically contoured to fit in the predefined orientation, making it difficult or impossible for a subject to misapply, and risk placing the active region of the attached cantilevered electrode apparatus in the wrong place. This surface can be a section of a saddle shape, in which there is an axis of curvature around which the surface is concavely curved, and an axis of twisting, which may distort the curved surface (the two axes may be different or the same). In addition, these surfaces may be flexible, bendable or otherwise configured to contour to the shape of the subject. As will be described in greater detail below, in some other embodiments, this subject-facing surface can be configured to generally conform to a contour of the head (e.g., include having a user-facing surface that is curved and/or twisted as described herein) but be adapted to cantilever relative of the electrode assembly and/or head, so that one end may "float" at a distance away from the user's head (that may vary between different users or even on the same user from one use to the next) to allow the apparatus to fit various sizes of the heads of the subjects. The electrode apparatus/assembly (which can be referred to as a cantilevered electrode assembly), can be attached to the neurostimulator. The electrode assembly may flex or bend so that it may be secured directly against (e.g., to match the curvature) of the users head. The electrode assembly can be configured to contact the skin of the head of the subject to provide tight fit and good electrical connection. The neurostimulator apparatus may be connected directly to the electrode assembly, so that the electrode assembly holds the neurostimulator apparatus to the user's body.

In general, a neurostimulator apparatus may be adapted to conform to any region of a subject's head. In particular, described herein are neurostimulator apparatuses that are configured to conform to a subject's forehead and/or temple region by having a user-facing surface that is curved and/or twisted so that it approximately conforms to the outer curvature of this region of a generic user's head, but may be oversized, so that it is slightly less curved and/or twisted than the forehead and/or temple region of an average adult. FIGS. 16A-17C illustrate this portion of a user's head, and a configuration of a user-facing surface of a neurostimulator apparatus as described above.

Figure 16A:
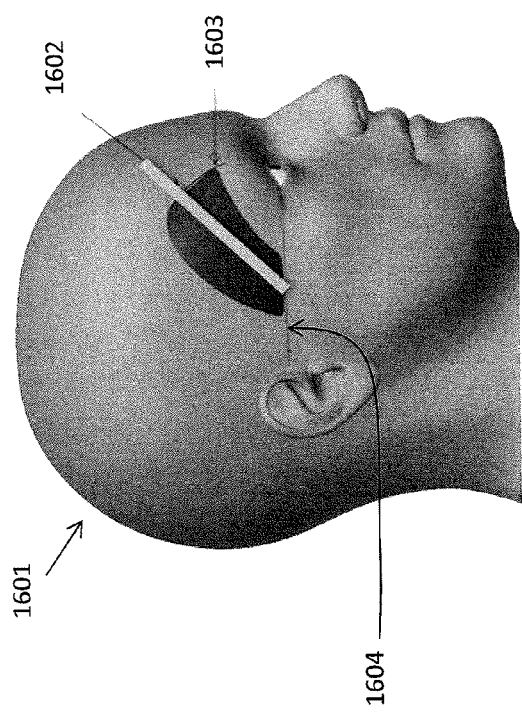
FIG. 16A illustrates one example of placement of a neurostimulator apparatus (TES apparatus) on a user's temple/forehead region.

FIG. 16A illustrates a right temple region (more generally a temple/forehead region) onto which a neurostimulator apparatus may be connected, including connected through an electrode apparatus. For example, as described above, the neurostimulator apparatus may have a low profile, particularly on the end to be worn closest to the cheek when worn correctly, so that the user can wear glasses and the frames of the glasses can fit around/over the neurostimulator apparatus when the unit is coupled to the user's temple/forehead region.

When the neurostimulator apparatus is configured so that the user-facing surface is curved to fit this region, the curvature and shape may also help guide the user in applying/wearing the apparatus. For example, the user-facing curvature of the transdermal neurostimulator apparatus may guide the user in positioning the device correctly relative to landmarks on the head, such as the eyes (e.g., a line between the corner of the eye and the ear 1604), eyebrow, hairline, or forehead (e.g. midline of forehead). FIG. 16A shows a rendering of a user 1601 with a generic neurostimulator apparatus housing 1603 positioned over the right temple and forehead region so that an edge of the neurostimulator apparatus is at or near the line between the edge of the user's right eye and the ear. Line 1602 indicates an axis (which may be referred to as a primary axis, or as a temple axis) along which the user-facing surface of the neurostimulator apparatus may be curved. This is similar to the positioning of the neurostimulator apparatus shown in FIG. 1A, described above.

Figure 16B:
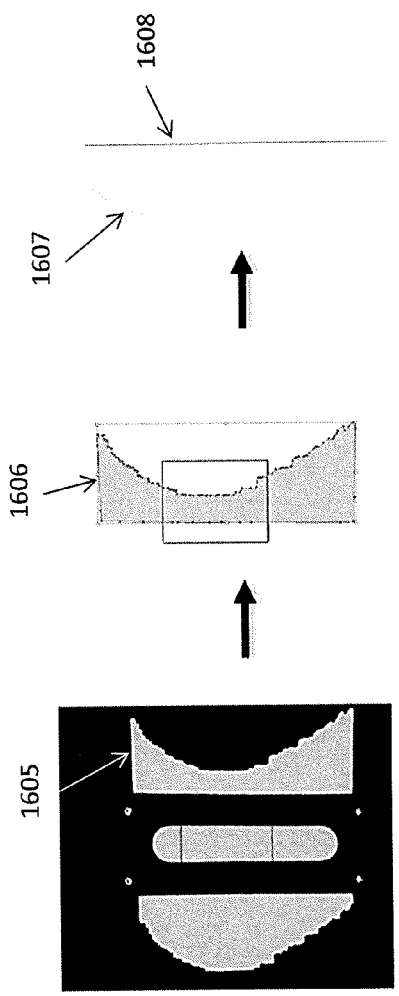
FIG. 16B illustrates one method of determining the curvature of a user's temple/forehead region.

FIG. 16B shows a workflow for using a plastic contour gauge to measure the curvature of a user along line 1602 (the temple axis). In this example, a contour gauge may be pressed against the user's temple and forehead region, capturing an impression on the contour gauge that may be captured by a processed (e.g. thresholded) image 1605. By applying an edge-finding algorithm 1606, a curvature 1607 and alignment/scaling bar 1608 may be determined. This process has been repeated multiple times from a population of human adults to generate an empirical determination of the surface characteristics, including the curvature (including twist about a twist axis), and an example of this is shown in FIG. 16C.

FIG. 16C shows aligned temple/forehead contours for n=20 subjects, as well as two exemplar curvatures of a surface (which may be used to generate a surface for a neurostimulator apparatus to be worn at the temple/forehead region). Surprisingly, the information between different users, even users of a diverse range of body shapes and sizes, as well as users of different ages, are remarkably similar over this region. By using a derived curvature to generate a user-facing surface of a neurostimulator apparatus that is matched to facial curvature at the correct position for the electrode, the apparatus may be more comfortably worn, and users may also be more likely to place (adhere) the unit correctly. In some embodiments, additional features can be added to the housing so that misalignments (e.g. adhere to left rather than right side; adhere too low, too close to eye, too medial (towards midline of forehead)) are more uncomfortable for a user and thus easier to recognize. As mentioned above, the resulting data may be multiplied by a factor (e.g., 1.1×, 1.2×, 1.3×, etc.) when using this information to generate the curvature/twist of the user-facing surface of a neurostimulator apparatus configured to be worn there. Multiplying by a factor may be beneficial for neurostimulators configured for use with a cantilevered electrode.

In any of the transdermal neurostimulators described herein, and particularly those that are connectable to a subject via attachment with an electrode apparatus (as illustrated in FIGS. 1A and 1B, above), the neurostimulator may include a housing that both encloses much of the electronics (e.g., a controller, current source, etc.) and also has a user-facing surface that is curved based on the region of the head where it will be positioned. In particular, the user-facing housing, which may be referred to herein for convenience as a bottom surface, may be concave and twisted along an axis of twist so that it fits this temple/forehead region. As shown in FIGS. 16A-16C, this region may be curved (e.g., along the temple axis) as shown, and it may be twisted along an axis of curvature.

Figure 17A:
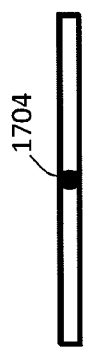
FIGS. 17A-17F illustrate twist (along an axis of twist) for an exemplary body (shown here as a sheet or rectangular body).
Figure 17B:
Figure 17C:
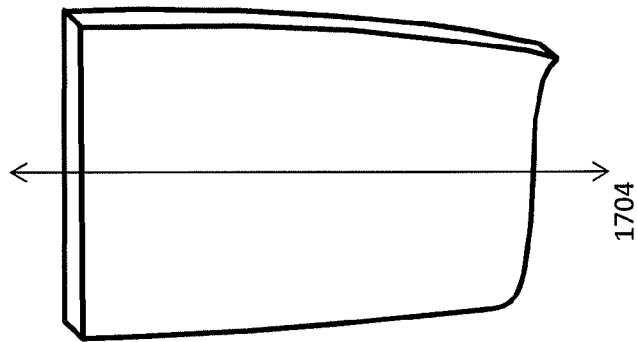
Figure 17D:
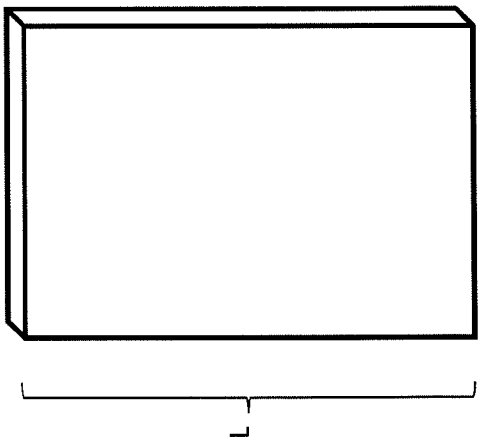
Figure 17E:
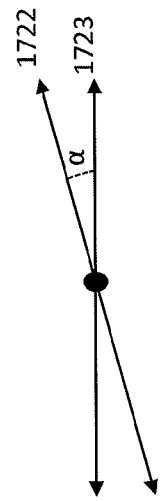
Figure 17F:
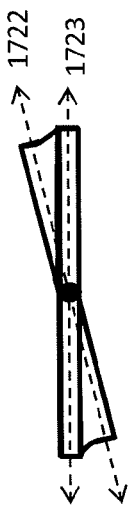

FIGS. 17A-17F illustrate how a surface, such as the surface of a neurostimulator apparatus, may be twisted. In FIG. 17A, the surface of the block (rectangular piece 1702) is shown; FIG. 17B shows the same piece 1702, twisted about the axis of twist (twist axis 1704). This twisting is illustrated in FIGS. 17C and 17D, looking down from a top view along the axis of twist 1704, before (FIG. 17C) and after (FIG. 17D) twisting approximately α degrees (where the angle of twist, α) may be determined as the angle between two lines (in FIGS. 17E and 17F, 1722 and 1723) that are perpendicular to the axis of twist 1704 (the vertex of the angle) along a predetermined length of the axis of twist (e.g., the distal L in FIG. 17A). In this example, the angle α is approximately 15 degrees over the length L of the surface 1702. This surface may also be curved, which may result in curvature of the axis of rotation 1704.

Figures 18A, 18B, 18C:
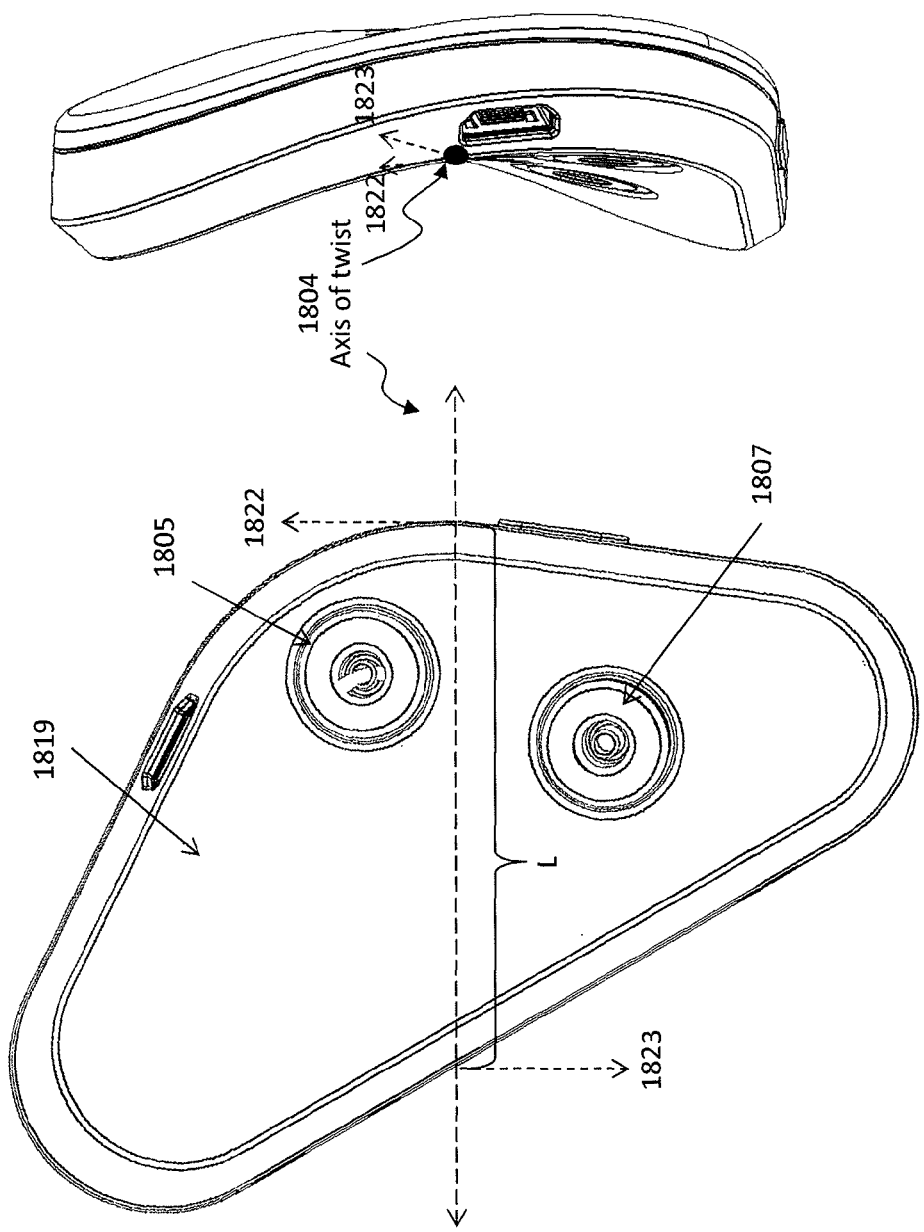
FIGS. 18A and 18B show back perspective and side perspective views, respectively, of a neurostimulator apparatus as described herein having a curved and twisted (along an axis of twist) back, user-facing surface, as well as a pair of connectors separated by approximately 0.72 inches.
FIG. 18C illustrates the angle of twisting of the back surfaces of the apparatus of FIGS. 18A and 18B.

In practice, any of the apparatuses described herein may include a user-facing surface that is twisted along an axis of twist. For example, FIGS. 18A-18B illustrate one example of a neurostimulator apparatus having a user-facing surface with an axis of twist 1804 about which the ends of the device are twisted, which may enhance the comfort and wearability of the neurostimulator apparatus, even when connected to an electrode apparatus that is connected to the users head (e.g., temple/forehead region). In FIG. 18A, the axis of twist extends along the user-facing surface of the apparatus; in other variations it may also be curved, and in particular, may be concave. The twist angle in this example may be estimated from the acute angle formed between the lines that extend normal (perpendicular) to the twist axis over a length, L. As shown in FIGS. 18A, 18B, and 18C, this angle between vectors 1822 and 1823 is approximately 30 degrees over a length of approximately 30 mm (which may be expressed as 1 degree/mm in this example). As described above, the twist of the user-facing surface may vary between, for example, 0.07 degrees/mm and 1.5 degrees/mm.

Tactile and shape cues are beneficial features of TES electrodes and housings for durable components (i.e. power source, microprocessor, current control circuitry, wireless transmitter, etc.) for TES systems intended for self-placement. In general, an edge, corner, or other feature of the shape of a component of a TES system is configured to align, orient, or otherwise position relative to a feature of a user's anatomy. A mirror or video camera (i.e. front-facing camera on a smartphone or tablet) can help a user to guide placement for electrodes in a visible area (e.g. on their face). However, tactile and shape cues for correct placement are useful for circumstances when visual feedback is not possible, including when a mirror or camera is not available, as well as for electrode placements in areas that cannot easily be viewed with a single mirror such as the back of the neck or behind the ear.

For methods that use shape and/or tactile cues for correct electrode or housing self-placement by a user, appropriate instructions (e.g. contained within a kit or provided by a set of images or video) may help a user to understand how to effectively use the shape or tactile cues in placement. In general, shape or tactile cues are beneficial for guiding a user to orient an electrode or TES housing containing an electrode correctly and to place it (wear it) in an appropriate location for delivering electrical stimulation to a target neural region to induce a desired cognitive effect. Cues that relate to common anatomical landmarks are particularly advantageous. The following several examples illustrate how shape and tactile cues can guide positioning of electrode components.

Returning now to FIG. 16A, the rendering shows a TES controller assembly 1603 that contains an electrode in its dermal-facing portion (electrode not shown) on a user 1601. The housing shape of has several anatomical guides so that a user can more easily self-place the housing and underlying electrode in a correct location for inducing a cognitive effect via TES neuromodulation. For instance, the shape of the unit makes it less comfortable when placed on the incorrect side of the face (left) rather than the correct side (right). Instructions provided to a user may identify the shape and tactile cues so that correct anatomical placement is achieved. Straight edge 1604 is designed to be horizontal and aligned to the edge of the right eye. Curved edge nearest the eye wraps around the eye and eyebrow. A raised line may be aligned to the edge of the eyebrow and provide a clear tactile cue such that a user can extend their finger along his/her eyebrow and continue along the raised line. The alignment cue may also be achieved by a button, tab, or any other aligned tactile cue. Alternatively, an LED (which may be observable by the eye beneath, with a mirror, or by a front-facing camera e.g. on a smartphone) can be incorporated in a TES controller housing and may be further configured so that it only turns on when aligned properly. The LED or set of LEDs may be configured similarly to lights on an airport runway that are only observable from particular orientations and thus guide approach angle for landing.

Figure 26:
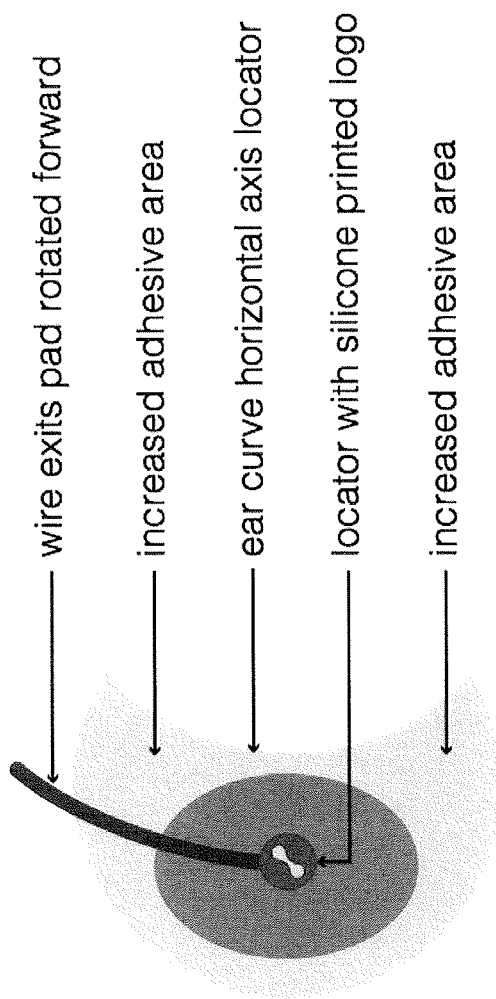
FIG. 26 shows a schematic of an adherent electrode assembly to be placed on the mastoid behind the right ear.

FIG. 26 shows a CAD rendering of a curved, crescent-shaped electrode unit designed to target the right mastoid area behind the ear. The curve of the electrode guides the user to place it on his/her right mastoid (rather than his/her left). A silicone printed logo (alternatively a tab or button or any other tactile cue) is positioned near the center of the electrode and guides a user to place that section directly overlying the bony process of the mastoid. The adhesive areas are positioned so that they do not cover the center of the mastoid yet also do not overlap significantly with areas having hair.

Figure 27:
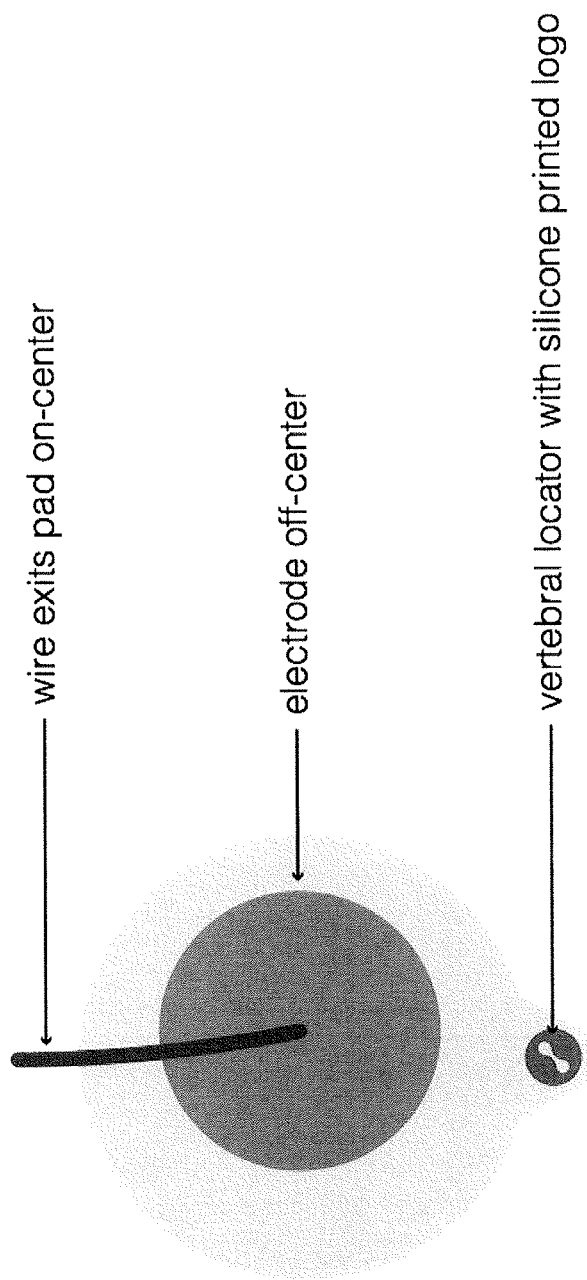
FIG. 27 shows a schematic of an adherent electrode assembly to be placed on the neck, slightly to the right of the midline.

FIG. 27 shows a CAD rendering of a round electrode unit designed to target the neck, centered slightly to the right of the midline. The active electrode area is off center from the full unit (i.e. the white adhesive area is wider on the left than on the right). Also a silicone printed logo tab (alternatively a tab or button or any other tactile cue) is positioned so that a user can align it with a vertebra. An alternative electrode shape for guiding neck placement slightly to the right of the midline is shaped like a capital 'D' and intended for the straight edge to be aligned with the spine.

Figure 28:
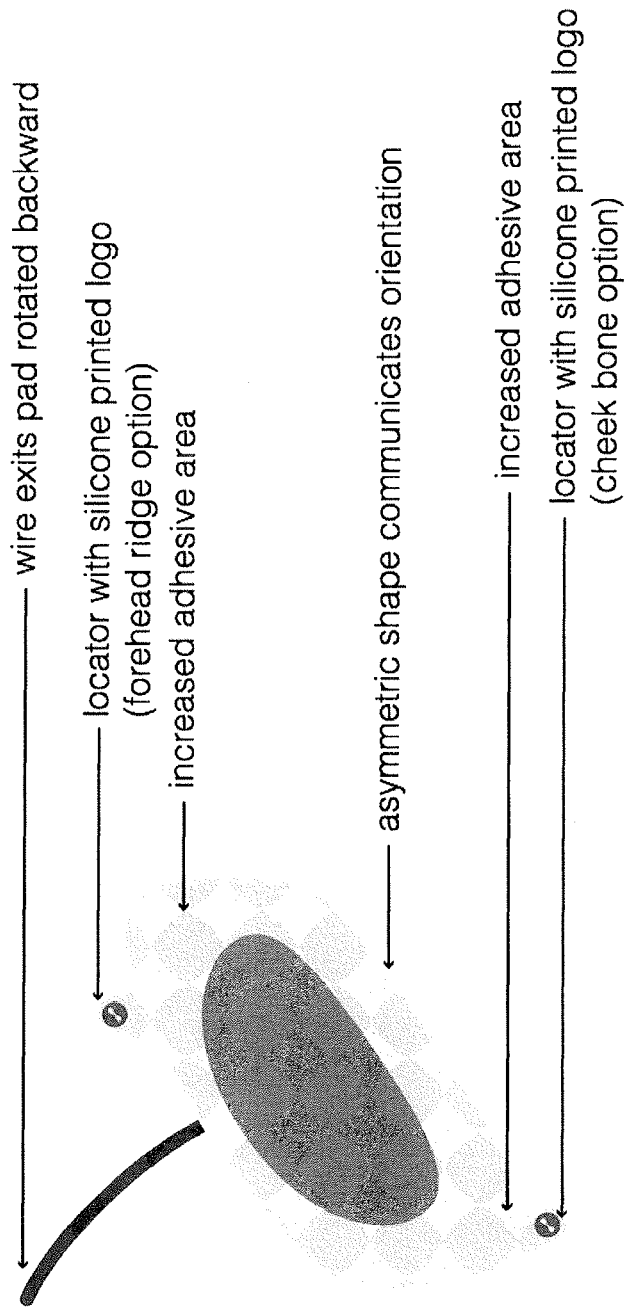
FIG. 28 shows a schematic of an adherent electrode assembly to be placed on the right temple area.

FIG. 28 shows a CAD rendering of an oblong electrode unit designed to target the right temple area above and to the right of the right eye. A first silicone printed logo tab (alternatively a tab or button or any other tactile cue) is positioned so that a user aligns it to the right of their forehead and a second silicone printed logo tab (alternatively a tab or button or any other tactile cue) is positioned so that a user aligns it to their cheekbone. The asymmetric shape guides correct placement on the right side of the face rather than the left.

In general, a transdermal electrode assembly or TES controller assembly that incorporates a transdermal electrode may include a buzzer, piezoelectric material, ultrasound transducer (e.g. CMUT), or other transducer for activating a sensory transduction pathway as a signal for alignment (align the buzzing portion to the side of your eyebrow) or signal of alignment (buzzer activates for correct placement or changes its frequency to indicate closeness to an optimal location).

In general, a transdermal electrode assembly or TES controller assembly that incorporates a transdermal electrode intended for placement near the right temple area may be designed with a low profile on the end closest to the cheek when worn correctly so that glasses frames can fit around the unit when the unit is adhered to a subject's skin (or otherwise worn by the user).

In general, TES systems may improve targeting and effective electrode positioning by using an array of electrodes. For instance, the circuit may be designed so that all active electrodes in the array are isoelectric (i.e. shorted). By selecting a subset of an array of electrodes based on positioning of the entire unit, the accuracy of placement of the active electrode region can be improved without requiring that a subject accurately place the entire assembly or array. These embodiments require components and/or methods to determine the actual location of the entire assembly or array, then a way to manually or automatically select a subset based on desired targeting. Any shaped array, any number of electrodes, and any means of determining the location and orientation of the array can be combined to select an appropriate subset of electrodes for improved targeting.

Figure 29C:
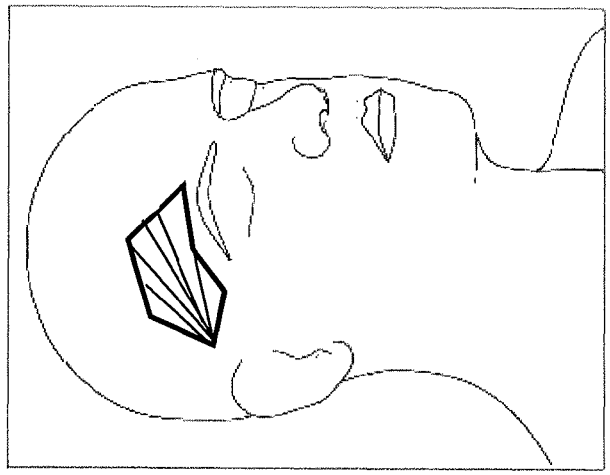
FIGS. 29A-29C show an electrode assembly for use with a neurostimulator having an array of electrodes contained within the electrode assembly that can be used to improve anatomical positioning by activating a subset of electrodes overlying targeted regions of the user.
Figure 29B:
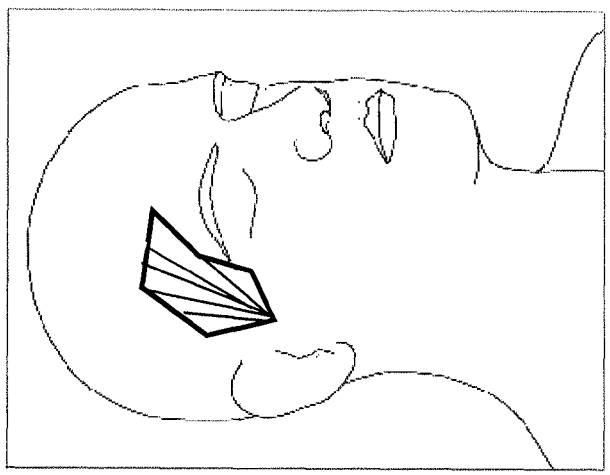
Figure 29A:
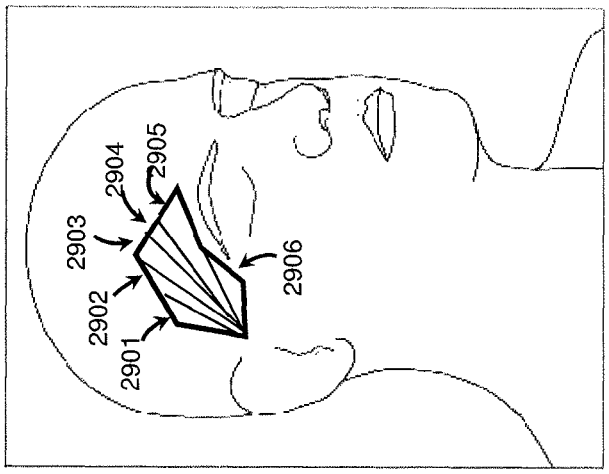

For example, FIG. 29A shows a schematic of an electrode arrays with long, radial electrodes 2901, 2902, 2903, 2904, 2905, and 2906. In FIG. 29A, the array is positioned correctly to target a right temple area, so all electrodes are active. In FIG. 29B, the unit is placed too low, so only electrodes 2903, 2904, and 2905 are active. In FIG. 29C, the unit is rotated and too medial, so only electrodes 2904, 2905, and 2906 are active.

In general, the housing of the neurostimulator apparatus may also have a top surface that is opposite from the user-facing bottom surface. The housing generally includes a thickness in a direction that is generally transverse (or normal) to the bottom and/or top surface, defining the region between these surfaces. Any of the surfaces referred to herein may refer to generally smooth surfaces, though they may include one or more gaps, protrusions, or the like. For example, the user-facing surface 1819 in FIG. 18A includes two openings where the connectors (connector receivers 1805 and 1807) are located.

As described above, the thickness of the housing of the neurostimulator apparatus may be non-uniform, and may be thicker in some regions than in others. Thus, the upper surface may have a different shape (twist, curvature, etc.) than the lower surface. Returning to FIG. 2B, showing an example of a housing of a neurostimulator apparatus, the housing includes a first edge region 250 at one end having a first thickness 256 and a second edge region 252 at second end having a different (and in this example, larger) thickness 255. The thicknesses in this example are measured between the user-facing concave bottom surface and the top surface, and the first edge region 250 is thinner than the second edge region 252. Other edge regions may be taken, but in this example, the two edge regions are opposite of each other along the longest dimension of the apparatus (the orbital edge shown in FIG. 3B). In general, the housing is thin, and may have an average thickness of less than about 30 mm (e.g., less than about 25 mm, less than about 20 mm, less than about 15 mm, less than about 10 mm, less than about 8 mm, etc.).

The housing may have a thickness between the user-facing surface and the top surface that is more than 15% greater at one end of the neurostimulator than at an opposite end of the neurostimulator. In the example shown in FIG. 3E, the thickness of one corner end/edge region (between the auricular and orbital edges) is approximately 0.5× the thickness of the opposite edge region (e.g., the corner region between the superior and orbital edges). Thus, one region has a thickness that is approximately 2× the thickness of another region (approximately 100% thicker). In general, the thickness of the housing between the top surface and first surface may be more than 50% greater at one end of the neurostimulator than at an opposite end of the neurostimulator (or greater than 60%, greater than 70%, greater than 80%, greater than 90%, greater than 100%, etc., though generally less than 500%).

As mentioned above, the neurostimulator apparatuses described herein generally include one or more connectors on, in, or extending from the user-facing surface. In FIGS. 1B, 3B, 3D, 18A, and 18B, apparatuses are shown having a pair of connectors, both configured as female (receiving) connectors that can receive protruding snaps from an electrode assembly, such as the one shown in FIGS. 4A-8B, described in greater detail below. Referring, for example, to FIG. 18A, the first 1805 and second 1807 connectors on the user-facing concave surface 1819 are positioned off-center relative to the user-facing concave surface. As mentioned, in this example, the connectors are snap receivers. The first 1805 and second 1807 connectors are each configured to make an electrical and a mechanical connection with a connector mate (a snap) on an electrode apparatus, as illustrated and described herein with reference to FIGS. 2A-2C. The first and second connectors may be separated by any appropriate length, which will be described in greater detail below. In FIG. 18A, they are separated by between about 0.7 and 0.8 inches (approximately 17.78 mm and 20.32 mm) on center, or about 0.74 inches (approximately 18.80 mm).

Figure 2B:
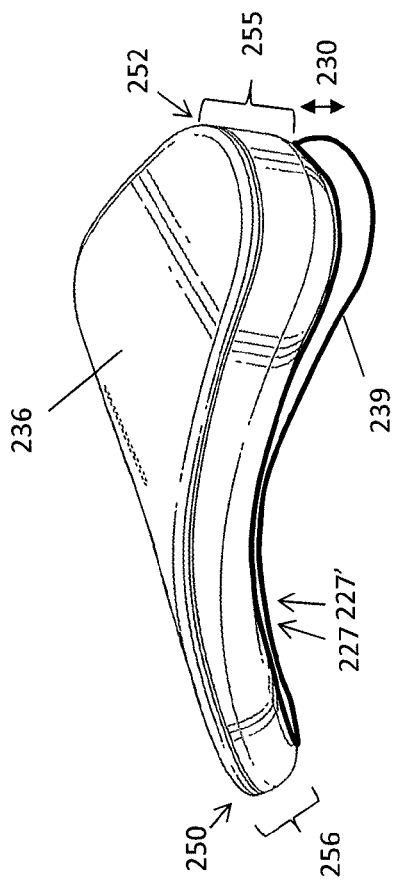

In many of the examples shown here, the neurostimulator apparatus is configured so that the first and second connectors secure an edge region of the user-facing concave surface to the electrode apparatus while permitting an end of the user-facing concave surface opposite from the edge region to move relative to the electrode apparatus. This allows the neurostimulator apparatus to be cantilevered over the electrode apparatus (and the user) as illustrated in FIGS. 2B and 2C, so that one end or edge region 250 is mechanically held relatively fixed to the electrode apparatus 239 and the user by the pair of connectors (not visible in FIG. 2B), while an opposite end region 250 is allowed to float, held cantilevered over the electrode apparatus 239, as shown by the arrows 230. Thus, as the user wearing the apparatus moves her face (including changing her expression, talking, etc.) the separation between the second end region 252 and the electrode assembly 239 (and user) may change without putting stress on the electrical and mechanical connection between the electrode assembly and the neurostimulator housing. Reducing stress on the connectors between the electrode assembly and snap receptacles of the neurostimulator may improve comfort and efficacy of TES waveforms by eliminating or mitigating transients (i.e. 'shocks') caused by intermittency of connection between the connectors of the electrode assembly and neurostimulator.

In general, a connector between a transdermal electrode and a durable assembly of a TES system may use a connector that has a magnet (i.e. a 'maglock' or magnetic power connector), wherein one polarity of the magnet is on the connector of the electrode and a magnet of the opposite polarity is contained within a durable portion of the TES system. Magnetic connectors can enable automated alignment of electrically conductive and/or mechanically matched components (e.g. to fit together and transmit current from the controller to the electrode).

The spacing between the connectors connecting the electrode assembly and the housing of the neurostimulator apparatus may be configured to permit the cantilevered connection. For example, spacing that is less than about 0.5 inches (approximately 12.7 mm) may be too close and may permit torqueing or dislodgement of the housing of the neurostimulator, particularly when the housing is sized as described herein (e.g., having a largest length dimension of greater than about 4 cm, and in some instances less than about 15 cm) and weighing less than about 7 ounces (e.g., between 0.1 ounces and 7 ounces). Spacing that is larger than about 1 inch may, in some variations, make the connection overly stiff, and prevent the apparatus from connecting to different head curvatures. The inventors have found that spacing generally between about 0.5 and 1 inch may provide a stable and comfortable attachment, preventing a large moment arm from developing even for larger sizes/weights of devices.

By positioning the connectors off-center relative to the user-facing surface (e.g., along a first end/edge region, the opposite end/edge region may be allowed to move somewhat relative to the electrode assembly beneath it, as described above. For example, returning to FIG. 3B, the pair of connectors (snap receivers) shown are positioned off-center from the bottom of the device nearest the auricular edge of the device, while the opposite end (the intersection between the superior edge and the orbital edge) would be allowed to float relative to the other end/edge region when connected to an electrode assembly.

In many of the examples described herein, the neurostimulator housing is trianguloid, having three sides (in FIG. 3B, the superior edge, auricular edge and orbital edge, each slightly curved) with three "corners" that are rounded.

In some embodiments, the neurostimulator can be configured to fit under the temple portion of an eyeglass frame for users wearing glasses, thus the portion of the combined assembly (electrode assembly and neurostimulator) can be thin enough to fit between glasses and the temple region. In some embodiments, the thickness at a first end of the neurostimulator that is configured to extend between an eye and a temple of the subject can be sufficiently thin to fit under an eyeglass frame of the subject. For example, the thickness at the first end can be between 0.1 and 10 mm (e.g., between 1 mm and 8 mm, between 2 mm and 7 mm, etc.).

In some embodiments, however, it may also be beneficial to have some portions of the neurostimulator be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry at one end (e.g., an end that is worn higher up on the face). Thus, it may be beneficial to locate the mechanical/electrical connectors, such as snaps, that extend proud from the cantilevered electrode assembly toward the thinner end, separated from the battery compartment of the neurostimulator to reduce the overall thickness of the system in some variations, allowing the connectors to fit under or within through-holes of a PCB rather than under a thick battery portion (or under both). However, it may be beneficial to have the connector(s) positioned under the battery portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the neurostimulator may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered one type of mechanical connector, and may be present on the electrode assembly and/or on the neurostimulator body). It may also be beneficial to have at least one of the electrical/mechanical connectors (such as a snap) at or near (and preferably behind) the active area of the first electrode portion, as this may make the electrical connection with the hardware unit easier and more robust.

In some embodiments, the thickness of the device (measured from the first surface) can be thinner at one end and thicker at the other end. As shown in FIG. 1A, the thinner end 1 may be configured to be oriented relative to the subject's eye, with the thicker region 2 worn higher on the subject's head. The neuromodulation devices described herein are also configured to include attachments to the cantilevered electrodes on the underside (e.g., the first surface), providing electrical connection to at least two electrodes on the cantilevered electrode assembly. These neuromodulation devices may also be referred to as neurostimulation devices, neurostimulators, neuromodulators, applicators, neuromodulation applicators, electrical stimulators, or the like.

In some embodiments, for example, the overall shape of the neurostimulator can be triangular (including rounded edges) as shown in FIG. 1A. As used herein triangular includes shapes that have rounded/smooth transitions between the three sides, as illustrated. The side of the unit 3 worn toward the ear can be the auricular edge, the side 4 worn highest on the forehead can be the superior edge, and the side 5 worn nearest the eye/eyebrow can be the orbital edge. In some other embodiments, the device may have a differently shaped profile. For example, the profile can be generally rectangular, generally trapezoidal or generally ovular. The profile can have rounded edges or generally sharp edges.

As shown in FIG. 1B, the first surface of the neurostimulator, to which the cantilevered electrode apparatus attaches, may include mating junctions (openings, receptacles, female receivers, etc.) to receive and make electrical and mechanical contact with the connectors on the cantilevered electrode apparatus. These receivers may also be positioned to optimize the placement of the cantilevered electrode apparatus, allowing it to make sufficient contact with the neurostimulator and subject, and prevent the cantilevered electrode apparatus from bending or breaking contact, even while the subject is mobile and/or active.

In some embodiments, the wearable transdermal electrical stimulator may include a button for control by the subject. The subject may use the button to stop or reset the neurostimulator when necessary. In some embodiments, the wearable transdermal electrical stimulator may include a light indicator configured to provide visual feedback or a transducer for providing tactile feedback. For example, the light indicator can be used to indicate the connection of the electrodes, the status and progress of the TES stimulation session. For example, the tactile indicator can be used to indicate function of the device (e.g. 1 minute left in waveform; batteries low; placement incorrect, etc.) while worn on the head when a user cannot easily view a visual indicator without a mirror or front-facing camera of a smartphone or the like.

Figure 2A:
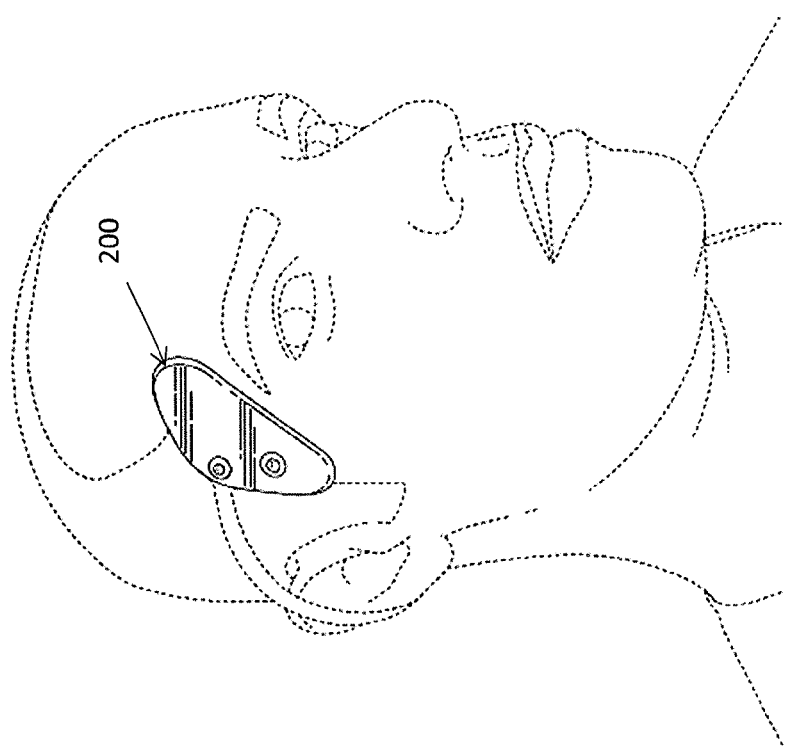
FIG. 2A illustrates a cantilever electrode apparatus on a subject's head.

FIG. 2A illustrates a variation of an electrode apparatus 200 worn on a subject's head. Examples of electrode apparatuses may also be seen in U.S. patent application Ser. No. 14/634,664, titled "CANTILEVER ELECTRODES FOR TRANSDERMAL AND TRANSCRANIAL STIMULATION," and filed Feb. 27, 2015 and herein incorporated by reference in its entirety. As illustrated, the apparatus is positioned with the first electrode portion on the temple and forehead region and a second electrode portion behind the head (e.g., behind the ear or neck region, not shown). In this example, a neurostimulator (not shown in FIG. 2A) may be attached to the cantilevered electrode apparatus either before or after it is applied to the subject. For example, the mechanical and electrical connectors may be snapped together between the housing of the neurostimulator and the electrode apparatus.

FIGS. 3A-3F illustrate perspective views of one variation of a neurostimulation apparatus. In some embodiments, the overall shape of the neurostimulator may be triangular, and particularly the surface of the neurostimulator (though curved/concave and twisted) adapted to connect to the electrode apparatus and face the user may be three-sided (e.g., roughly triangular). As mentioned above, this roughly triangular shape may include rounded edges, and the thickness of the stimulator (in the direction perpendicular to the surface contacting the cantilevered electrode apparatus) may vary, e.g., be thinner along one side, and particularly the side (the portion between the orbital edge and the auricular edge) that will extend between the eye and the temple. This shape may also be beneficial when helping to fit and/or be worn on most people in a region of the head (e.g., face) that tends to not have hair. This thin lower corner (the orbital/auricular corner) may fit between the eyebrow and hairline, while the wider portion is positioned up in the forehead area where there is less likely to be hair.

In FIGS. 3A-3F the various edges are labeled, based on where the apparatus will be worn by the subject, similar to what is illustrated in FIG. 1A. In general, the side of the unit worn toward the ear is the auricular edge, the side worn highest on the forehead is the superior edge, and the side worn nearest the eye/eyebrow is the orbital edge. In some embodiments, the overall shape of the neurostimulator can be triangular (including rounded edges). In some other embodiments, the overall shape of the neurostimulator can be of a variety of shapes. The subject-facing surface can be contoured to fit in the predefined orientation. This surface can be a section of a saddle shape, in which there is an axis of curvature around which the surface is concavely curved, and an axis of twist, which may distort the curved surface. When attaching the cantilevered electrode apparatus to the neurostimulator, the cantilevered electrode apparatus may flex or bend so that it is contoured to match the curved and twisted surface.

In general, the electrode apparatuses described herein may act as an interface between the wearable, lightweight and self-contained neurostimulator ("electrical stimulator") and a subject's body, particularly the head or head and neck region, where stimulation is to be applied. These cantilever electrode apparatuses may be disposable (or semi-disposable) components that are connected to the neurostimulator and applied directly to the subject; energy (typically current) from the neurostimulator is guided and delivered to the subject by the cantilever electrode apparatus. Although the neurostimulator may be small and lightweight, the cantilever electrode apparatus may allow it to secure to the subject's body and deliver energy to two or more regions on the body (e.g., temple, neck, chest, etc.) that are separated by a distance that is much greater than the size of the neurostimulator.

The cantilever electrode apparatuses described herein generally include at least two electrode regions, separated from each other along an elongate body. The cantilever electrode apparatus typically attaches to the neurostimulator device by two (or more) electrical connectors (which may be referred to herein as connectors) that are in electrical contact with the electrode regions. The electrical contacts may be positioned on the cantilever electrode apparatus adjacent each other and in a particular manner that permits both the secure attachment to the neurostimulator and prevents disruption of the electrical contact while the cantilever electrode apparatus is worn by the subject, even while the subject moves about. For example, the spacing of the connectors may be between 0.6 and 0.9 inches apart on center (from center to center), and more preferably between about 0.7 inches and about 0.8 inches. The electrical connectors typically extend from the otherwise substantially flat surface of the cantilever electrode apparatus, and may plug into the neurostimulator. The electrical connectors may mechanically engage with the neurostimulator (e.g., they may be snaps), which may also provide mechanical support for the connection between the cantilever electrode apparatus and the neurostimulator, and thereby help support and hold the neurostimulator on the subject's body when the cantilever electrode apparatuses is attached to the subject's body.

In general the cantilever electrode apparatuses include two or more connectors at or near one end of the elongate body of the cantilever electrode apparatus, and two (or more) electrode regions are positioned along the elongate body of the cantilever electrode apparatus. The two or more connectors (which may also be referred to as electrical or mechanical and electrical connectors) may be at one end or edge region and help secure the entire cantilever electrode apparatus to the neurostimulator, even while a second electrode region is positioned at a distance (e.g., greater than 2 inches, greater than 3 inches, greater than 4 inches, etc.) along the elongate body of the cantilever electrode apparatus from the connectors and another electrode region.

Each electrode region of the electrode apparatuses described herein typically includes an active region on a back side of the electrode region that is adapted to contact the subject. The active region may include a hydrogel that transfers energy (e.g. current) from the neurostimulator to the subject's skin. The active region is in electrical communication with the connector.

In general, the elongate body forming the cantilever electrode apparatuses may be made of a material that is rigid in at least one direction, even while flexible in another direction. For example, the elongate body of the cantilever electrode apparatus may be formed of a relatively flat sheet of material (e.g., flex circuit material) that is relatively thin (e.g., less than 3 mm, less than 2 mm, less than 1 mm, etc.). The sheet of material may extend in a plane, and the material may not be bendable in the direction of the plane although it may be bendable out of the direction (e.g., can be curved up/down), and may twist. This partial rigidity may help support the cantilever electrode apparatus on the body while allowing it to conform to a wide variety of subject body sizes. In some variations the cantilever electrode apparatus is made of a material that is rigid, but can be bent by the application of force to hold a shape. For example, the elongate body of the cantilever electrode apparatus may be ductile, e.g., may be made (at least in part) of a shape memory material that allows bending.

Usability and miniaturization of a wearable TES system may be improved by the use of flexible or stretchable components, including but not limited to: electronic circuits, power source (i.e. flexible solar panel or flexible/bendable batter), and communications module (e.g. wireless communications module). Recent advances in materials science and the design and manufacture of flexible/stretchable electronic circuits support a miniaturized, wearable TES system that is worn on or adhered to the body. Various components and technologies may be used for constructing a flexible and/or stretchable TES system. One skilled in the art of flexible circuits, flexible sensors, or flexible power sources will recognize that other materials, methods, and technologies may be used to improve the conformability, comfort, and disposability of a wearable TES system.

Examples of materials and technologies which can be used to improve the flexibility and wearability of a TES system include: elastic strain sensors for sensing muscle contraction (e.g. stretch sensors from Danfoss Poly Power A/S); 'tattoo' electronics developed by companies, including MC10, Inc. (Cambridge, Mass.) and Electrozyme (San Diego, Calif.), including those with features described in U.S. Pat. Nos. 8,536,667 and 8,097,926 to de Graff et al., as well as technologies that can integrate solid state components (e.g. those developed by John Rogers et. al); thin film batteries (e.g. batteries composed of polymers, carbon nanotubes, and/or nanoporous nickel fluoride); a flexible supercapacitor made of graphene and carbon nanotubes; flexible OLED display; components containing single layer graphene developed by Samsung; and components containing molecularly stretchable electronics.

Improved adherence of electrodes and other TES components would benefit from the use of 'geckskin' developed by Irschick and Crosby at the University of Massachusetts— Amherst, which can hold strongly to a smooth surface yet can be removed easily without leaving a residue.

The configuration of the cantilever electrode apparatuses described herein may provide numerous benefits compared to other possible arrangements, including variations in which a wire or separate connection connects a second (or more) electrode region to a neurostimulator. For example, the cantilever electrode apparatuses described herein may include least a few mm of adhesive surrounding the active area of each electrode, which may help make good contact with the skin when the cantilever electrode apparatus is attached to a wearable neurostimulator. In another example, the cantilever electrode apparatuses described herein may include at least a few mm of adhesive in sections bordering an active electrode area. For electrode apparatuses and microstimulators that are configured to be worn on the temple (e.g., adjacent to the eye), the amount of adhesive in one portion of the electrode apparatus may be limited; in particular, the portion that will be positioned below a lower edge of the electrode, to prevent the unit from extending too far towards the eye and/or towards the hairline at the temple. In some variations it is desirable to have the cantilever electrode apparatus and the electrical stimulator with its overlaying hardware unit positioned on the face so that it does not interfere with a temple portion of a pair of glasses that may be worn while wearing the device (e.g., the region adjacent to the ear). In addition, it may be beneficial for the bottom edge of the cantilevered electrode assembly (at the first electrode portion) to correspond with the bottom edge of the electrical stimulator to help guide self-placement using the lower edge of the device to align horizontally with the edge of the eye, an easy landmark for self-placement; thus, it may be beneficial to limit the amount of adhesive below/around the lower section of the electrode.

In some embodiments, an electrically conductive tethering wire may be part of a disposable electrode assembly that couples to the neurostimulator. A subject may unfurl the electrically conductive tethering wire as needed so that two or more electrode portions can be adhered to appropriate parts of the head to deliver TES neuromodulation to a brain region of interest.

As mentioned above, there are also numerous benefits of using a connector for electrically connecting the active regions of the cantilever electrode apparatus to the electrical stimulator both mechanically and electrically. For example, an apparatus that uses a mechanical and electrical connector, such as a snap connector or other connector that stands proud from the relatively thin cantilever electrode apparatus may prevent misadjustment of the apparatus. In particular, it may be beneficial to have two connectors (e.g., snaps) rather than just wires or one snap and a wire to connect the wearable apparatus and the cantilevered electrode apparatus. The second mechanical/electrical connector such as a snap may improve the physical connection between electrode adhesive pad and hardware unit (neurostimulator/electrical assembly). In addition, the hardware unit (neurostimulator/electrical stimulator) and electrode apparatus may fit under the temple portion of an eyeglass frame for users wearing glasses; thus the portion of the combined assembly (electrode assembly and neurostimulator) should ideally be thin enough to fit between glasses and the temple region. However, it may also be beneficial to have some portions of the system (e.g., the neurostimulator) be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry at one end (e.g., an end that is worn higher up on the face). Thus, it may be beneficial to locate the mechanical/electrical connectors such as snaps that extend proud from the cantilevered electrode assembly toward the thinner end, separated from the battery compartment of the neurostimulator to reduce the overall thickness of the system in some variations, allowing the connectors to fit under or within a through hole of a PCB rather than under a thick battery portion (or under both). However, in some variations it may be beneficial to have the connector(s) positioned under the battery portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the hardware unit may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered one type of mechanical connector, and may be present on the electrode assembly and/or on the neurostimulator body).

It may also be beneficial to have at least one of the electrical/mechanical connectors (such as a snap) at or near (and preferably behind) the active area of the first electrode portion, as this may make the electrical connection with the hardware unit easier and more robust.

FIGS. 4A-4D illustrate one variation of an electrode apparatus ("cantilevered electrode apparatus") that may be used with a neurostimulator that is worn on a subject's head. In this example, the cantilevered electrode apparatus 100 includes a plurality of electrode portions (two are shown) 103, 105. In FIG. 4A, a front perspective view is shown. The front side is the side that will face away from the subject when worn. The cantilevered electrode apparatus is thin, so that the electrode portions include a front side (visible in FIGS. 4A and 4B) and a back side (visible in FIG. 4D). As shown in the side view of FIG. 4C, the device has a thin body that includes the electrode portions 103, 105 as well as an elongate body region 107 extending between the two electrode portions. The elongate body is also thin (having a much larger diameter and height than thickness (the thickness is shown in FIG. 4C)).

In this example, two connectors 115, 117 (electrical and mechanical connectors, shown in this example as snaps) extend from the front of the cantilevered electrode apparatus. The front of the first electrical portion 103 may also include an optional foam and/or adhesive material 121 through which the snaps extend proud of the first electrical portion. The first electrical portion is shaped and sized so that the snaps will connect to plugs (ports, holders, opening, female mating, etc.) on the electrical stimulator. As described above, the connectors on the electrode apparatus may be spaced in the same manner as the complimentary connectors on the housing of the neurostimulator apparatus. For example, the connectors on the electrode apparatus may be separated by between about 0.5 and about 1 inches (e.g., between about 0.6 and about 0.9 inches, between about 0.7 and about 0.8 inches, etc., shown in FIGS. 4A-4D as about 0.72 inches). The second electrode portion may also include a foam or backing portion 123. This foam/backing region may be optional.

FIG. 4D shows a back view of this first example of a cantilevered electrode apparatus. In this example, the first 103 and second 105 electrode portions are also shown and include active regions 133, 135. The active regions are bordered by adhesive 140. The first 103 electrode portion includes, on the back (user-contacting) side, a first active region 133, surrounded by an adhesive material 140 that extends to the edge region of the electrode assembly. The active region may include a conductive material (e.g., electrically conductive gel). Similarly, the back of the second electrode portion 105 includes the second active region 135 which is bounded on an upper and lower side by an adhesive 140. The adhesive may be any biocompatible adhesive that can releasably hold the material to the skin.

FIGS. 5A and 5B show exploded views of the exemplary cantilevered electrode apparatus of FIGS. 4A-4D. In FIG. 5A, the front side of the cantilevered electrode apparatus is shown with the foam backing 121, 123 (which may be adhesive on one or both sides) materials and snaps 117, 115 removed. The snaps may include two parts (not shown in FIG. 5A), a base and a post, and the base may be positioned on the back side of the elongate body forming the substrate (or base) 108 for the cantilevered electrode apparatus. The base may be a flex circuit material, e.g., that is relatively insulating, flexible out of the plane of the material, but rigid in the plane (meaning it can be bent up/down out of the plane, but has rigidity when pushed/pulled in the direction of the plane of the material). Many of the structures used to form the electrode regions and connectors may be printed directly onto the base or attached to the base. For example, in FIG. 5B, the back (user-facing) side of the base of the cantilevered electrode apparatus is shown with the snaps attached so that the base of the snaps extends along the back side and can be in electrical contact in one case with the electrically conductive first active region forming part of the first electrode portion. The second snap is offset from the electrically active region and may contact a conductive trace (e.g., printed on the body 108 of the base) and extending along the elongate body region 107 until it contacts the second active region. In this manner, the first and second connectors may establish electrical communication between the active regions and the neurostimulator. In FIG. 5B the active regions include a conductive gel (although additional materials, including sacrificial materials, pH buffer materials, antibacterial/germicidal materials, etc. may also be included). The adhesive portion 140 is also shown in this exploded view.

As described above, the foam material over either or both of the front sides of the first and second electrode portions may be omitted. FIG. 6 shows an example in which the foam material, which may also or alternatively be an adhesive to help secure the cantilevered electrode apparatus to the neurostimulator is not included in the cantilevered electrode apparatus. In this example, the connectors (snaps 117, 115) alone may be used to secure the cantilevered electrode apparatus to the neurostimulator.

The cantilevered electrode apparatus shown in FIGS. 4A-6 may be particularly useful, for example, to connect a neurostimulator to a subject's head so that the neurostimulator is attached to the front side of the cantilevered electrode apparatus by snapping onto the proud connectors, while the elongate body region 107 is bent to extend behind the subject's head and down to a portion on the midline of the back of the user's neck. Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE" and filed on Jun. 30, 2014, now U.S. Pat. No. 9,014,811 and herein incorporated by reference in its entirety.

FIGS. 7A-7D illustrate another example of a cantilevered electrode apparatus. This example is very similar to the variation shown in FIGS. 4A-5B. The connectors (snaps 417, 415) are in the same position as shown in FIGS. 4A-4D, as are the shape of the first electrode portion 403 and foam/backing material 421 (which may also or alternatively be an adhesive material). However, the example shown in FIGS. 7A-7D includes a different overall shape, and may be used to connect, for example, to different regions of the user's head/neck. In particular, the portion of the substrate forming the elongate body region 407 extending between the two electrode portions 403, 405 is shaped slightly differently. In this example, the cantilevered electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple region, using the adhesive material 440 surrounding the electrically active region 433 to hold the electrically active region (and the attached neurostimulator) in position, the second electrically active region may also be adhesively 440 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 4A-6 and FIGS. 7A-7D.

Figure 24A:
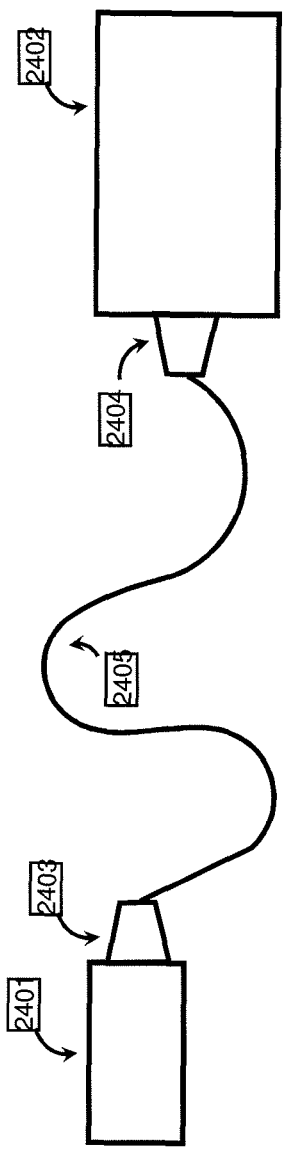
FIGS. 24A-24C show schematic representations of a TES apparatus having two modules connected by a durable cable that can be disconnected.

In alternative embodiments, an electrically conductive tethering wire may be a durable portion of the TES system and intended for long-term use. FIG. 24A shows exemplar schematic embodiments of a TES system comprising primary durable housing 2402, secondary durable housing 2401, connectors 2403 & 2404, and electrically conductive tethering wire 2405. Not shown are disposable electrodes that couple electrically and mechanically to housings 2401 & 2402 and contain a dermally-facing adhesive so that the TES system can be wearably attached to the user. Other variations of TES systems as described herein may be non-adherent and otherwise wearably attached to a user's body (e.g. by a headband, cap, etc.).

Figure 24B:
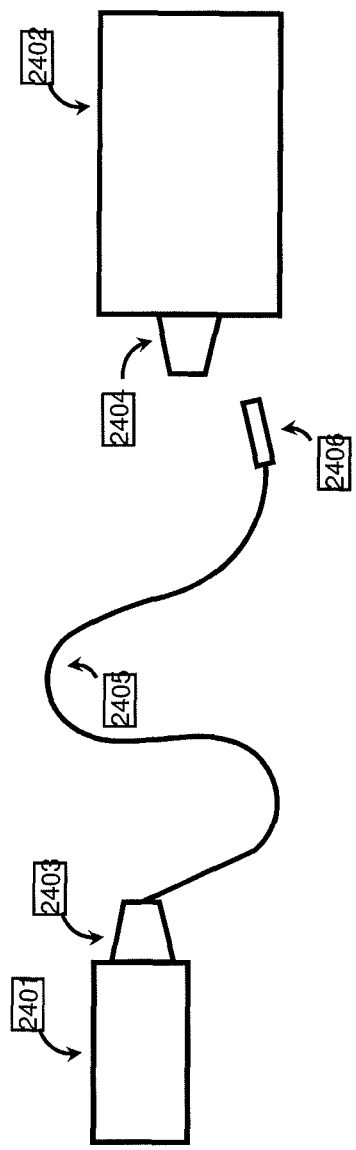
Figure 24C:
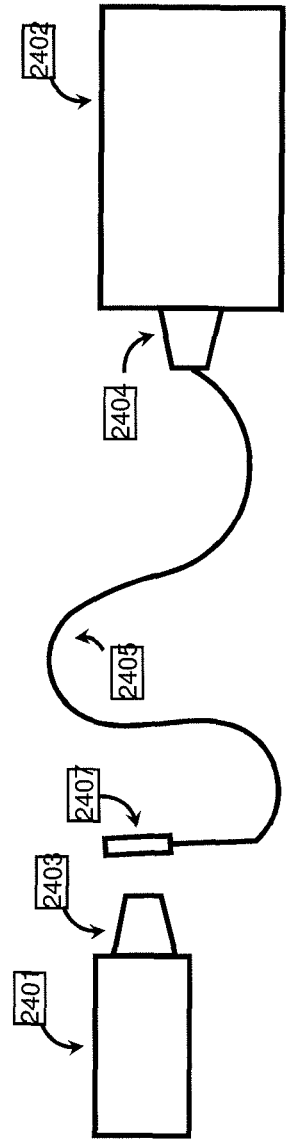

As shown in FIG. 24A the tethering wire may be permanently attached to the primary and secondary units, or it may be configured to unplug from either or both of the primary or secondary TES system housing (FIG. 24B, FIG. 24C) with standard or custom connector 2406, 2407.

In some embodiments, one of the durable housing may have a standard plug component (e.g. a male USB or male micro-USB connector) for charging and communication with other electronic or computing devices. For example, the smaller, secondary durable housing may contain a male USB connector, a charging circuit, and a battery.

In general, TES systems containing an electrically conductive cable that is permanently or detachedly attached may contain all components in a single housing. In such instances, the electrically conductive cable would include at least a connector at or near its end distal from the unit containing the electrical components to which a disposable electrode can be electrically connected.

Figure 25:
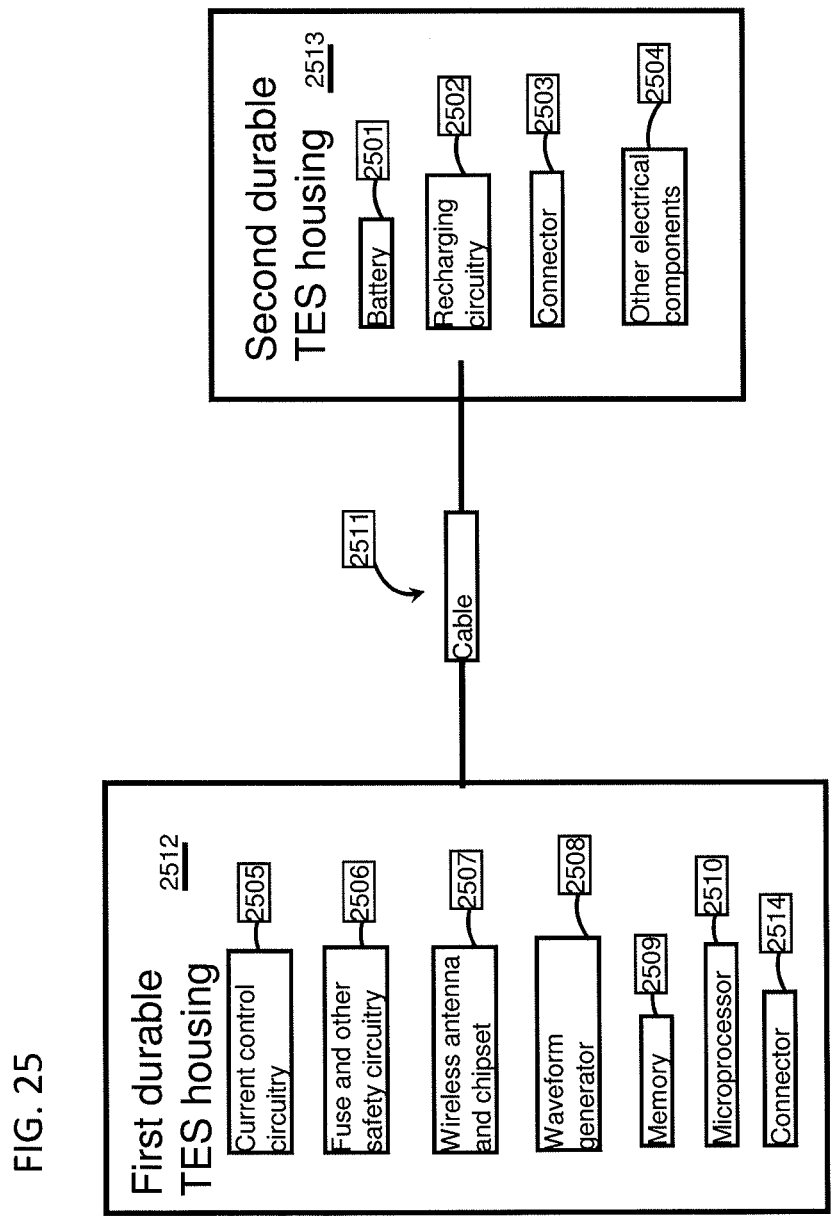
FIG. 25 shows the hardware features in a first durable TES housing and a second durable TES housing connected by a cable.

In general, TES systems containing an electrically conductive cable that is permanently or detachedly attached may contain components in two or more housings. These embodiments are advantageous because they permit miniaturization of each of the housings relative to having all components in a single housing. This miniaturization may improve comfort, wearability, durability, and/or fit of a TES system. Any set of necessary or optional components may be selected to be in a first housing or a second housing (or a third housing, etc.). FIG. 25 shows an exemplar TES system schematic with first durable TES housing 2512 containing current control circuitry 2505, fuse and other safety circuitry 2506, wireless antenna and chipset 2507, waveform generator 2508, memory 2509, microprocessor 2510, and connector to first electrode (2514) connected by electrically conductive cable 2511 to second durable TES housing 2513 containing a battery 2501, recharging circuitry 2502, connector to second electrode 2503, and other electrical components 2504.

A method of using the TES systems described herein can include connecting two TES controller housings with a detachable, reusable electrically-conductive cable, followed by connecting the two electrodes to the cable and/or TES controller. Alternative methods can employ the opposite ordering of connecting necessary and detachable system components.

A TES apparatus with a durable cable connecting two housings with electrode connectors—or a single housing with two or more electrode connectors—may be used with disposable electrodes that do not have a wire connecting them. This system architecture reduces the cost and complexity of a disposable set of transdermal electrodes, which only require a connector (e.g. electrically conductive button snap connector) configured to connect with the TES controller system.

FIGS. 8A and 8B illustrate two different types of cantilever electrode apparatuses, each having an electrically detectable element, for example, a capacitor connecting the electrode contacts. The electrically detectable element can be a capacitor or a capacitive element in some embodiments. In some other embodiments, the electrical detectable element may be another type of electrical element. In some embodiments, each of the cantilever electrode apparatuses can have an electrically detectable element. In some other embodiments, only one of the cantilever electrode apparatuses may have an electrical detectable element (so that it can easily be distinguished from the version of the electrode apparatus having the electrically detectable element). The detection circuit in the neurostimulator can be configured to detect the electrically detectable element and distinguish the two different types of cantilever electrode apparatuses.

As shown in FIG. 8A, the first and second electrical/mechanical contacts 1615, 1617 can be connected by a detectable electrical element 1646. In some embodiments, the detectable electrical element may be a capacitor or capacitive element that is chosen so that at frequencies within the neurostimulation operating frequency range (e.g., at frequencies below about 18 kHz, below about 20 kHz, below about 25 kHz, below about 30 kHz, etc.) the capacitor or capacitive element behaves like an open circuit and therefore does not interfere with the application of the ensemble waveforms to the user. At higher frequencies (e.g., above about 18 kHz, above about 20 kHz, above about 25 kHz, above about 30 kHz, etc., and particularly in the MHz range), the capacitor or capacitive element has a characteristic response that can be sensed by the detection circuitry in the neurostimulator.

For example, in FIG. 8A, which illustrates one example of an "energy" electrode apparatus that may be used to evoke an energy effect as described above, the electrically detectable element may be a capacitor 1646 with a capacitance 180 pF (or any capacitor having a capacitance of between about 10 pF and 2 nF, e.g., 10 pF, 100 pF, 200 pF, 300 pF, etc.). In contrast, the electrode apparatus shown in FIG. 8B, which may describe a "calm" type of electrode apparatus, may have a different electrically detectable element 1646', such as a capacitor with a second capacitance of 680 pF (any capacitance between about 20 pF and 2 nF, e.g., 20 pF, 200 pF, 400 pF, 600 pF, 800 pF, etc.). In FIG. 8B, the electrically detectable element 1646' is also connecting the two electrical contacts 1615' and 1617' that each connect to an active region on the back of the electrode apparatus. The capacitance of the second capacitor can be any value that is distinguishable by the detection circuit, for example, the capacitance of the second capacitor can be two times, three times, four times larger than the capacitance of first capacitor.

Figure 9A:
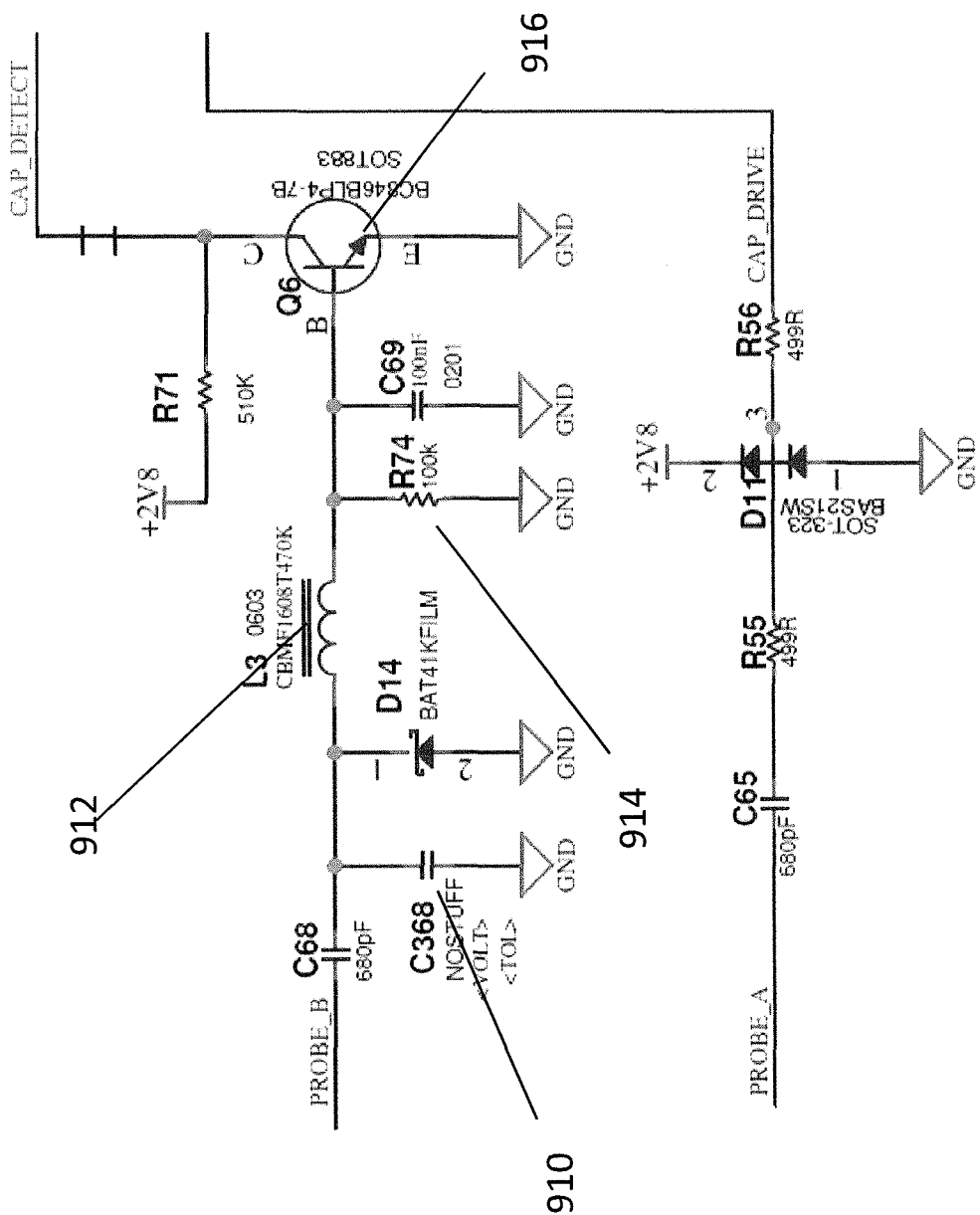
FIG. 9A is one embodiment of a detection circuit that may be used to detect connection and/or the type or identity of an electrode apparatus; the detection circuit may be included on a neurostimulator to detect some variations of the electrode apparatuses described herein.

FIG. 9A illustrates one embodiment of a detection circuit that may be used (e.g., included in a neurostimulator) to determine if an, and what type of, electrode apparatus is attached to the neurostimulator. In this example, the probe A and probe B portions communicate with the first and second contacts, respectively, on the electrode apparatus to which the neurostimulator is attached. Probe A acts as the drive line to the capacitor or capacitive element on the electrode assembly (which may be referred to as a detection capacitor or detection capacitive element) connected between the electrical (or electrical and mechanical, e.g., snaps) connectors of the electrode apparatus, while probe B includes the capacitive detection circuit. The capacitive detection circuit can be an RLC resonant circuit (the letters R, L and C can be in other orders) including a resistor, an inductor, and a capacitor, connected in series. The RLC resonant circuit can form a harmonic oscillator for current and resonate at the resonance frequency. The resonance frequency can be defined as the frequency at which the impedance of the RLC resonant circuit is at a minimum. The resonance frequency in a series resonant circuit has the value of:

$$\omega_0 = \frac{1}{\sqrt{LC}}$$

The capacitive detection circuit of the neurostimulator shown in FIG. 9A may be connected to a microcontroller or other logic circuit to detect a signal (i.e. voltage) indicating resonance of the circuit. The microcontroller or other logic circuit may also incorporate a clock or other timing circuit. The presence and/or amplitude of resonance can be used to distinguish the different type of electrode apparatus in some embodiments. The latency at which resonance begins can be used to distinguish the different type of electrode in some embodiments.

In some other embodiments, as shown in FIG. 9A, the capacitive detection circuit can include a capacitor 910 (C368) and an inductor 912 (L3) in parallel. The resonant frequency of the LC circuit is defined by the capacitance of the capacitor 910 and the inductance of the inductor 912. When the frequency is the resonant frequency of the RL circuit, the charge over the node B of the transistor 916 can accumulate quickly. The transistor 916 can begin to conduct, and the node C of the transistor 916 can switch from status "0" to "1". The capacitance of the capacitor or capacitive element on the electrode assembly connected between the electrical connectors of the electrode apparatus (e.g., 1646 in FIG. 8A or 1646' in FIG. 8B) can affect the time for the node C of the transistor 916 to switch. By measuring the time for the node C of the transistor 916 to switch, the capacitive detection circuit can determine what type of electrode apparatus is attached to the neurostimulator. The detection circuit to detect the capacitor or capacitive element can have high sensitivity by using the resonant circuit. The detection circuit can detect the small difference in capacitance. For example, the detection circuit can detect the difference in capacitance when the first capacitance is 2 times, 3 times, or 4 times larger than the second capacitance in some embodiments. The detection circuit can detect the difference in capacitance when the difference between the first capacitance and the second capacitance is larger than 50 pF, 100 pF, 200 pF, 300 pF, 400 pF, and 500 pF in some embodiments.

Figure 9B:
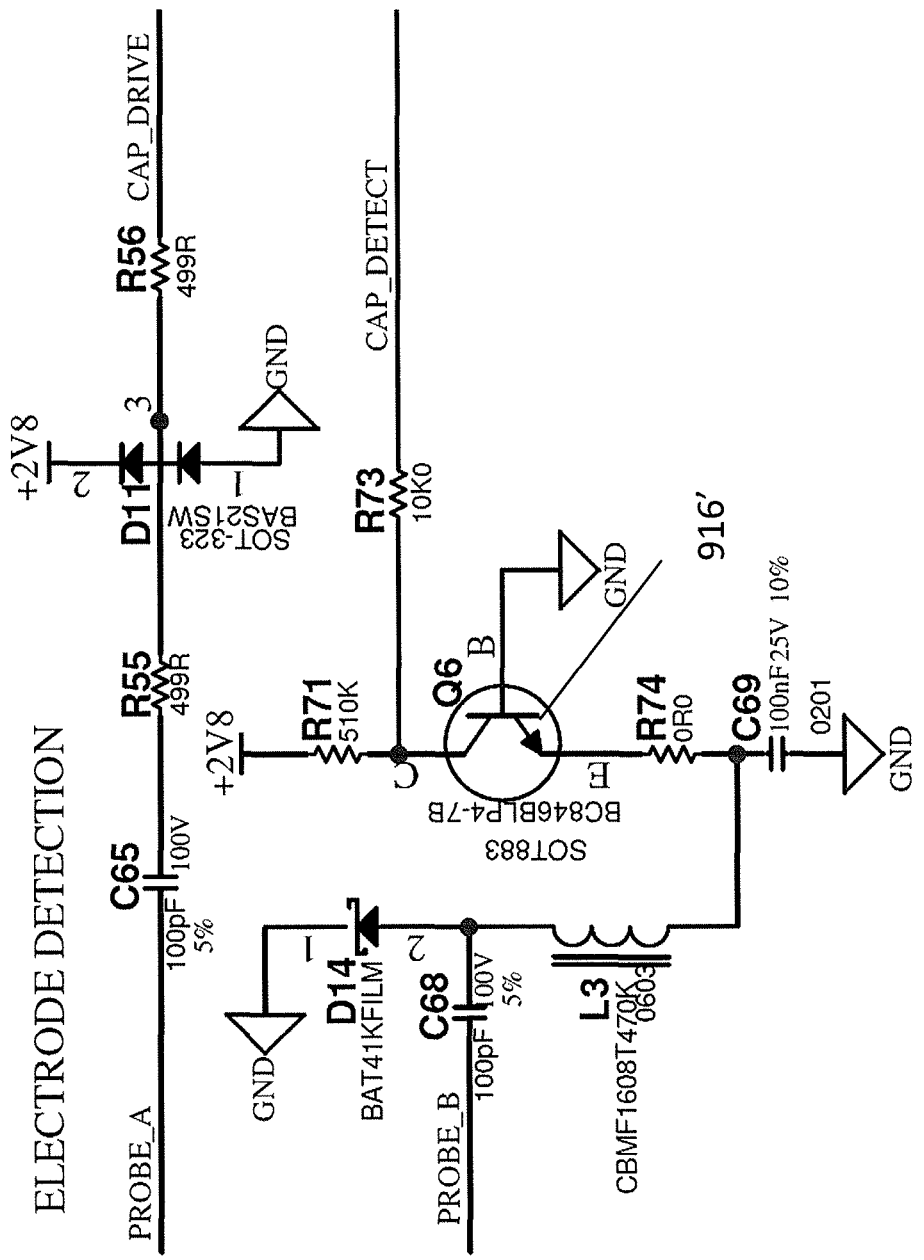
FIG. 9B is another embodiment of a detection circuit on a neurostimulator that may be used to detect connection and/or the type or identity of an electrode apparatus.

FIG. 9B illustrates another embodiment of a detection circuit that may be used to determine if an, and what type of, electrode apparatus is attached to the neurostimulator. Similar to the embodiment in FIG. 9A, the probe A and probe B portions communicate with the first and second contacts on the electrode apparatus to which the neurostimulator is attached. Probe A acts as the drive line to the capacitive element (e.g., 1646 in FIG. 8A or 1646' in FIG. 8B), while probe B includes the capacitive detection circuit. The capacitive detection circuit can be another RLC resonant circuit, a slight variation of the embodiment shown in FIG. 9A. When sweeping the frequencies at frequencies higher than the neurostimulation operating frequency range, the RLC circuit can have resonance at the resonant frequency. Therefore, the detection circuit can determine the type of electrode apparatuses attached to the neurostimulator.

Figure 9C:
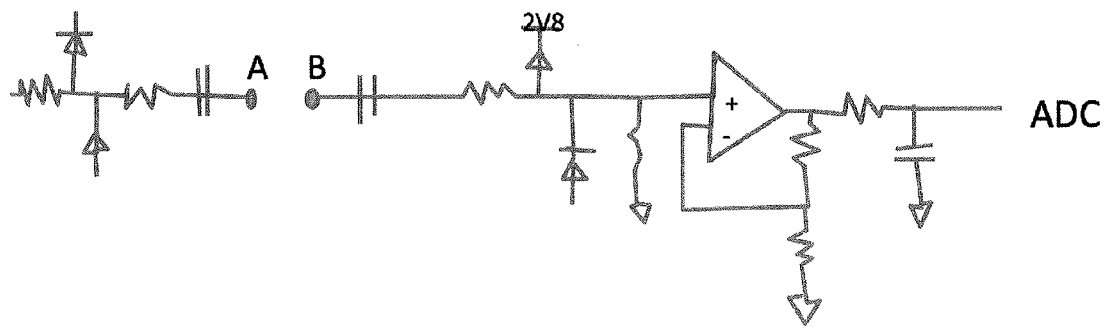
FIG. 9C is yet another embodiment of a detection circuit that may be used to detect connection and/or the type or identity of an electrode apparatus.

FIG. 9C illustrates a circuit using a pulse to detect the capacitor on the electrode apparatus in another variation of a capacitance detection circuit that may be used to uniquely identify an electrode apparatus. The embodiments shown in FIG. 9A and FIG. 9B are based on a resonant circuit to detect the capacitor or capacitive element on the electrode apparatus. Alternatively, a capacitor detection circuit may use a pulse to detect the capacitor or capacitive element on the electrode apparatus. As shown in FIG. 9C, the pulse may be generated by a controller output coupled to the circuit. The pulse may propagate through the circuit including the capacitor or capacitive element on the electrode apparatus (for e.g., 1646 in FIG. 8A or 1646' in FIG. 8B), the response may be affected by the capacitor or capacitive element. By measuring the response, the detection circuit can determine the type of electrode apparatus attached to the neurostimulator.

Figure 19A:
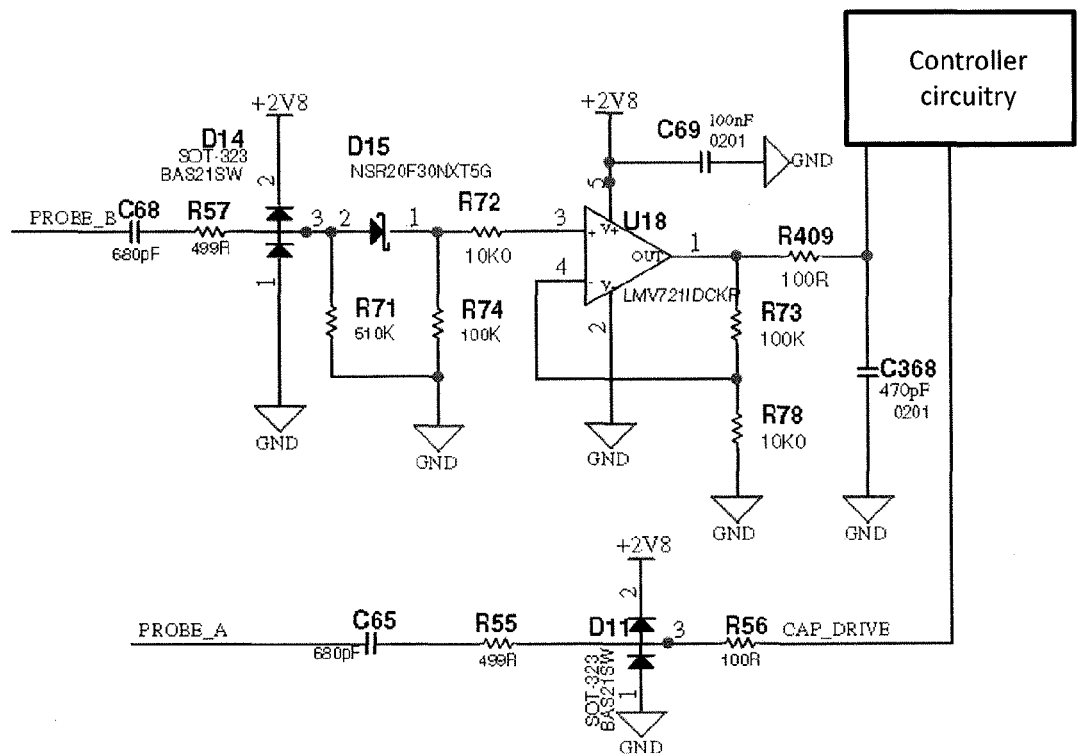
FIG. 19A is another example of a capacitance detection circuit to identify different electrode apparatuses connected to the neurostimulator apparatus.
Figure 19B:
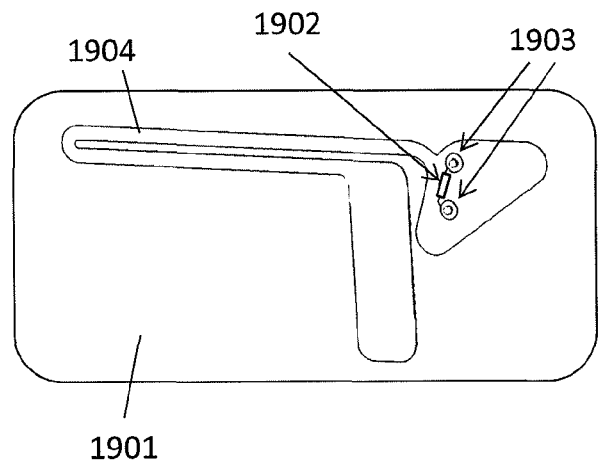
FIG. 19B is an example of an electrode assembly including a capacitor between the connectors to each of the two electrodes of the electrode assembly.

FIGS. 19A-19B also illustrate another example of a capacitance detection circuit that may be used to identify different types of electrode apparatuses once they are connected to a neurostimulator apparatus as described herein. FIG. 19A illustrates one example of the circuit that may be used. In FIG. 19A, the circuit acts by examining pulse length, e.g., the time required for the pulse to decay below a threshold. In FIG. 19A, the circuit includes two capacitors in the test circuit that, when placed in series with the capacitor in the electrode assembly, allows a pulse of signal transmitted between the electrodes (probe A and probe B) to decay at a rate that is characteristic and dependent on the capacitor in the electrode assembly. The detection circuit detects the time that the pulse returned through the electrode assembly remains above a threshold (e.g., non-zero threshold), and compares to an expected value (e.g., within the controller, or via a comparator). In FIG. 19A, the controller is configured to directly read the value of the returned pulse and determine the time above threshold. This is possible in this example because although the returned signal is mostly a decaying exponential, when the amplification gain is high, the pulse is saturated. Although the exponential size of the pulse returned is on order of 2.8V, the amp wants to amplify it to 28V, however because it is limited to 2.8V from the power supply, the signal is saturated to this value.

Thus, in this example, the three capacitors are connected in series and the decay time of the pulse will be based on the value of the three capacitors, two of which are constant (in the circuit). Depending on the value of the capacitor in the electrode assembly, the time to pass below a threshold will be different for different capacitors.

Figure 19C:
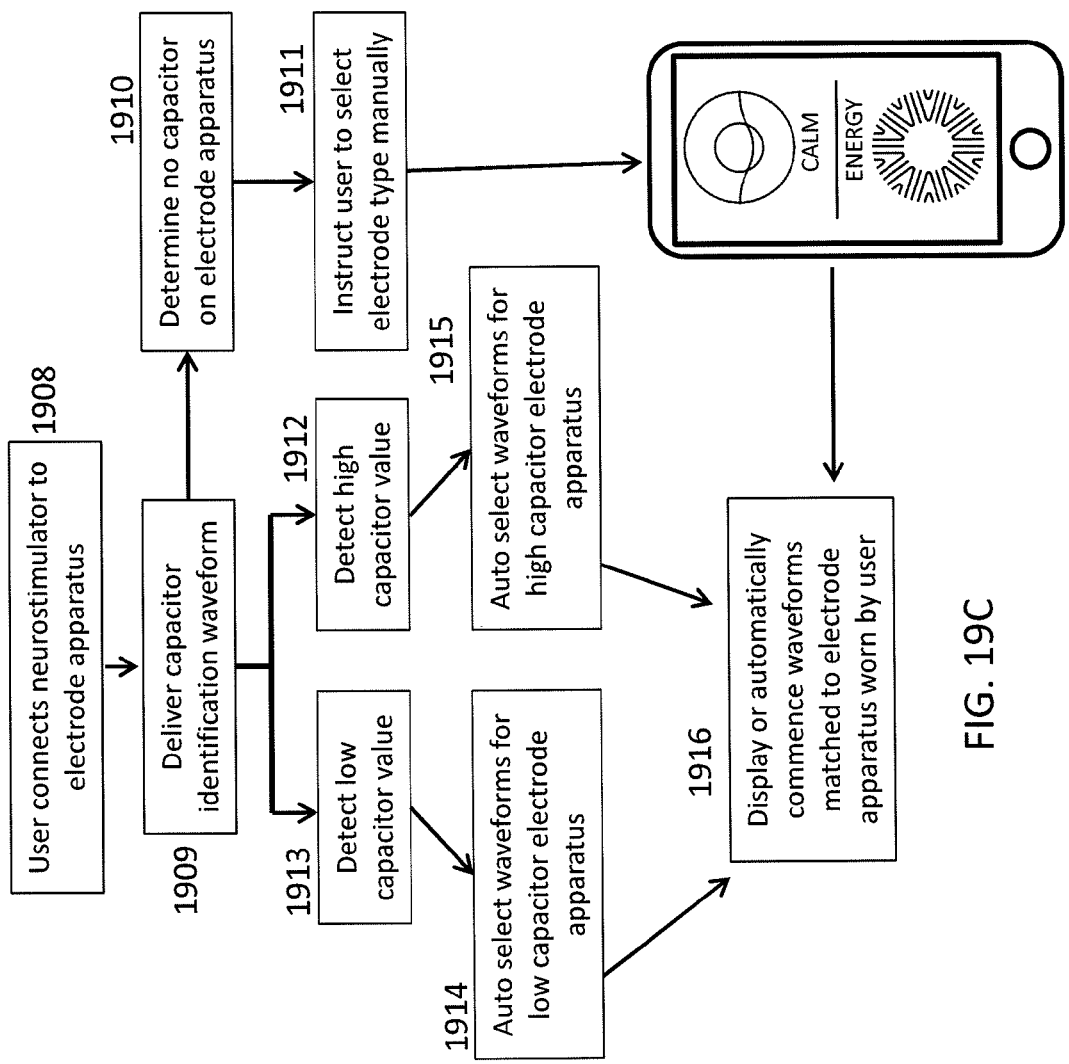
FIG. 19C is a flow diagram illustrating a method of determining the identity of different types of electrode apparatuses to which an electrical stimulator (e.g., neurostimulator) is attached.

FIG. 19C shows an example of a workflow for distinguishing a plurality of electrode strip types (electrode assembly 1904, shown in FIG. 19B). Electrode assembly 1904 may be held on a non-conductive (or minimally conductive) releasable liner 1901 to which the adhesive may be attached until it is removed and placed on the skin (it may be returned to the adhesive liner later). The electrode assembly in this example includes two connectors (snaps 1903) on a first (outwardly-facing, away from the user) side of the electrode assembly for connecting to snap receptacles on a neurostimulator apparatus, such as shown in FIGS. 1B and 3A-3F. In general, two (or more) types of electrode assemblies may be distinguished by detecting the value of a capacitor on the electrode assembly as discussed above and shown in, e.g., FIGS. 8A-8B that shorts between the two snaps on the electrode apparatus. The neurostimulator apparatus may include detection circuitry including or working with a controller that controls a current source. The detection circuitry for detecting the value and/or the presence of a (shorting) capacitor on the electrode apparatus, and the controller may also contain a wireless communication module for communicating with an 'app' running on a personal computing device. When the electrode assembly and the neurostimulator apparatus are connected (e.g., via the snaps and snap receptacles), the neurostimulator apparatus may be adherently worn on a subject's head and/or neck for delivering transdermal electrical stimulation to cause a cognitive effect as described above.

In FIG. 19C, showing an example workflow, a user connects the neurostimulator to the electrode apparatus (e.g. via snap receptacles and snaps). Software (and/or firmware) running on the neurostimulator module may be configured to detect when an electrode apparatus is electrically (and mechanically) connected and deliver capacitor identification waveform 1909. In the exemplary flowchart shown in FIG. 19C, the apparatus is configured to determine between one of two possible electrode apparatuses (e.g., between two different capacitor values). The capacitor-detection circuit and control logic on the neurostimulator apparatus may determine if there is no capacitor on the electrode apparatus 1910 (in which case it may prompt the user), or if it detects a low 1913 or high 1912 capacitor value on the electrode apparatus. The capacitor-detection circuit and control logic on the neurostimulator apparatus may also determine whether the electrode assembly and neurostimulator apparatus are adhered to the subject's head or head and neck, though in some variations it may not be possible to reliably distinguish between different capacitor values of electrode assembly sub-types when the assembly is adhered to the subject's skin due to the relatively high capacitance of the body.

In some variations, when the capacitor identification circuit (detection circuit) determines that no capacitor is present (e.g., shorting the snaps of the electrode apparatus), the system may enter a locked state that disables electrical stimulation. This functionality may be beneficial for improved safety so that a user may not use the neurostimulator module to deliver transdermal electrical stimulation with an inappropriately configured electrode apparatus. Alternatively, absence of a capacitor on the electrode apparatus may trigger a user interface on a personal computing device (smartphone, laptop, desktop, pad, etc., that is communicating with the neurostimulator apparatus) to provide a selection screen to be shown so that a user may select an appropriate waveform type matching an electrode apparatus type connected to the neurostimulator apparatus 1917 (e.g. allowing selection between one of two types of electrode assemblies, such as a "Calm"-type waveform, by tapping the top half of the screen, or an "Energy"-type waveform by tapping the bottom half of the screen).

Alternatively, if the neurostimulator apparatus detects a low capacitor value 1913, it may transmit this information wirelessly to the user computing device which may automatically select waveforms that are appropriate for the type of electrode assembly that correspond to the low capacitor value shorting the electrode connector snaps 1914 and may also display a user interface for selecting a specific waveform from the matching type via pull-down menu 1919, and controlling the commencement, intensity, modulation, pausing, or stopping of a transdermal electrical stimulation waveform for inducing a cognitive effect 1919. A similar workflow and functionality may occur for the detection of high capacitor value 1912 for automatic selection of waveforms appropriate for the electrode assembly type that corresponds to the high value capacitor, and may provide a user interface allowing the selection of appropriate waveforms to match this electrode type or auto-selection and commencement of an appropriate waveform, as well as the control of the starting, stopping, and intensity of the waveform 1916.

FIGS. 9A-9C and 19A-19B are examples of sensing circuitry that may be used to detect the capacitor or capacitive element on the electrode apparatus. The detection circuit of the neurostimulator may be connected to a microcontroller or other logic circuit. The microcontroller or other logic circuit may also incorporate a clock or other timing circuit. In some embodiments, the capacitor detection circuit may include a RLC resonant circuit. In general, sensing circuitry based on a RLC resonant circuit may identify the capacitor or capacitive element on the electrode apparatus by applying high-frequency current between the electrical connections (anodic, cathodic) of the electrode apparatus. In some alternative embodiments, the capacitor detection circuit may generate a pulse, and determine the type of electrode apparatuses attached to the neurostimulator by measuring the response (e.g. duration of a signal) after the pulse propagates through the capacitor or capacitive element on the electrode apparatus.

A variety of different detection circuits (electrode assembly detection/identification circuit) may be used as part of the neurostimulator apparatus, and the electrode detection circuits are not to be limited to the examples discussed above. In some embodiments, both types of electrode assemblies may include capacitors or capacitive elements with different capacitance. In some other embodiments, only one electrode apparatus may include a capacitor or capacitive element. In some alternative embodiments, other electrically detectable elements, such as a resistor or an inductor may be included in both types of electrode assemblies, or in only one type of electrode assembly; the detection circuit can be configured to detect the electrically detectable element. In some other embodiments, a switch may be included in the detection circuit, which can be configured to be turned on when one type of electrode apparatus is used and turned off when the other type of electrode apparatus is used.

FIG. 20 shows data taken from three types of exemplary electrode assemblies: a first set that does not include a capacitor (e.g., a capacitor between the electrical connectors as shown in FIGS. 8A-8B), referred to in FIG. 20 as "sticker no cap."; a second set that includes a 180 pF capacitor on the electrode assembly between the connectors (electrodes); and a third set that includes a 680 pF capacitor on the electrode assembly between the connectors (electrodes). These different sets may correspond to different types of electrode assemblies, such as electrode assemblies specifically designed to be used to induce different cognitive effects. For example, an electrode assembly used to induce a "calm" cognitive state may include a capacitor having a first value (e.g., 680 pF) that connects between a first electrode to attach at the user's temple/forehead region and a second electrode to be worn at the back of the user's neck, such as the electrode assembly variation shown in FIGS. 4A-6 and 8B. Another type of electrode assembly, such as the one shown in FIGS. 7A-8A, may be configured to be used for inducing a cognitive state of enhanced energy, and may include a capacitor having a different value (e.g., 180 pF) that connects between a first electrode to be attached to the user's temple/forehead and a second electrode that attaches behind the user's ear. In this example, there is a rather large and detectable distinction between these different configurations of electrode assemblies, including a large distinction between electrode assemblies that have no capacitor. Notwithstanding the large and detectable difference between the electrode assembly types having different capacitor values, the measured values may include unaccounted variability, such that the distribution of durations measured for a capacitive element with a first value (capacitance) may overlap with the distribution of durations measured for a capacitive element with a second value (capacitance). To improve the reliability of electrode assembly type detection based on capacitance differences of capacitive elements on the electrode assembly, an algorithm may be applied that samples multiple values and applies a statistical algorithm (e.g. calculating an average, calculating a median, requiring that n consecutive measurements be classified as the same electrode subtype (where n may be two measurements, three measurements, four measurements, five measurements, or more measurements), etc. In general, ongoing, sequential measurements of the electrode assembly capacitance by the circuit may continue until a statistical threshold is reached (e.g. according to an algorithm such as those listed above). In addition, the apparatus may readily detect when no electrode has been attached ("no sticker"). The data shown represents the number of clock cycles for a 12 MHz clock (about 83 nanoseconds) occurring during a pulse detection period, when the electrode assembly ("sticker") is not yet attached to the subject. These values may be different when the electrode assembly is attached to the user, and the capacitive detection circuit (and/or controller) may detect these different values to determine if the electrode assembly is attached to the user, and guide the user in confirming the type of electrode assembly connected or to be connected, as described above.

Alternatively or additionally, in some variations, an electrode assembly such as the cantilever electrode apparatuses described herein may include active circuitry such as a surface mounting chip to identify the electrode apparatus and/or for security. For example, when the electrode apparatus includes a substrate that is a flex circuit, the circuitry may be configured to provide a unique identifier, and/or a counter that may increment with use(s).

Any of the electrode assembly embodiments described herein may additionally or alternatively include an identification tag (e.g., a near-field identification tag) configured to designate the electrode assembly type (e.g., energy, calm) and/or other identifying information or use information about the electrode assembly. An identification tag may be disposed on a surface of the substrate, for example, on an outer (not skin-facing) surface of the substrate, or on a connector physically coupled to the substrate. Any suitable identification tag(s) may be used, for example, a Bluetooth transmitter, a Bluetooth Smart beacon, an RFID tag, a near-field communication tag, a resistive element, a capacitive element, a microcontroller, and/or a visual identifier such as a bar code, a QR code, a light transmitter, or an image. The identification tag may serve to identify one or more characteristics of a particular electrode assembly. For example, the identification tag may uniquely identify an electrode assembly's: model (e.g., calming effect, energizing effect, or focusing effect), brand, manufacturer, date and/or time of manufacture, physical size (e.g., small, medium, or large), security tag, or stimulation capacity (for example, as determined by the amount of Ag and Ag/AgCl and/or hydrogel present in the electrode assembly).

As described above in reference to a capacitive element for identification of the electrode assembly, an electrical stimulation system may be adapted for use with an identification tag of an electrode assembly. Further, any of the controllers that may be used with the neurostimulators described herein may be configured to recognize (and the electrode assembly and marker may be configured so as to be recognizable) by a controller, e.g., a specialized remote control, smartphone, tablet, etc. In some such variations, the controller may include an electronic reader, electronic receiver, or image reader configured to detect and recognize the identification tag. In some variations the neurostimulator may pass along the identifying information to the controller specifically (i.e. may both read and write to the identification tag). For example, in one embodiment of the system, the controller includes a Bluetooth receiver, and the electrode assembly includes a Bluetooth transmitter or Smart beacon; in another embodiment, the controller includes an RFID reader, and the electrode assembly includes an RFID tag. In another embodiment, the controller includes a near-field communication antenna, and the electrode assembly includes a near-field communication tag. Additionally or alternatively, the controller may include an electrical connector and resonating circuit, such as a series of electrical pins, and the electrode assembly may include a resistive element or a capacitive element.

In one embodiment of a system including an electrode assembly, the electrode assembly and the controller (and/or the neurostimulator) each includes a microcontroller (e.g., a microprocessor or a programmable chip) programmed with firmware. The firmware, when run, allows for one-way or two-way communication between the coupled microcontrollers and further allows the microcontrollers to run an authentication protocol to query and confirm that the controller and the electrode assembly are authentic and authorized for use together.

In another embodiment, the controller (and/or neurostimulator) may include an image reader configured to detect a visual identification tag, and the electrode assembly may include a visual identification tag. In some embodiments, the image reader includes an image capturing mechanism (e.g., a camera, a lens, a bar code reader, a QR code reader, or a diode) and a microprocessor, and the visual identification tag of the electrode assembly includes: a bar code, a QR code, a light transmitter, an image, or other visual identifier.

The controller and/or neurostimulator of various embodiments may be programmed such that, if the controller cannot recognize the identification tag of an electrode assembly, the controller will not provide a stimulating current to the electrode assembly. For example, if a controller is communicatively coupled to an electrode assembly having an unrecognized identification tag (or lacking such a tag), the controller may render the coupled electrode assembly inoperable. No stimulating current will be delivered to the electrode assembly. In such a manner, the electronic identification tag may prevent the system from operating with unauthorized electrode assemblies and thus ensure safe operation of the system.

In some embodiments, when a controller and/or neurostimulator is communicatively coupled to an electrode assembly having an identification tag, the microprocessor of the controller and/or neurostimulator may compare the detected identification tag to a database of identification tags stored in a memory to confirm that the detected identification tag matches a known identification tag. Additional electrode-specific information may be stored in the database with each known identification tag, such as, for example: the appropriate stimulation protocol for the respective electrode, acceptable threshold levels (e.g., temperature, pH, and/or current values), acceptable operating parameters (e.g., temperature, humidity, etc.), and the like. In other embodiments, the microprocessor of the controller and/or neurostimulator may transmit data indicative of the detected identification tag to a remote server where a database of known identification tags is stored, and the remote server may compare the detected identification tag to the known tags, and if there is a match, transmit data associated with the known tag back to the controller. With the information obtained from the database, the controller and/or neurostimulator may test the electrode assembly and current conditions to confirm the electrode(s) are still within acceptable operating specifications (e.g. temperature, humidity, force, etc.); the controller may then deliver a programmed stimulation protocol to a user appropriate for the operating conditions of the electrode assembly.

For example, the neurostimulator, a user computing device, or a remote server connected via, e.g., the Internet, may in a first step store information about a specific electrode assembly unit (unique identifier contained in the detected information of the tag) associated with information about the electrical stimulation delivered. If the same electrode identifier is detected by that neurostimulator (or another neurostimulator connected via the Internet to a database storing information about the previous use of that electrode assembly unit), the duration, intensity, or another quality of stimulation may be adjusted to ensure efficacious and comfortable delivery of an electrical stimulation waveform for inducing a cognitive effect. For example, the detected information from the electrode assembly tag may contain a quantity of consumptive electrode material (i.e. Ag—AgCl layer) and limit use of the electrode to comply with this limit, across one or more electrical stimulation sessions. In general, this information may be stored locally on the neurostimulator device, in a database on a user computing device that communicates wirelessly with the neurostimulator, or in a database on a remote server connected to the neurostimulator (and/or user computing device), e.g., via the Internet.

Figure 10:
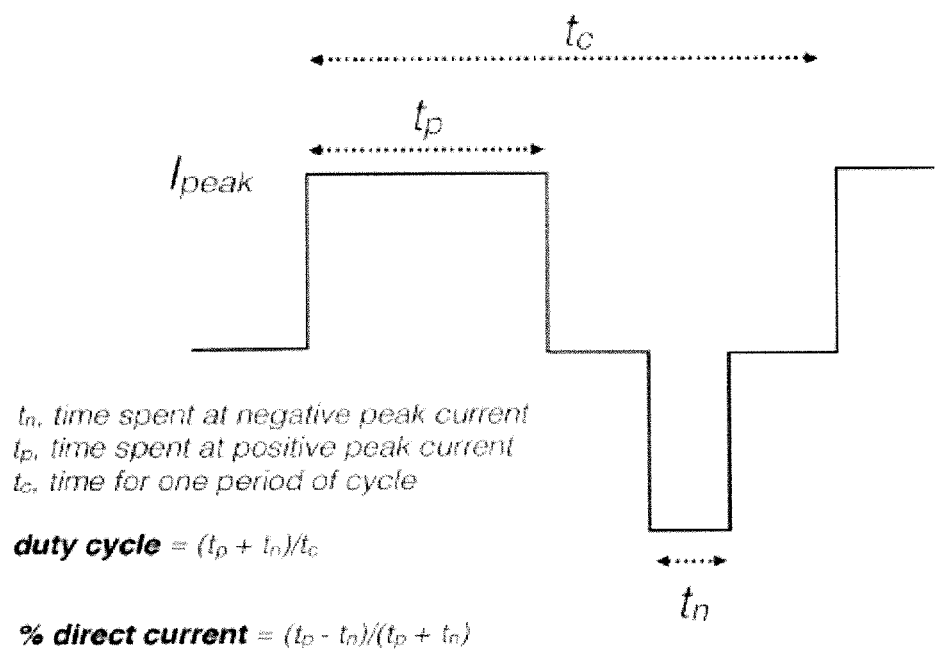
FIG. 10 schematically illustrates a TES waveform according to some embodiments of the disclosure.

FIG. 10 schematically illustrates a TES waveform configured to deliver a biphasic electrical stimulation signal according to various embodiments of the disclosure. In general, a TES waveform may be defined by a duration, direction, peak current, and frequency. In some embodiments, a TES waveform is further defined by a percent duty cycle, percent direct current, ramping or other amplitude modulation, one or multiple frequency components, phase relationship of biphasic current, flat or structured noise, wave shapes (i.e. saw tooth, triangular, sine wave, square wave, exponential, or other wave shape), capacitance compensation features, or other parameters as discussed in U.S. patent application Ser. No. 14/091,121, titled "WEARABLE TRANSDERMAL ELECTRICAL STIMULATION DEVICES AND METHODS OF USING THEM," filed on Nov. 26, 2013, now U.S. Pat. No. 8,903,494, which is herein incorporated by reference in its entirety. A TES waveform may also be defined for bursting wherein one or more cycles of the waveform are repeated at a bursting frequency and with a bursting duty cycle that defines, as a percentage of the bursting frequency, the proportion of the cycle comprising a burst versus a quiescent period.

In some embodiments, the neurostimulator may include a high voltage supply, for example, 30V, 60V, or 80V. TES systems described herein incorporate electronic circuitry to achieve high voltage electrical stimulation, where high voltage corresponds to a circuit supply voltage generally greater than 10 V and optionally greater than 15 V, greater than 20 V, greater than 30 V, greater than 40 V, greater than 50 V, or greater than 75 V. An apparatus for delivering high current stimulation comprises a power source (generally a battery) with rapid discharge properties (e.g. a Li-ion 2C battery of 200 mAh capacity with a maximum charging current of 1C (200 mA), maximum continuous discharge current of 1C (200 mA), and maximum peak discharge current of 2C (400 mA)) so that peak currents can be delivered; a transformer (buck boost or other) to take lower voltage output of a battery or other power source and provide high voltage levels needed to provide the specified power level; and other electronic circuit components designed to operate predictably and reliably at high voltage.

Figure 11A:
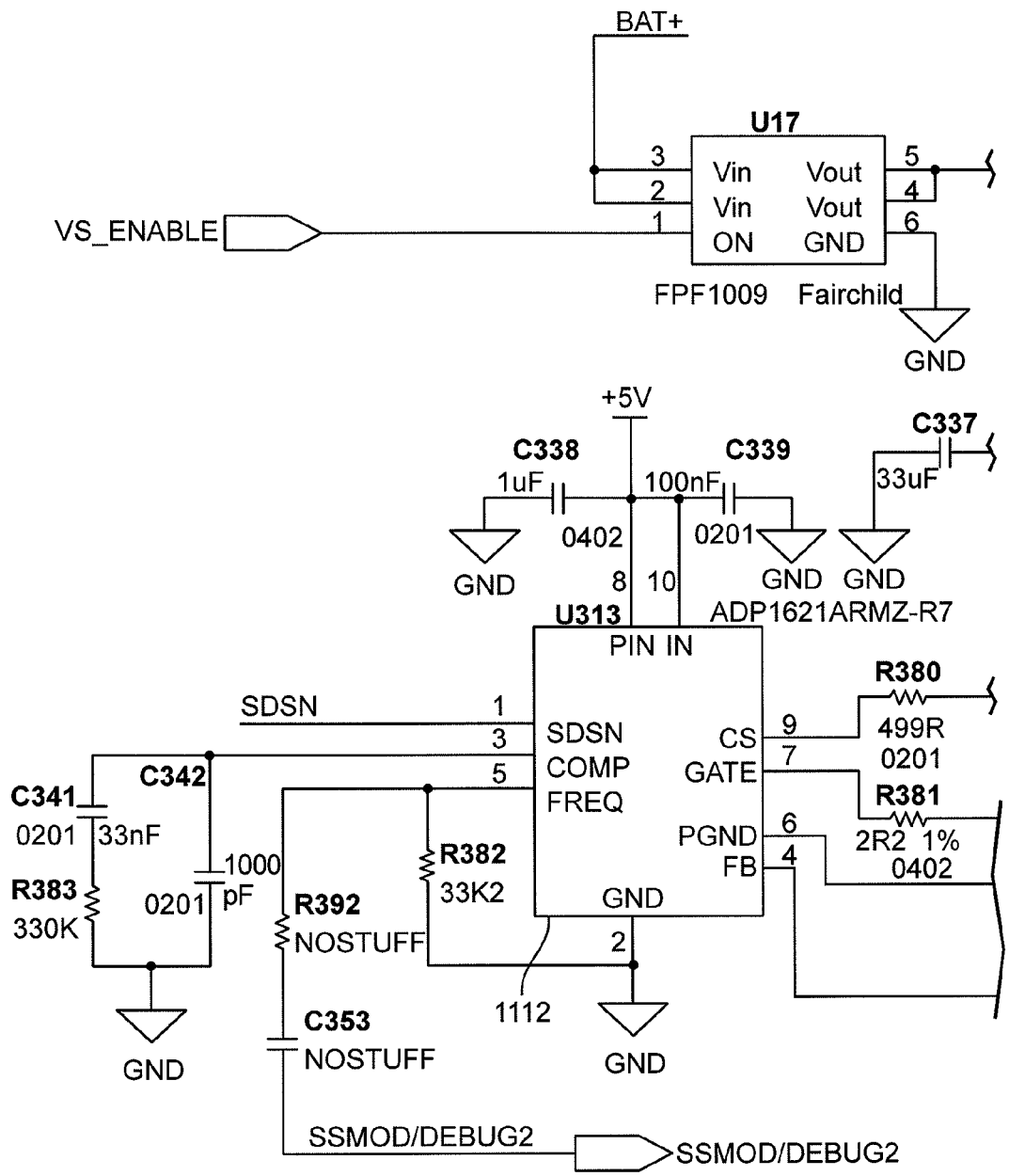
FIG. 11A illustrates a portion of an example of a circuit of a controller of a neurostimulator.
Figure 11A:
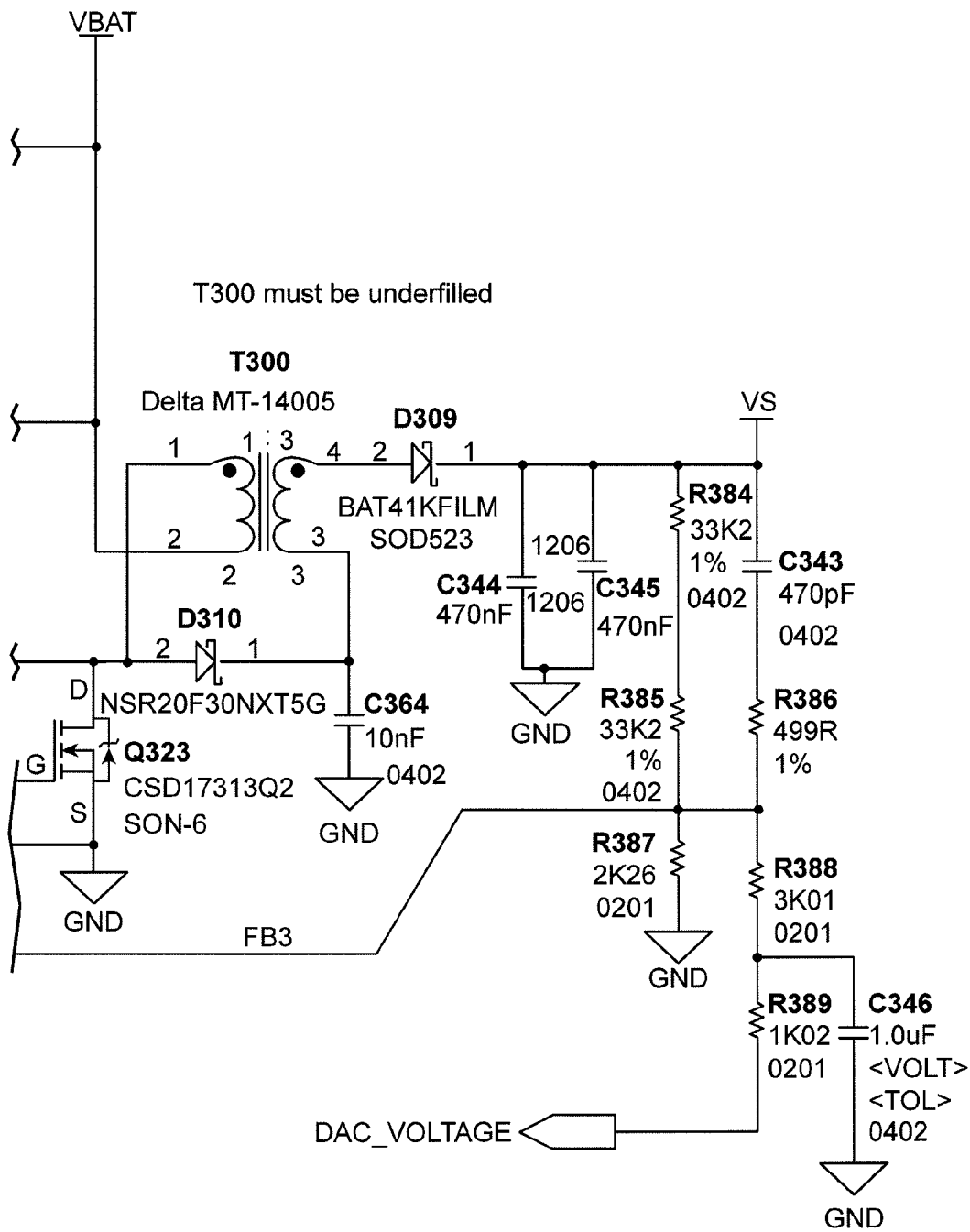
Figures 1, 11B:
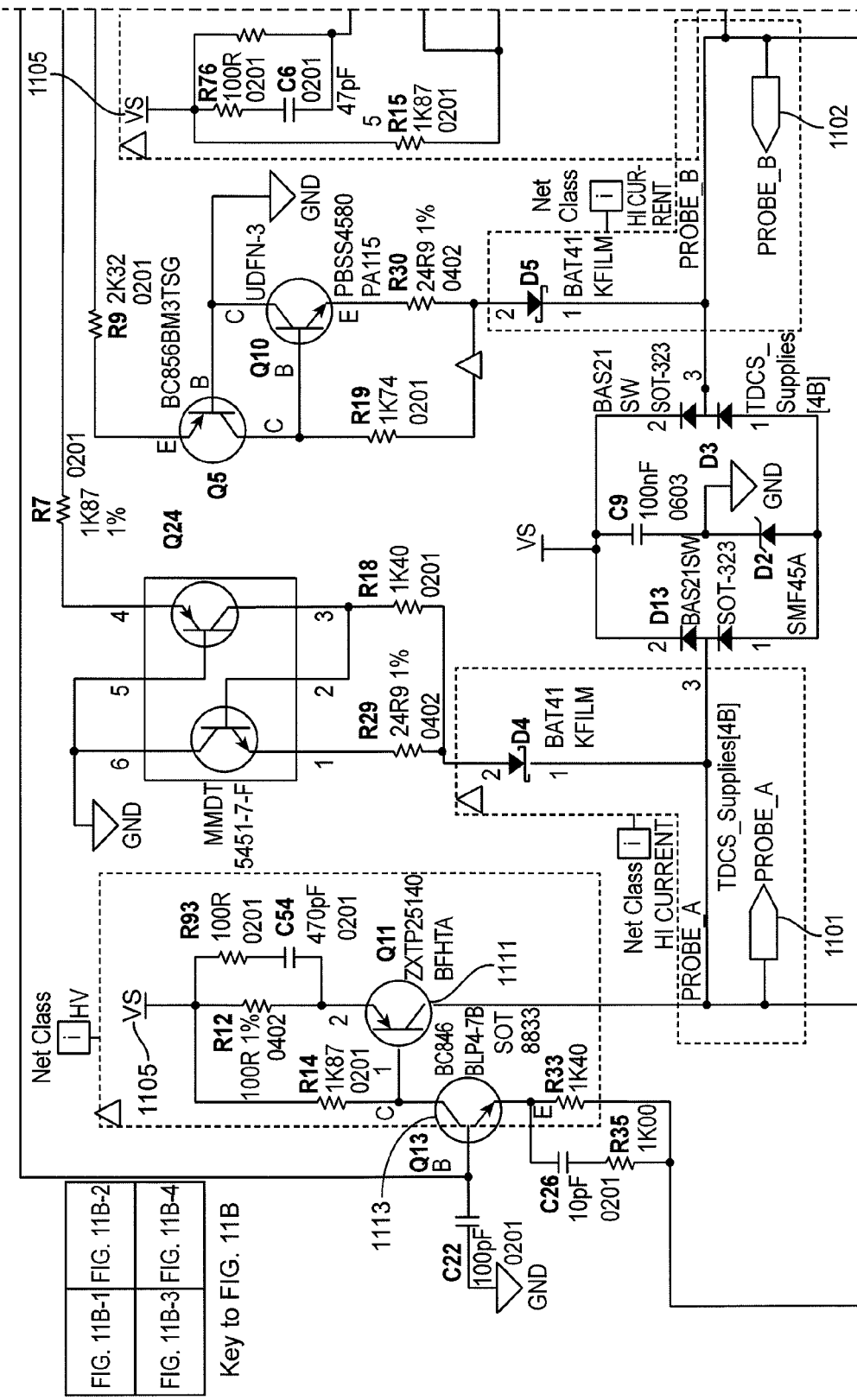
FIG. 11B illustrates another portion of an example of a circuit of a controller of a neurostimulator.
Figures 2, 11B:
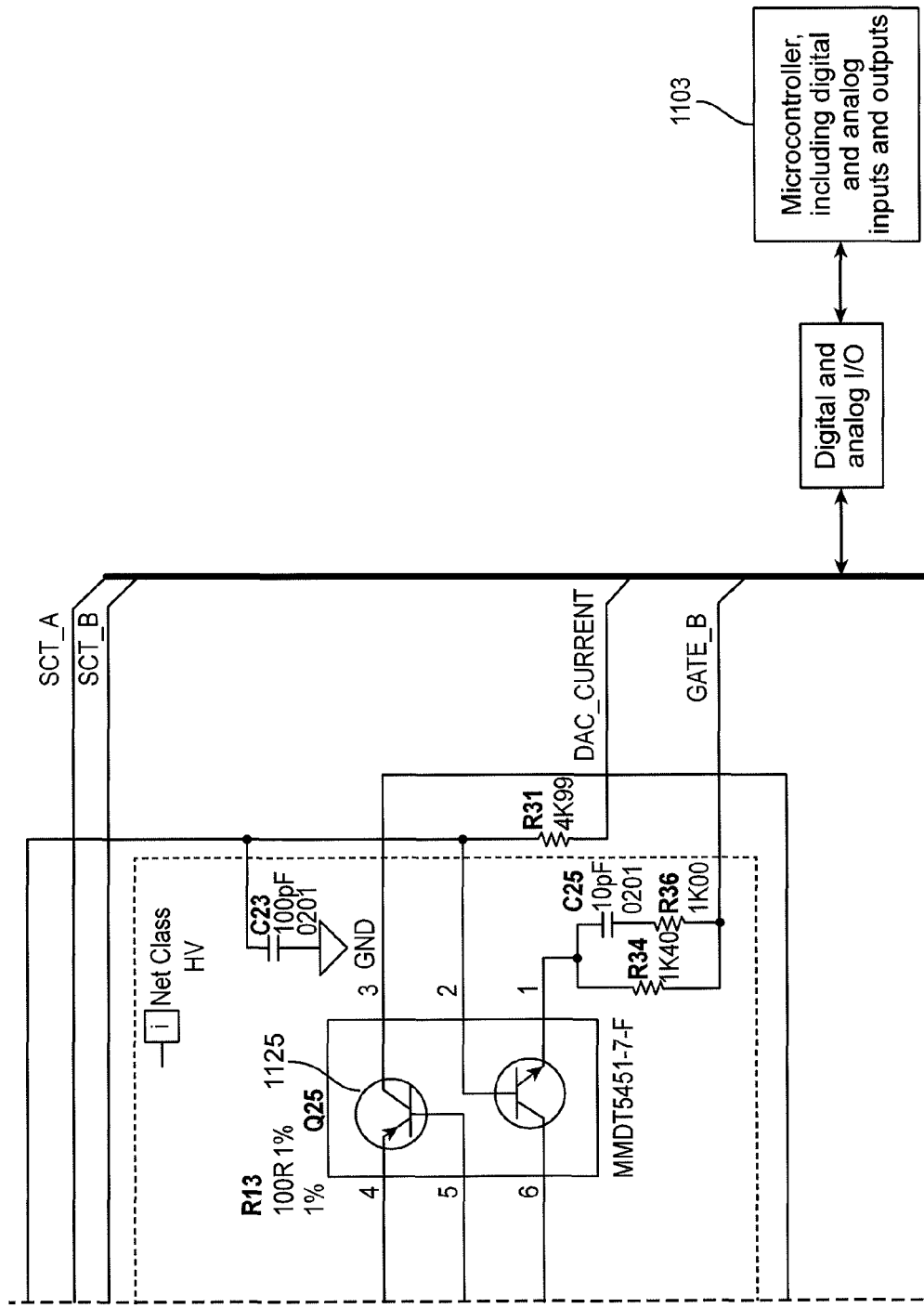
Figures 3, 11B:
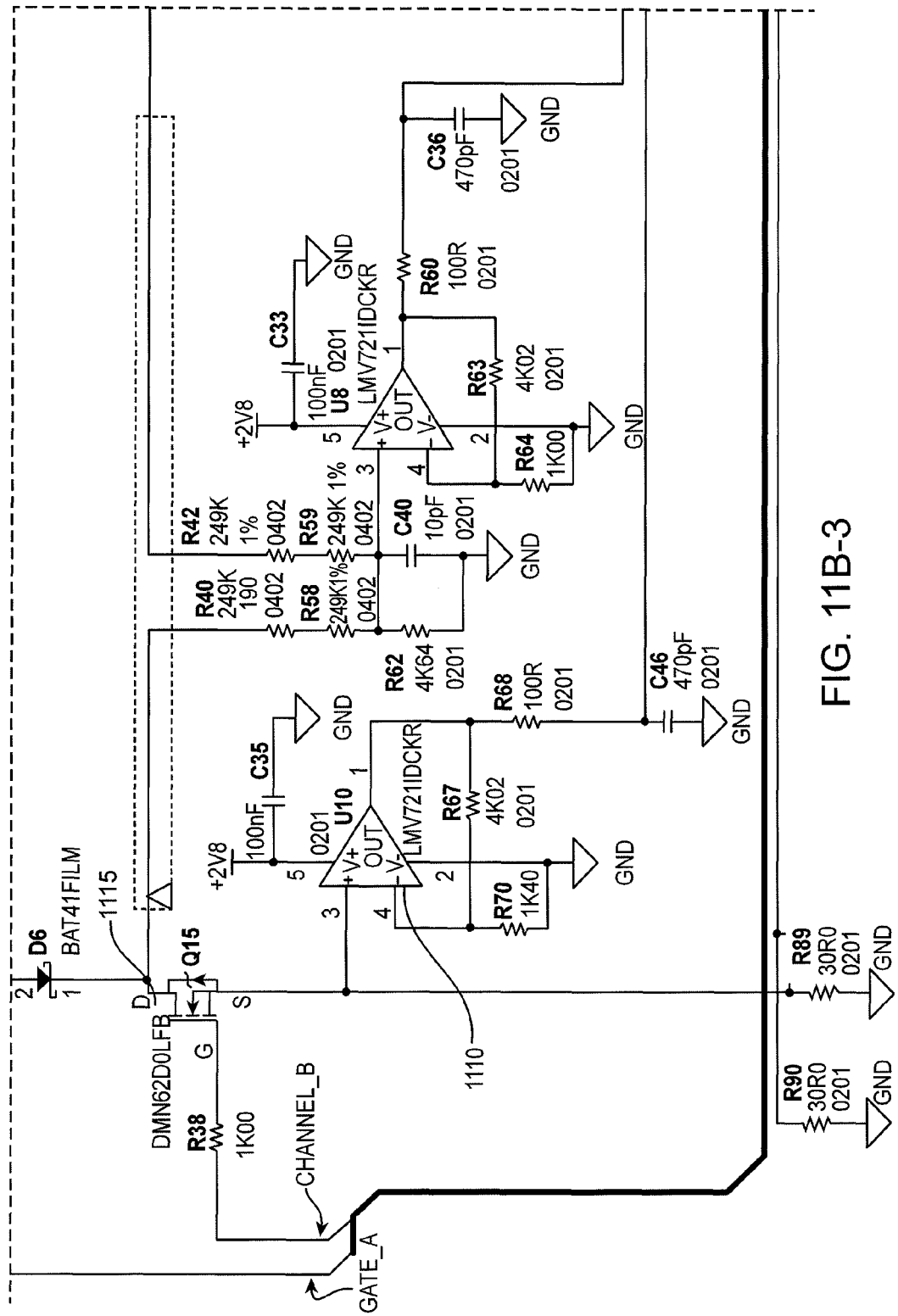
Figures 4, 11B:
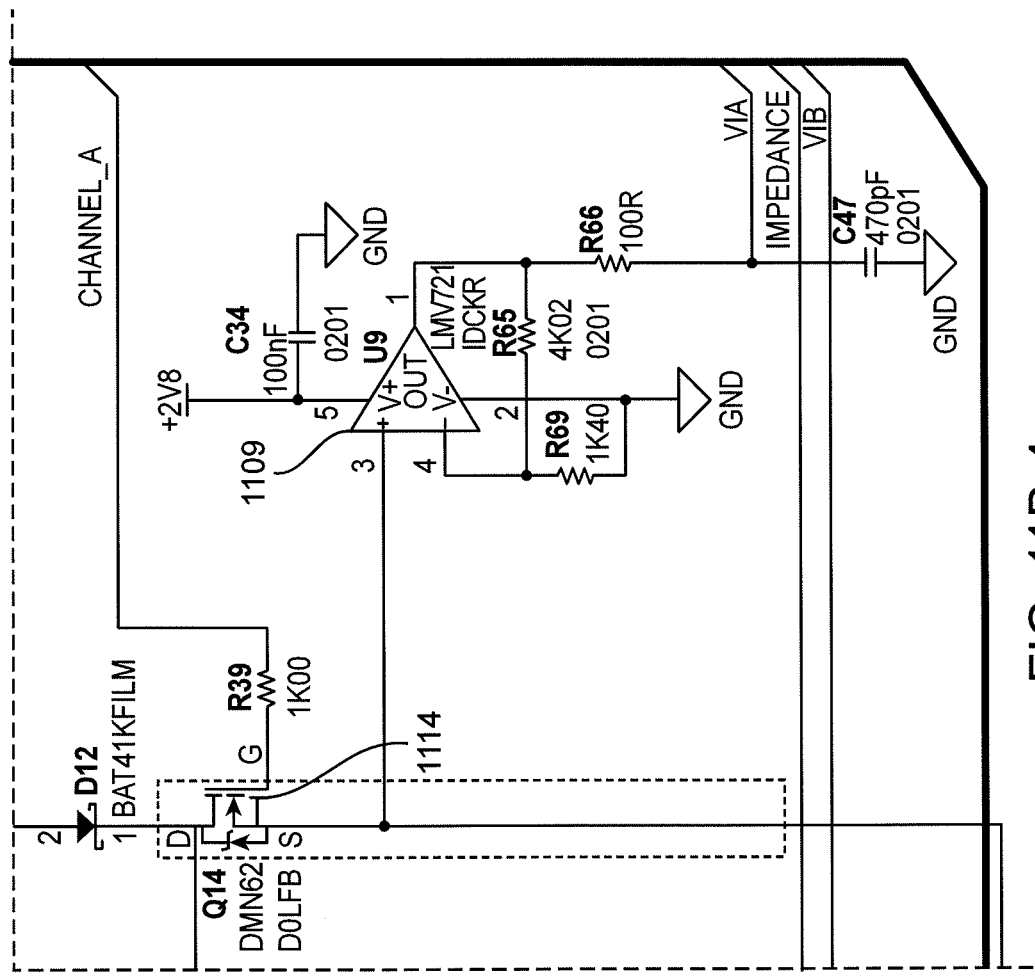

FIG. 11A and FIG. 11B illustrate an example of a circuit of a controller of the neurostimulator configured to adjust an applied voltage. In various embodiments, the controller of the neurostimulator can include a feature to control the applied (or available) supply voltage, Vs, instead of using the maximum available voltage. FIG. 11A illustrates the power supply of the controller. As shown in FIG. 11A, a power converter 1112 can be configured to output the supply voltage, $V_s$, which can be different than the available maximum voltage of the power supply.

For example, FIG. 11B illustrates a circuit including an H-bridge configured to deliver electrical stimulation to a subject and control the applied supply voltage, $V_s$, 1105. In some embodiments, the circuit can be a double H-bridge configuration. In one direction of the outside H-bridge, a transistor 1113 and a transistor 1111 can be configured to generate a first current pulse, which can be a first portion of a TES waveform. The first current pulse can propagate to probe A 1101, to the subject, to probe B 1102, and then propagate to a MOSFET transistor 1114. The first current pulse can be measured by an amplifier 1109, and the measurement can be sent to a microprocessor 1103. The microprocessor 1103 can use the measurement of the first current pulse as a first feedback signal to adjust the applied supply voltage $V_s$ 1105. In the other direction of the outside H-bridge, a pair of transistors 1125 can be configured to generate a second current pulse, which can be a second portion of the TES waveform. The second current pulse can propagate to probe B 1102, to the subject, to probe A 1101, then to a second MOSFET transistor 1115. The second current pulse can be measured by a second amplifier 1110, and the measurement can be sent to the microprocessor 1103. The microprocessor 1103 can use the measurement of the second current pulse as a second feedback signal to adjust the applied supply voltage $V_s$ 1105.

In some embodiments, the circuit may measure and/or calculate the peak voltages delivered to the electrodes. In some other embodiments, the circuit may include other electrical elements to perform the measurements of the peak voltages delivered to the probes. The measured voltage can be used to calculate the effective impedance, resistance, and/or capacitance, then a communication signal can be sent to the microprocessor 1103 of the controller, which may adjust the applied supply voltage $V_s$ 1105 depending on the historical pattern of peak voltages delivered to the probes. In general, the circuit may perform the measurements of the peak voltages delivered to the probes only during positive-going and/or negative-going pulses of the TES waveform.

In some embodiments, the controller can be configured to adjust the applied supply voltages $V_s$ from the historical demand of the peak voltages and/or the applied voltages during the TES stimulation session. The impedance and/or capacitance of skin may be varied during the TES stimulation session. For example, the impedance of the skin may be affected by electrical signal frequencies, local skin temperature, etc. and capacitance on the skin can build up during individual pulses, requiring greater voltage at the end of a pulse than at the beginning for a constant current. Although the maximum available voltage may be high, (for example, 60 V in some embodiments), the applied voltages may be adjusted according to the demand of the user to avoid overheating. In some embodiments, the controller may measure the peak voltages delivered to the probes over several cycles, (for example, 2, 5, 8, or 10 cycles). The measured peak voltages may be used as feedback control signals to adjust the applied voltages. For example, the average measured peak voltage measured over a few cycles (for example, 2, 5, 8, 10, or more cycles) may be some measured value, for example, 10V. The controller may adjust the applied voltage by setting the applied voltage to be 5 V or 7 V over the measured value 10V, thus the overall applied voltage may be adjusted to be 17V, instead of using the maximum voltage of 60 V. This automatic feedback adjustment feature may avoid overheating of the neurostimulator or skin of the user and save electrical energy to improve efficiency and enable longer TES waveforms to be delivered between recharging or replacing the batteries of a neurostimulator.

In order for the transistors 1111, 1113 and 1125 to work properly, the voltage drops between Vs and the upper nodes of the MOSFET transistors 1115 and 1114 can be configured to be in an appropriate working range. In some embodiments, the voltages drops can be 2V, 3V, 4V, 5V, 6V, 7V, 8V or any values therebetween. The applied supply voltage $V_s$ 1105 can be adjusted using the feedback signals to ensure the voltage drops are in the appropriate working range. When the voltage drops are too high, the circuit can adjust the current to reduce the voltage drops.

In general, any electrical stimulators, including in particular (but not limited to) the wearable transdermal neurostimulator apparatuses described herein, may be configured to regulate the power of a wearable transdermal neurostimulator device. The electrical stimulators may be configured with circuitry to deliver biphasic electrical signals between a first electrode and a second electrode. Any of these apparatuses may include a high-voltage power supply that is configured to provide an adjustable supply voltage ($V_s$) and a waveform generator receiving the supply voltage. The apparatus may include control circuitry to adjust the Vs after comparing the available $V_s$ to the voltage needed to drive the current (and/or the voltage actually applied between the electrodes or the connectors configured to connect to the electrodes). This control circuitry may be integrated into the controller of the electrical stimulation apparatus, or it may be discrete circuitry. FIG. 11B, discussed above, illustrates one example of this control circuitry, including an H-bridge configuration to compare a difference between the supply voltage ($V_s$) and the applied voltage ($V_{applied}$) to a target voltage offset, allowing the control circuitry to adjust the supply voltage and increase the supply voltage if the difference between the supply voltage and the applied voltage is below the target voltage offset, or to decrease the supply voltage if the difference between the supply voltage and the applied voltage is above the target voltage offset.

In general, the target voltage offset may be a range of values (e.g., between 1V and 12V, between 2V and 10V, between 3V and 9V, between 4V and 8V, etc., including between any lower value of about 1V, 2V, 3V, 4V, etc. and any upper value of 5V, 6V, 7V, 8V, 9V, 10V, etc.). Although broad ranges of target voltage offsets (e.g., between 1-12V) are possible, in some variations it may be preferable to use a narrower range (such as between 4-6V or other similar ranges), to avoid heating at high end of the range and distortions in waveform at low end of range. In some embodiments, the range may be narrow such that the $V_s$ adjustments are made to target a specific offset voltage (i.e. 4 V, 5 V, 6 V, 6.5 V, 7 V, etc.).

Without control circuitry configured to adjust the supply voltage (Vs) as described herein, the apparatus may heat, and may waste a large amount of the available charge in heat loss. Further, the shape of the waveforms delivered may be less precise, as illustrated in FIGS. 21A-21D. For example, FIG. 21A shows an "ideal" biphasic waveform which may be repeated at a desired frequency, and may be modulated (e.g., amplitude modulated), and controlled to regulate either or both the positive-going pulse and the negative-going pulse for the duration (pulse width), amplitude, and presence (and direction) of any capacitive discharge component. In FIG. 21A, the waveform element is a square-wave, biphasic, charge-imbalanced current, having a positive-going pulse 2103 with a larger duration than the negative-going pulse 2105; no capacitive discharging is shown (examples showing capacitive discharging are shown in FIGS. 12A-12E and 14A-14B, discussed above). FIG. 21B illustrates how this current waveform signal may be distorted if the supply voltage ($V_s$) is not regulated as described herein, particularly when the value of the supplied voltage is close to the value of the applied voltage needed to deliver the desired current (which may vary with skin impedance and other factors); in this case, the current source may saturate due to capacitance built up in the electrodes (and subject), as illustrated in FIG. 21B, resulting in distortion of the applied waveforms. FIGS. 21C and 21D illustrate the voltage delivered to the probes connected to the electrodes to supply the currents shown in the TES waveforms of FIGS. 21C and 21D, respectively. This saturation may be avoided using the control circuitry described herein.

Figures 22, 23A, 23B:
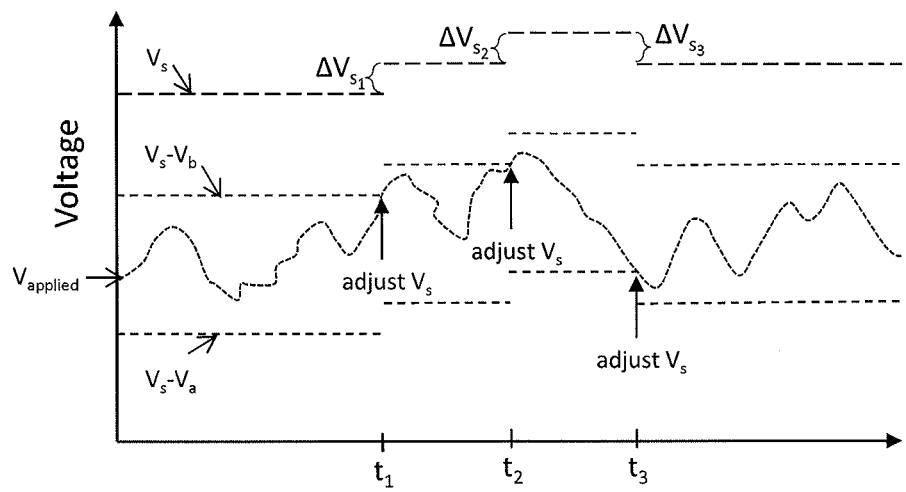
FIG. 22 graphically illustrates one variation of a method for adjusting the supply voltage ($V_s$) based on a comparison (e.g., difference) between the applied voltage and a predefined target voltage offset.
FIGS. 23A and 23B are an example of a control loop for regulating the supply voltage $V_s$ (FIG. 23B) as well as the applied current (FIG. 23A).

Thus, any of the transdermal neurostimulator apparatuses described herein may include any of the elements mentioned above, including a housing enclosing a high-voltage power supply (e.g., having a maximum voltage of greater than 10V) that is configured to provide a supply voltage of less than the maximum voltage, in which the supply voltage is adjustable, a pair of connectors configured to electrically connect with a first electrode and a second electrode, and a controller (e.g., within the housing) that includes a waveform generator configured to deliver a pulsed, asymmetric, biphasic electrical signal between the first and the second connectors, wherein the waveform generator receives the supply voltage from the high-voltage power supply. The controller may be specifically configured to compare a difference between the supply voltage ($V_s$) and an applied voltage between the first and second connectors (e.g., $V_s$-$V_{applied}$) to a target voltage offset, and the controller may adjust the supply voltage based on the comparison. For example, the controller may be configured to decrease the supply voltage ($V_s$) if the difference between the supply voltage and the applied voltage is greater than the target voltage offset, and to adjust the supply voltage by increasing the supply voltage if the difference between the supply voltage and the applied voltage is less than the target voltage offset. FIG. 22 illustrates one example of a method for adjusting the supply voltage based on this comparison. In this example, the target voltage offset is a target range that extends between $V_b$ and $V_a$ (e.g., from 4 to 7 V, $V_a$=7 V, $V_b$=4 V). In other examples, the target voltage offset is a threshold value (e.g., 6.5V). As the applied voltage between the electrodes ($V_{applied}$) varies, the difference between this applied voltage and the supply voltage ($V_s$), $V_s$-$V_{applied}$, is compared to the target voltage offset. In FIG. 22, this range is shown graphically as $V_s$-$V_b$ and $V_s$-$V_a$. As the applied voltage moves out of the range window of the target voltage offset (between $V_a$ and $V_b$) relative to the supply voltage, the supply voltage is adjusted up or down, to try and keep it at or near the target voltage offset value(s). Thus, in FIG. 22, at times $t_1$, $t_2$ and $t_3$, the supply voltage is adjusted as shown. FIG. 22 is a simplified case, in practice, the controller may also consider other states when determining how (or if) to adjust $V_s$—and the adjustments to Vs may occur frequently (i.e. every cycle, every other cycle, every $5^{th}$ cycle, every $8^{th}$ cycle, every $10^{th}$ cycle, etc.) For example, FIGS. 23A and 23B are state diagrams indicating how $V_s$ may be adjusted ($V_{adjust}$). The state diagram indicates boundary conditions for adjusting voltage (FIG. 23A) and/or applied current (FIG. 23B) under conditions that require $V_s$ adjustment to attain a target $V_s$-$V_{applied}$ (generally, increased $V_s$ is required for fields under '$V_s$ saturation' and reduced $V_s$ is required for fields not under '$V_s$ saturation'), saturation of the voltage source, or overheating. FIGS. 23A and 23B illustrate a control loop logic to adjust the target current (i.e. peak current of a electrical stimulation pulse) and supply voltage (Vs) that the controller may execute depending on logical criterion of $V_s$ saturation (i.e. $V_s$-$V_{applied}$ is outside of its target region, as shown in FIG. 22), overheat limit (to protect the user, as well as maintain components within safe operating limits), and maximum ('max') $V_s$ reached. $V_s$ saturation may mean the current sources do not have enough voltage across them to operate linearly, and are not capable of supplying sufficient voltage during a stimulation pulse, leading to distortions of square pulses (as described above in reference to FIGS. 21B and 21D). To remove the saturation the supplied voltage (power supply voltage) may be increased and/or the applied current may be decreased. If the maximum supply voltage is already being supplied as $V_s$ then no change is made to $V_s$ (FIG. 23B) and the target current delivered at the electrodes is reduced (FIG. 23A). Generally, $V_s$ is increased when $V_s$ saturation occurs, unless the maximum $V_s$ is already being delivered or an overheating condition is present, in which cases the delivered peak current is reduced instead. In general, the control logic may reduce the peak current delivered rather than distort a current waveform or maintain an overheating condition. Overheating may be derived (e.g., calculated) from the current sources transistor power. When the dissipated power is excessive, the current may be reduced. The power supply voltage may then be reduced to a level that dissipates less power by means of the Vs adjustment feedback control. Both voltages and current may be controlled to match the target values. Thus, in addition to adjusting the supply voltage, the controller may (in some instances) regulate the current applied and adjust it based on these conditions (see, e.g., the middle rows in FIG. 23). For example, the control logic may reduce the target current delivered under conditions of an overheat limit, even if the $V_s$ is not saturated.

When the supply voltage has to be adjusted as described above, it may be adjusted in any number of ways, including adjusting by a fixed amount, and/or adjusting by a percentage of the difference (e.g., between the $V_s$ and the $V_{applied}$), and/or adjusting based on recent historical values of the applied voltage (e.g., over some recent time period). In some embodiments, the supply voltage may be adjusted in an open loop manner based on an upcoming change in a waveform (e.g. a change that requires higher probe voltages such as a longer duty cycle or reduced frequency) in order to avoid an expected deviation from the acceptable voltage offset range. For example, in some variations, $V_s$ may be adjusted by, e.g., 85% of measured excursion of ($V_s$-$V_{elec}$) outside of the acceptable range. This may provide improved stability of the system, so that the changes in $V_s$ are somewhat dampened. In some variations, large adjustments may be made by adjusting by fixed increments (e.g., of about 0.5V, 1V, 1.5V, 2V, 2.5V, 3V, etc.). This may allow enough adjustment to quickly get to (e.g., approach) the acceptable range of $V_s$-$V_{elec}$ without making such a large immediate change that there could be an unsafe or uncomfortable shock from the apparatus.

As indicated above, if the adjustment to $V_s$ would exceed the maximum available power for the voltage supply, then the controller may override the requested max current. After the override, the current has a lower maximum intensity (note that the alternative would distort the signals as illustrated in FIGS. 21B and 21D, e.g., so that current falls off at the end of the pulse once the voltage supply reaches maximum).

For example, a transdermal neurostimulator apparatus may include a housing enclosing a high-voltage power supply having maximum voltage (e.g., of greater than 10V, greater than 15V, greater than 20V, greater than 25V, greater than 30V, etc.) and further configured to provide a supply voltage of less than the maximum voltage, wherein the supply voltage is adjustable. These apparatuses generally include a first connector configured to electrically connect with a first electrode and a second connector configured to electrically connect with a second electrode. Any of these apparatuses may also include a controller (e.g., within the housing) that includes, e.g., a waveform generator configured to deliver a pulsed, asymmetric, biphasic electrical signal between the first and the second connectors, wherein the waveform generator receives the supply voltage from the high-voltage power supply. Any of these controllers may also include a sensing circuit configured to detect an applied voltage between the first and second connectors (the $V_{applied}$). The sensing circuit may comprise an amplifier connected to one or both of the first and second connectors. The controller may also be configured as described herein to compare a difference between the supply voltage ($V_s$) and the applied voltage ($V_{applied}$) with a predetermined target voltage offset, and to adjust the supply voltage by decreasing the supply voltage if the difference between the supply voltage and the applied voltage is greater than the target voltage offset and to adjust the supply voltage by increasing the supply voltage if the difference between the supply voltage and the applied voltage is less than the target voltage offset.

In general, any appropriate high-voltage power supply may be used. For example, the high-voltage power supply may be configured to provide between 20V and 100V.

As mentioned above, the controller may be configured to decrease the supply voltage if the difference between the supply voltage and the applied voltage is above the target voltage offset and to increase the supply voltage if the difference between the supply voltage and the applied voltage is below the target voltage offset. The controller may be configured to adjust the supply voltage as a function of the difference between the supply voltage and the applied voltage.

In any of the apparatuses and methods described herein, the controller is configured to determine if the apparatus is in an overheating state based on an applied current and the difference between the supply voltage and the applied voltage.

As mentioned above, in various embodiments, the controller of the TES neurostimulator may include a capacitive discharge circuit configured to discharge a capacitance on the electrodes during the delivery of the biphasic electrical stimulation signal. TES neurostimulators that incorporate discharging the capacitance on the electrodes may be useful for pulsed stimulation regimes, and may help reduce or prevent pain and discomfort. In some variations the apparatus includes capacitance discharging circuitry in connection with the electrodes. For example, as described above, capacitance discharging circuitry may include electronic components and firmware features that short the anode-cathode path to permit discharge of capacitance that builds up during a pulse (e.g., in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). In general, controlling the maximum current of a capacitance discharging pulse may be beneficial for tuning the comfort of a TES waveform (e.g. to vary the maximum current of discharge based on the estimated amount of capacitance built up, which is expected to correlate with increasing imbalance (i.e. duration and/or peak current) between positive-going and negative-going pulses, as well as by frequency, where lower frequency stimulation at a fixed duty cycle will cause relatively more capacitance build-up per cycle).

In some embodiments, the wearable transdermal electrical stimulator may comprise a control module having the capacitive discharging features (which may be referred to as a 'short circuiting' applicator) described. For example, the wearable transdermal electrical stimulator may include: a housing configured to be connected to a first electrode and a second electrode, a control module at least partially within the housing including: a processor, a waveform generator configured to deliver a biphasic electrical stimulation signal between the first electrode and the second electrode, and a capacitive discharge circuit configured to discharge a capacitance on the first electrode and the second electrode during the delivery of the biphasic electrical stimulation signal. The TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation.

Figure 12A:
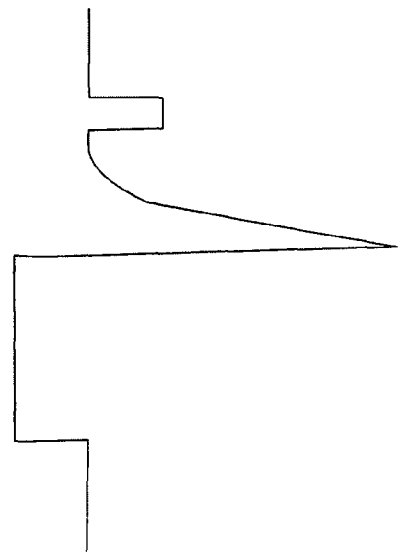
FIG. 12A schematically illustrates a biphasic electrical stimulation waveform with a positive pulse and a negative pulse in one cycle.

FIG. 12A schematically illustrates a biphasic electrical stimulation waveform with a positive pulse and a negative pulse in one cycle. In some embodiments, the firmware may create segments in a waveform cycle. The smallest segment may be limited by the clock of the processor. For example, in some embodiments, the shortest segment per cycle can be 2, 5, or 10 microseconds or any values therebetween. For example, in some embodiments, the firmware may create 10, 12, 15, or 20 segments per cycle. For each segment of the cycle, the controller may instruct the waveform generator to generate a positive intensity value, a negative intensity value, a value of "zero" which indicates an open circuit mode, or a capacitive discharge.

Figure 12B:
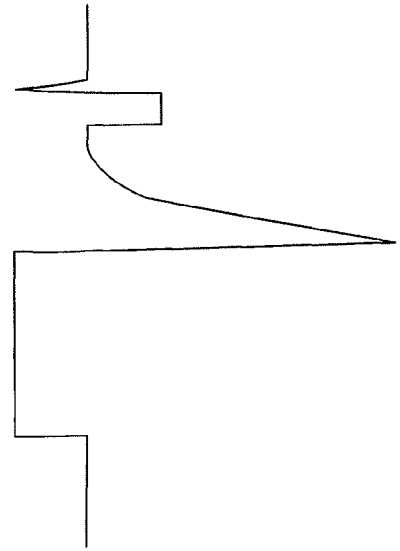
FIG. 12B schematically illustrates a capacitive discharge pulse triggered immediately after the positive pulse.
Figure 12C:
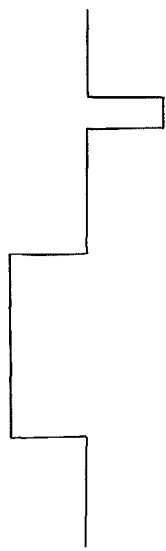
FIG. 12C schematically illustrates a capacitive discharge pulse triggered immediately after the negative pulse.
Figure 12D:
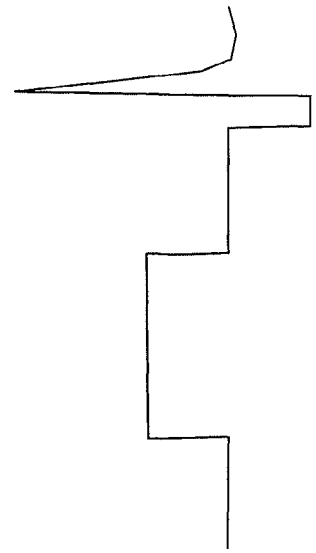
FIG. 12D schematically illustrates capacitive discharge pulses triggered immediately after the positive pulse and the negative pulse.

In some embodiments, the capacitive discharge (which may be referred to as "short-circuiting" although it is not the result of shorting) can be triggered immediately after the positive pulse or negative pulses as shown in FIGS. 12B-12D. For example, as shown in FIG. 12B, at the time when the positive pulse ends, the controller triggers the capacitive discharge circuit to short the anode-cathode path, resulting in a capacitive discharging pulse to permit discharge of capacitance. The minimum duration of the capacitive discharging pulse may be limited by the shortest segment of the cycle as discussed above. Thus the duration of the pulse can be larger than 2, 5, or 10 microseconds. However, the duration of the pulse may not be too short. It might be advantageous to have a more gradual pulse to prevent pain in the subject. It might be advantageous to have a limited peak value of the pulse to further prevent pain and discomfort. The peak value and the time constant of the capacitive discharging pulse may be controlled by the capacitive discharge circuit. In some other embodiments, the capacitive discharge can be triggered immediately after the negative pulse as shown in FIG. 12C. In some embodiments, the capacitive discharge can be triggered both after the positive pulse and after the negative pulse as shown in FIG. 12D.

Figure 12E:
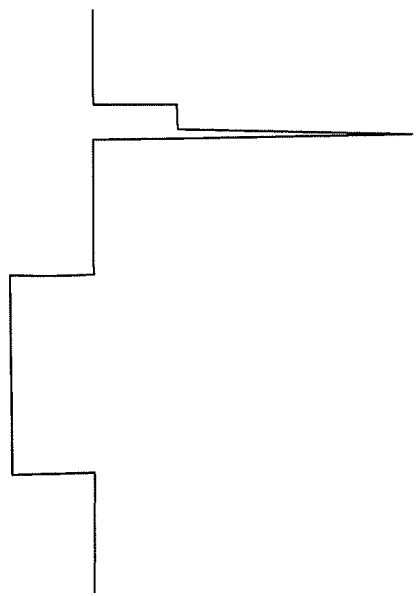
FIG. 12E schematically illustrates a capacitive discharging pulse in the negative going direction occurs at the onset of each negative going pulse.

In some alternative embodiments, the capacitive discharging pulse can be triggered at the onset of each negative-going pulse in the negative-going direction as shown in FIG. 12E. For example, in the "energy" mode, the capacitive discharging pulse can be triggered at the onset of each negative-going pulse in the negative-going direction to induce an enhanced cognitive state. In some other embodiments, the capacitive discharging pulse may be triggered at the onset of each positive-going pulse in the positive-going direction. In some other embodiments, the capacitive discharging pulse can be triggered both at the onset of each negative-going pulse in the negative-going direction and at the onset of each positive-going pulse in the positive-going direction.

Figure 13:
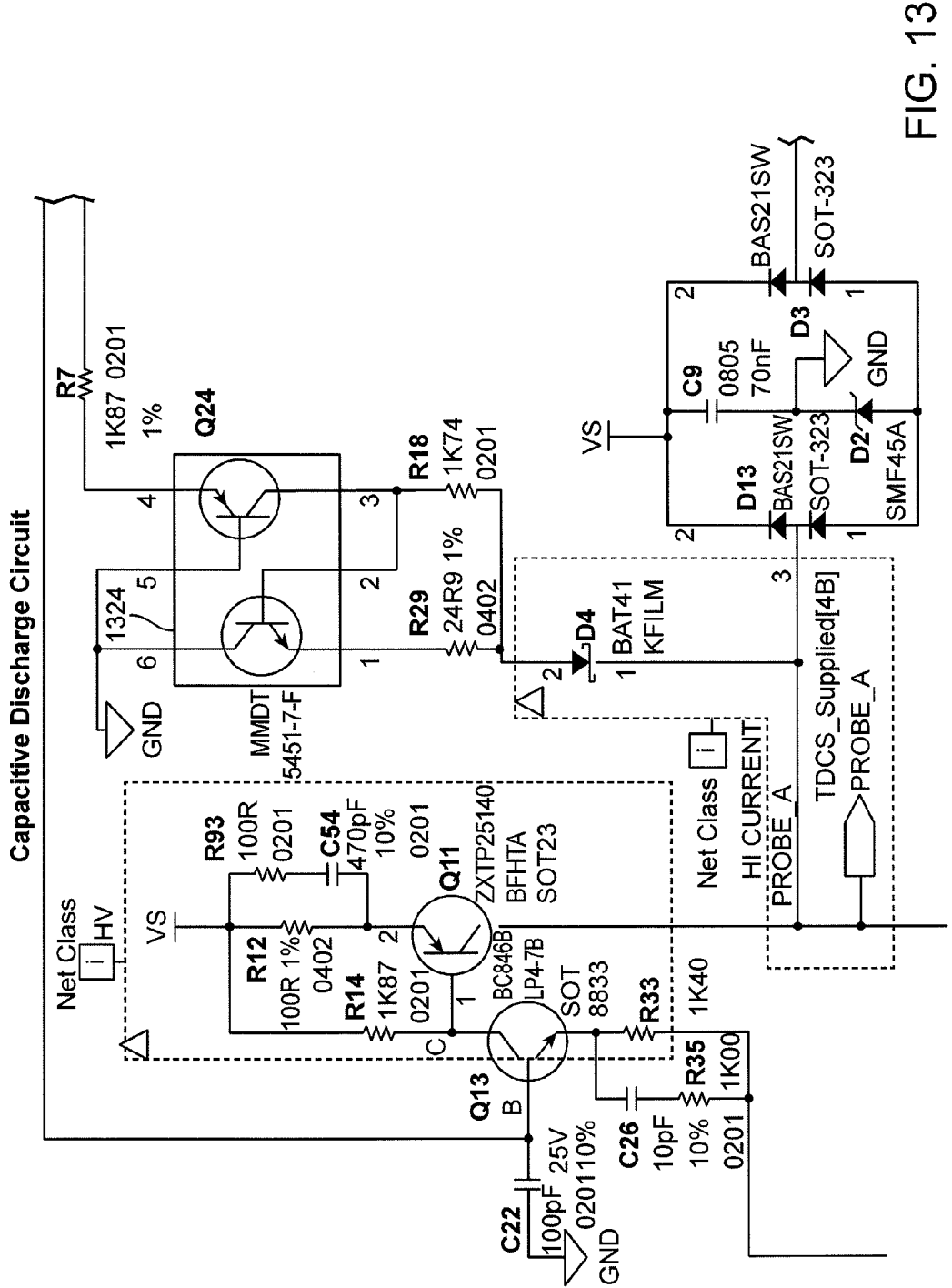
FIG. 13 schematically illustrates an example of a capacitive discharge circuit including a double H-bridge according to some embodiments of the disclosure.
Figure 13:
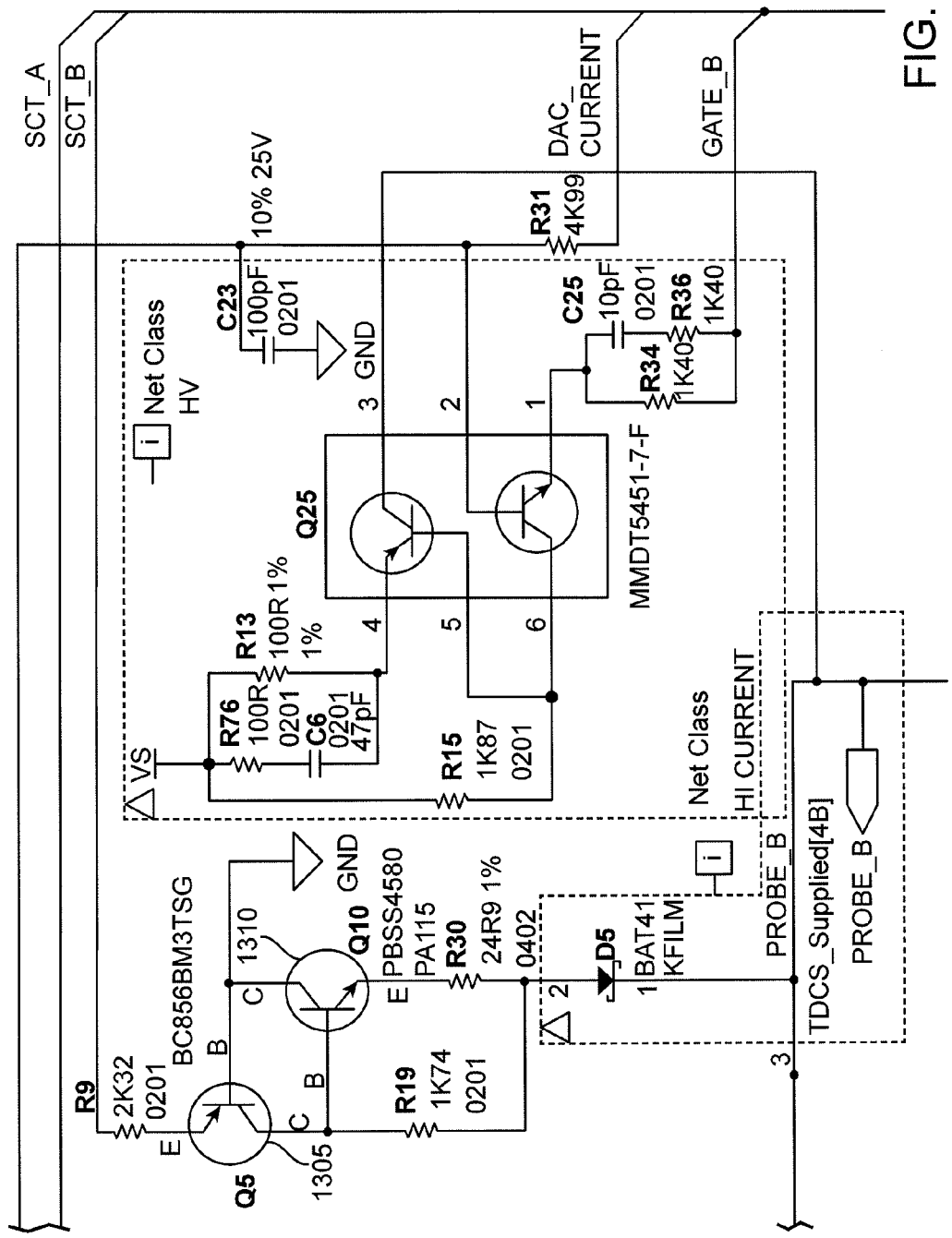

FIG. 13 schematically illustrates an example of a capacitive discharge circuit including a double H-bridge according to some embodiments of the disclosure. The double H-bridge circuit can be configured to generate a gradual capacitive discharging pulse with controlled time constant and peak value. As discussed above, the outside H-bridge can be configured to adaptively adjust the applied voltage $V_s$ based on feedback signals. In addition to the outside H-bridge, the circuit can further comprise an inside H-bridge including transistors 1324, 1305 and 1310. The transistors 1305 and 1310 can be configured to form a current source, driving the current to the ground. When probe B is negatively charged, and probe A is positively charged, the transistors 1305 and 1310 can pull probe B to ground with a gradually discharging pulse. In the other direction, the transistors 1324 can be configured to form a second current source, driving the current to the ground. When probe A is negatively charged, and probe B is positively charged, the transistors 1324 can pull probe A to ground with a second gradually discharging pulse. Therefore, the inside H-bridge including transistors 1324, 1305 and 1310 can be configured to generate gradual capacitive discharging pulses with controlled time constants and peak values. In general, the double H-bridge circuit can be configured to generate gradual capacitive discharging pulses, in addition to adaptively adjust the applied voltage Vs using feedback signals.

For example, the TEST waveform may have a frequency of 11 kHz, the time constant of the capacitive discharging pulse can be between 0.00001 to 100 microseconds. The peak value can be controlled to be between 0.001 and 10 mA in some embodiments. In some embodiments, the controller of the neurostimulator may include a switch configured to turn off the current source when the capacitive discharge circuit is triggered.

Figure 14A:
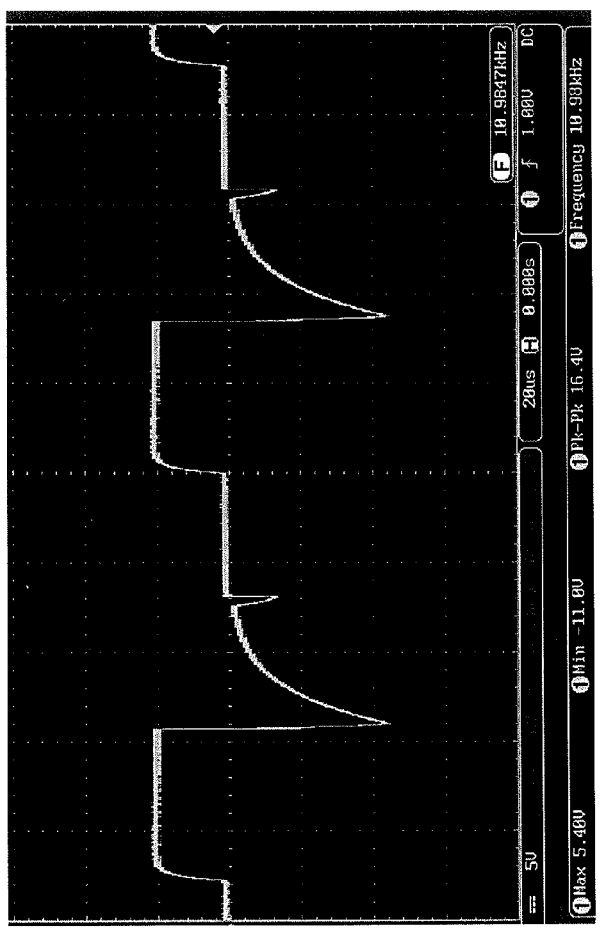
FIG. 14A illustrates an example of capacitive discharging pulses from the double H-bridge capacitive discharge circuit.

FIG. 14A illustrates an example of the capacitive discharging pulse from the double H-bridge capacitive discharge circuit. The discharging pulse immediately after the positive pulse can be controlled to have a gradual slope with a controlled peak value. The discharging pulse immediately after the negative pulse is small because there is only small amount of capacitance built up.

Figure 14B:
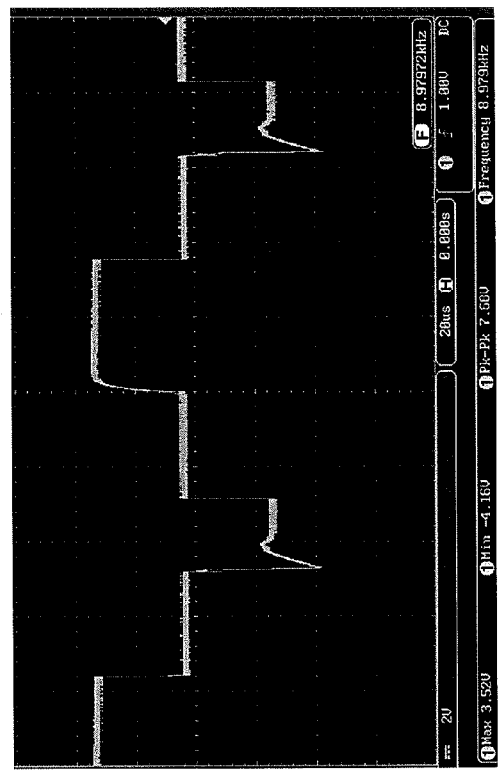
FIG. 14B illustrates another example of capacitive discharging pulses from the capacitive discharge circuit with the double H-bridge.

FIG. 14B illustrates another example of the capacitive discharging pulse from the capacitive discharge circuit with the double H-bridge. The discharging pulse is triggered at the onset of the negative going pulse in the negative going direction with a controlled time constant and peak value. The discharging pulse can be configured to enhance the "energy" cognitive state and minimize user discomfort.

In some other embodiments, the capacitance discharging circuitry may include electronic components and firmware features that short the anode-cathode path with a low ohm resistor (e.g. 50 Ohms) to permit discharge of capacitance that builds up during a pulse (e.g., in the subject's skin). In some other embodiments, the capacitive discharging circuitry may include a fixed current source similar to the main current source in the device, but saturating at 0V and allowing discharge of the accumulated charges. The discharge time may be fixed or may depend on the voltage and electrode capacitance. In one example a nominal short-circuit current may be adjustable (e.g., to 40 mA), which could be changed by changing a resistor. The discharge could be made by the regular current source with an adjustable current inside the range, e.g., up to 20 mA; turning on the two rectified bottom switches may avoid reverse charging in this case. In general, a capacitive discharge can be very quick (e.g. on the microsecond timescale) and could use a very high current, e.g., tens of mA to 100 mA.

In general, a biphasic pulse may include a positive-going pulse following (either immediately or after some delay) by a negative-going pulse. As described herein, these pulses are not limited to square-wave pulses, but may be sawtooth, or other shapes. In some variations, the positive-going and negative-going pulses may have different shapes. In some variations, the biphasic pulse includes a positive-going (or negative-going) monophasic square wave pulse and a capacitive discharge (from a capacitive discharge circuit) in the other direction. For example, the apparatus may be configured to apply a uniphasic square wave pulse (positive or negative going) and a capacitive discharge in the opposite direction. In general, TES waveforms may include bursting regimes wherein cycles of stimulation occur intermittently.

Figure 15:
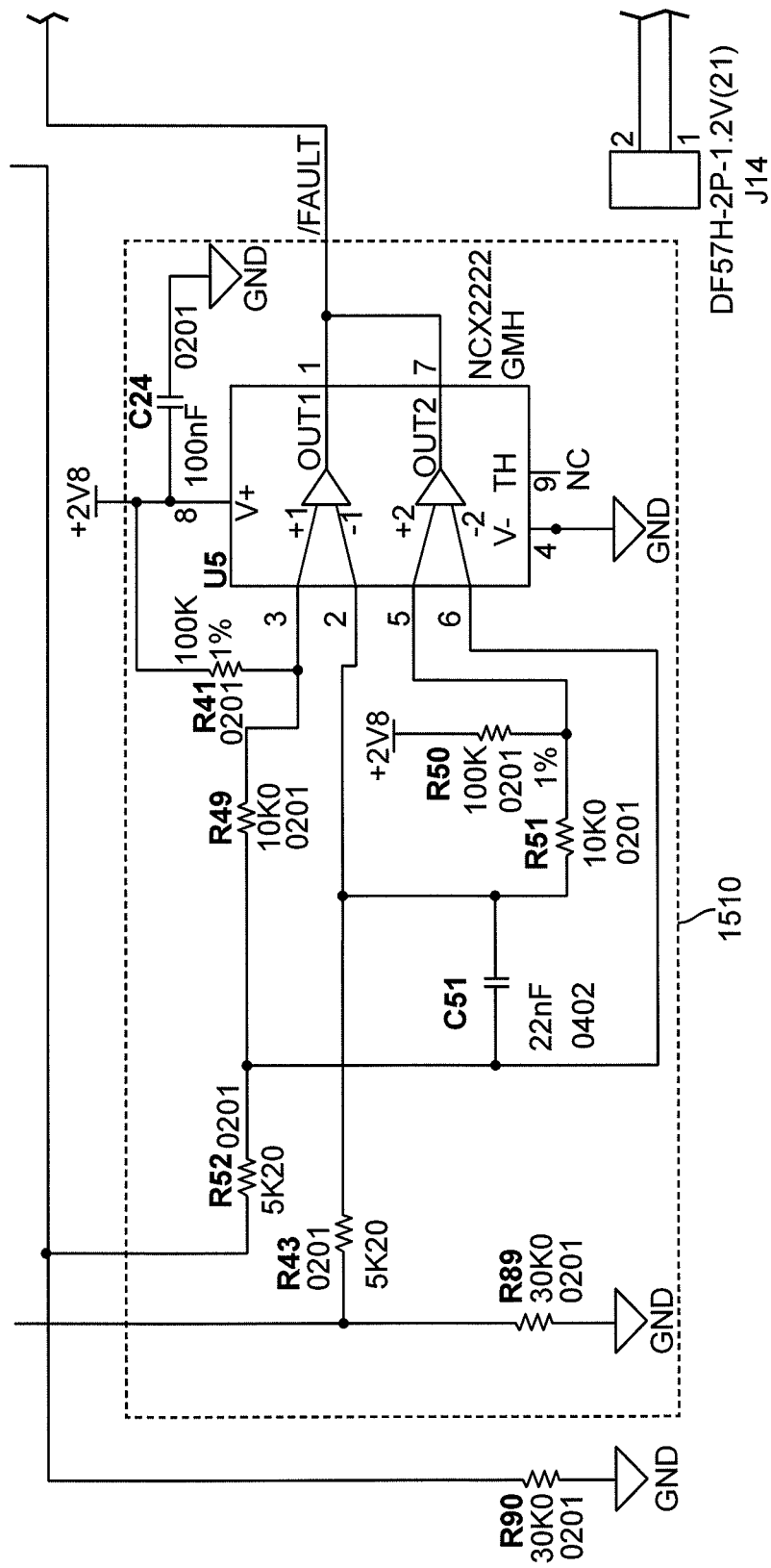
FIG. 15 schematically illustrates an example of a safety comparison circuit according to some embodiments of the disclosure.
Figure 15:
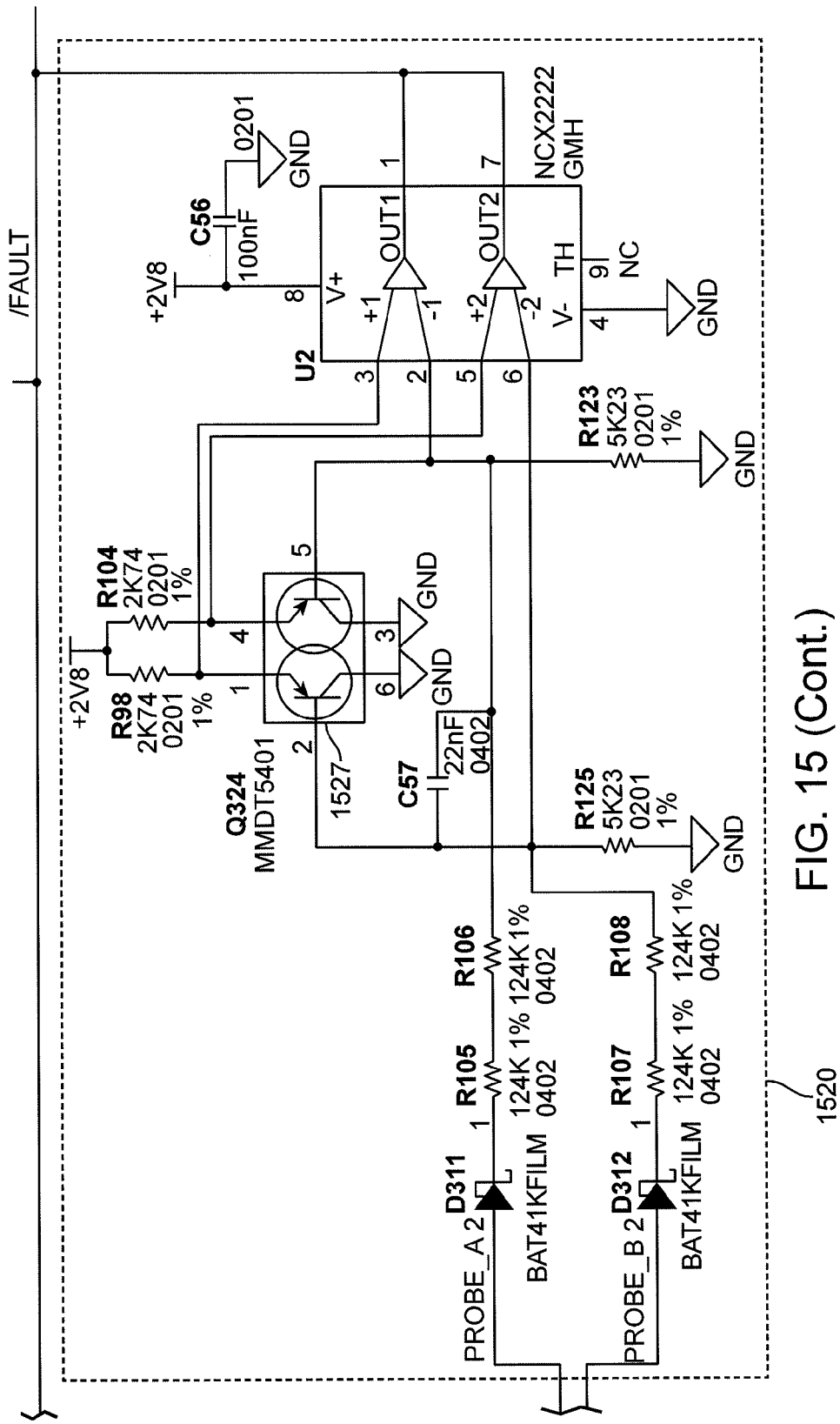

FIG. 15 schematically illustrates an example of safety comparison circuits according to some embodiments of the disclosure. In various embodiments, the controller of the neurostimulator can include safety comparison circuits configured to prevent the current and/or the voltage from exceeding maximum values. For example, the maximum DC current may be set at 5 mA, 8 mA, or 10 mA, or any values therebetween. Similarly, the voltage may have a maximum value for the safety of the subject as well. The circuit can be configured to shut down the power supply when the current or voltage exceeds the maximum value. For example, the safety circuit can comprise a current safety comparison circuit section 1510. The section 1510 can be configured to compare the current values in both directions and output a fault signal to the microprocessor if the current value in any direction exceeds the maximum value. The safety circuit can further comprise a voltage safety comparison circuit section 1520. The section 1520 can be configured to compare the voltage values in both directions and output a second fault signal to the microprocessor if the voltage value in any direction exceeds the maximum value. The voltage safety comparison circuit section 1520 can comprise a transistor 1527 to increase the sensitivity of the safety circuit.

The systems, devices, and methods of the preferred embodiments and variations thereof can be embodied and/or implemented at least in part as a machine configured to receive or include a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transdermal neurostimulator device, the device comprising:
 a housing enclosing a current source;
 a first surface on the housing;
 a first connector and a second connector, wherein the first connector is configured to electrically connect with a first electrode of an electrode apparatus and the second connector is configured to electrically connect with a second electrode; and
 a controller within the housing, the controller comprising:
  a waveform generator configured to deliver a pulsed, asymmetric, biphasic current between the first and second connectors, and
  a capacitive discharge circuit triggered by the controller and connected to one or both of the first and second connectors and configured to deliver a gradual capacitive discharging current pulse during a portion of a cycle of the biphasic electrical stimulation signal, the capacitive discharging current pulse delivering either or both: a first charge to counter a first capacitive charge on the first electrode, and a second charge to counter a second capacitive charge on the second electrode, wherein the capacitive discharge circuit includes a double H-Bridge circuit configured to generate the gradual capacitive discharging pulse.

2. The device of claim 1, wherein the first connector and a second connector are on the first surface.

3. The device of claim 1, wherein the controller is configured to trigger the capacitive discharge circuit multiple times within each cycle of the pulsed, asymmetric, biphasic electrical stimulation signal.

4. The device of claim 1, further comprising a wireless communication sub-system within the housing and connected to the controller.

5. The device of claim 1, further comprising a first electrode connected to the first connector and a second electrode connected to the second connector.

6. The device of claim 1, further wherein the controller is configured to trigger the capacitive discharge circuit to deliver the gradual capacitive discharging pulse at a start or an end of a positive-going portion of the biphasic electrical signal.

7. The device of claim 1, further wherein the controller is configured to activate the capacitive discharge circuit to deliver the gradual capacitive discharging pulse at a start or an end of a negative-going portion of the biphasic electrical signal.

8. A transdermal neurostimulator device, the device comprising:
 a housing enclosing a current source;
 a first surface on the housing;
 a first connector and a second connector, wherein the first connector is configured to electrically connect with a first electrode of an electrode apparatus and the second connector is configured to electrically connect with a second electrode; and
 a controller within the housing, the controller comprising:
  a waveform generator configured to deliver a pulsed, asymmetric, biphasic current between the first and second connectors, and
  a capacitive discharge circuit triggered by the controller and connected to one or both of the first and second connectors and configured to deliver a gradual capacitive discharging current pulse during a portion of a cycle of the biphasic electrical stimulation signal, the capacitive discharging current pulse delivering either or both: a first charge to counter a first capacitive charge on the first electrode, and a second charge to counter a second capacitive charge on the second electrode, further wherein the controller is configured to trigger the capacitive discharge circuit to deliver the gradual capacitive discharging pulse at a start or an end of a positive-going portion of the biphasic electrical signal.

9. The device of claim 8, wherein the first connector and a second connector are on the first surface.

10. The device of claim 8, wherein the controller is configured to trigger the capacitive discharge circuit multiple times within each cycle of the pulsed, asymmetric, biphasic electrical stimulation signal.

11. The device of claim 8, further comprising a wireless communication sub-system within the housing and connected to the controller.

12. The device of claim 8, further comprising a first electrode connected to the first connector and a second electrode connected to the second connector.

13. A transdermal neurostimulator device, the device comprising:
 a housing enclosing a current source;
 a first surface on the housing;
 a first connector and a second connector, wherein the first connector is configured to electrically connect with a first electrode of an electrode apparatus and the second connector is configured to electrically connect with a second electrode; and
 a controller within the housing, the controller comprising:
  a waveform generator configured to deliver a pulsed, asymmetric, biphasic current between the first and second connectors, and
  a capacitive discharge circuit triggered by the controller and connected to one or both of the first and second connectors and configured to deliver a gradual capacitive discharging current pulse during a portion of a cycle of the biphasic electrical stimulation signal, the capacitive discharging current pulse delivering either or both: a first charge to counter a first capacitive charge on the first electrode, and a second charge to counter a second capacitive charge on the second electrode, further wherein the controller is configured to activate the capacitive discharge circuit to deliver the gradual capacitive discharging pulse at a start or an end of a negative-going portion of the biphasic electrical signal.

14. The device of claim 13, wherein the first connector and a second connector are on the first surface.

15. The device of claim 13, wherein the controller is configured to trigger the capacitive discharge circuit multiple times within each cycle of the pulsed, asymmetric, biphasic electrical stimulation signal.

16. The device of claim 13, further comprising a wireless communication sub-system within the housing and connected to the controller.

17. The device of claim 13, further comprising a first electrode connected to the first connector and a second electrode connected to the second connector.

* * * * *